US009970056B2

(12) United States Patent
Potashkin et al.

(10) Patent No.: US 9,970,056 B2
(45) Date of Patent: May 15, 2018

(54) METHODS AND KITS FOR DIAGNOSING, PROGNOSING AND MONITORING PARKINSON'S DISEASE

(71) Applicant: Rosalind Franklin University of Medicine and Science, North Chicago, IL (US)

(72) Inventors: Judith Ann Potashkin, North Chicago, IL (US); Jose Alfredo Santiago, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 94 days.

(21) Appl. No.: 14/870,960

(22) Filed: Sep. 30, 2015

(65) Prior Publication Data
US 2016/0244833 A1 Aug. 25, 2016

Related U.S. Application Data

(60) Provisional application No. 62/120,848, filed on Feb. 25, 2015.

(51) Int. Cl.
*C12Q 1/68* (2018.01)
(52) U.S. Cl.
CPC ..... *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,772,468 B2 | 7/2014 | Potashkin | |
| 8,841,436 B2 | 9/2014 | Gorodeski et al. | |
| 2005/0026191 A1* | 2/2005 | Carman | C07K 14/47 435/6.16 |
| 2011/0021600 A1* | 1/2011 | Yamada | A61K 31/7088 514/44 A |

OTHER PUBLICATIONS

Adler, et al., "Low Clinical Diagnostic Accuracy of Early vs Advanced Parkinson's Disease: Clinicopathologic Study", *Neurology*, Jul. 29, 2014, vol. 83, pp. 406-412.
Alieva, et al., "Involvement of Endocytosis and Alternative Splicing in the Formation of the Pathological Process in the Early Stages of Parkinson's Disease", *Biomed Res Int*, 2014, vol. 2014, Article ID 718732, doi:10.1155/2014/718732, Epub Apr. 3, 2014.
Aviles-Olmos, et al., "Exenatide and the Treatment of Patients with Parkinson's Disease", *The Journal of Clinical Investigation*, 2013, vol. 123(6), pp. 2730-2736.
Aviles-Olmos, et al. "Motor and Cognitive Advantages Persist 12 Months After Exenatide Exposure in Parkinson's Disease", *Journal of Parkinson's Disease*, 2014, vol. 4, pp. 337-344.
Aviles-Olmos, et al. "Parkinson's Disease, Insulin Resistance and Novel Agents of Neuroprotection", *Brain*, 2013, vol. 136(Pt 2), pp. 374-384.
Bassil, et al, "Insulin, IGF-1 and GLP-1 Signaling in Neurodegenerative Disorders: Targets for Disease Modification?", *Prog Neurobiol*, Jul. 2014, vol. 118, pp. 1-18. (Abstract only).
Bonnefond, et al., "The Emerging Genetics of Type 2 Diabetes", *Trends Mol Med*, Sep. 2010, vol. 16(9), pp. 407-416. (Abstract only).
Cereda, et al., "Diabetes and Risk of Parkinson's Disease: A Systematic Review and Meta-Analysis", *Diabetes Care*, Dec. 2011, vol. 34, pp. 2614-2623.
Cereda, et al., "Diabetes and Risk of Parkinson's Disease", *Movement Disorders*, 2013, vol. 28, pp. 257-261 (Abstract only).
Cereda, et al., "Clinical Features of Parkinson's Disease When Onset of Diabetes Came First: A Case-Control Study", *Neurology*, May 8, 2012, vol. 78(19), pp. 1507-1511, doi: 10.1212/WNL.0b013e3182553cc9, Epub Apr. 25, 2012. (Abstract only).
Chen-Plotkin, et al., "Plasma Epidermal Growth Factor Levels Predict Cognitive Decline in Parkinson's Disease ", *Ann Neurol*, Apr. 2011, vol. 69(4), pp. 655-663, doi:10.1002/ana.22271, Epub Nov. 29, 2010.
Deas, et al., "PINK1 Deficiency in Beta-Cells Increases Basal Insulin Secretion and Improves Glucose Tolerance in Mice", *Open Biol*, Apr. 7, 2014, vol. 4, p. 140051, http://dx.doi.org/10.1098/rsob.140051.
DiFonzo, et al., "A Frequent LRRK2 Gene Mutation Associated with Autosomal Dominant Parkinson's Disease", *Lancet*, Jan. 29, 2005, vol. 365(9457), pp. 412-415. (Abstract only).
Ding, et al., "Association of SNCA with Parkinson: Replication in the Harvard NeuroDiscovery Center Biomarker Study", *Movement Disorders*, 2011, vol. 26, pp. 2283-2286.
Ding, et al., "Unrecognized Vitamin D3 Deficiency is Common in Parkinson's Disease: Harvard Biomarker Study", *Neurology*, Oct. 22, 2013, vol. 81(17), pp. 1531-1537.
Dunn, et al., "Dysregulation of Glucose Metabolism is an Early Event in Sporadic Parkinson's Disease", *Neurobiology of Aging*, May 2014, vol. 35(5), pp. 1111-1115.
Farrer, et al., "LRRK2 Mutations in Parkinson's Disease", *Neurology*, Sep. 13, 2005, vol. 65(5), pp. 738-740. (Abstract only).

(Continued)

*Primary Examiner* — James S Ketter
(74) *Attorney, Agent, or Firm* — McDonnell Boehnen Hulbert & Berghoff LLP

(57) ABSTRACT

Network-based meta-analysis of four independent microarray studies identified the hepatocyte nuclear factor (HNF4A), a transcription factor associated with gluconeogenesis and diabetes, as a central regulatory hub gene upregulated in blood of PD patients. In parallel, the polypyrimidine tract binding protein 1 (PTBP1), involved in the stabilization and mRNA translation of insulin, was identified as the most downregulated gene. Using both markers, PD patients were classified with 90% sensitivity and 80% specificity. Longitudinal performance analysis demonstrated that relative abundance of HNF4A and PTBP1 mRNAs significantly decreased and increased, respectively, in PD patients during 3 years follow up period. The inverse regulation of HNF4A and PTBP1 provides a molecular rationale for the altered insulin signaling observed in PD patients. The longitudinally dynamic biomarkers identified in this study may be useful for monitoring disease-modifying therapies for PD.

12 Claims, 8 Drawing Sheets

(56) References Cited

OTHER PUBLICATIONS

Foltynie, et al., "Exenatide as a Potential Treatment for Patients with Parkinson's Disease: First Steps into the Clinic", *Alzheimer & Dementia*, Feb. 2014, vol. 10, pp. S38-46, doi:10.1016/j.jalz.2013.12.005.

Geng, et al., "Alpha-Synuclein Binds the K(ATP) Channel at Insulin-Secretory Granules and Inhibits Secretion", *Am J Physiol Endocrinol Metab*, Feb. 2011, vol. 300(2), pp. E276-286, doi:10.1152/ajpendo.00262.2010, Epub Sep. 21, 2010.

Gilks, et al., "A Common LRRK2 Mutation in Idiopathic Parkinson's Disease", *Lancet*, Jan. 18, 2005, vol. 365(9457), pp. 415-416. (Abstract only).

Han, et al., "Diagnosis of Parkinson's Disease Based on Disease-Specific Autoantibody Profiles in Human Sera", *PloS One*, 2012, vol. 7(2), Article ID e32383, pp. 1-6, doi:10.1371/journal.pone.0032383, Epub Feb. 22, 2012.

Harries, et al., "The Diabetic Phenotype in HNF4A Mutation Carriers is Moderated by the Expression of HNF4A Isoforms from the P1 Promoter During Fetal Development", *Diabetes*, Jun. 2008, vol. 57(6), pp. 1745-1752, doi:10.2337/db07-1742, Epub Mar. 20, 2008.

Hegele, et al., "Dynamic Protein-Protein Interaction Wiring of the Human Spliceosome", *Mol Cell*, Feb. 24, 2012, vol. 45(4), pp. 567-580, doi:10.1016/j.molcel.2011.12.034.

Hetz, et al., "Targeting the Unfolded Protein Response in Disease", *Nat Rev Drug Discov*, Sep. 2013, vol. 12(9), pp. 703-719, doi:10.1038/nrd3976. (Abstract only).

Hu, et al., "Type 2 Diabetes and the Risk of Parkinson's Disease", *Diabetes Care*, Apr. 2007, vol. 30(4), pp. 842-847, Epub Jan. 24, 2007.

Jain, et al, "Age- and Diet-Dependent Requirement of DJ-1 for Glucose Homeostasis in Mice with Implications for Human Type 2 Diabetes", *J Mol Cell Biol*, Aug. 2012, vol. 4(4), pp. 221-230, doi:10.1093/jmcb/mjs025, Epub May 19, 2012.

Knoch, et al, "cAMP-Dependent Phosphorylation of PTB1 Promotes the Expression of Insulin Secretory Granule Proteins in Beta Cells", *Cell Metab*, Feb. 2006, vol. 3(2), pp. 123-134.

Konstandi, et al., "Role of PPARalpha and HNF4alpha in Stress-Mediated Alterations in Lipid Homeostasis", *Plos One*, Aug. 14, 2013, vol. 8(8), Article ID e70675, pp. 1-12, doi:10.1371/journal.pone.0070675, eCollection 2013.

Li, et al, "GLP-1 Receptor Stimulation Preserves Primary Cortical and Dopaminergic Neurons in Cellular and Rodent Models of Stroke and Parkinsonism", *Proc Natl Acad Sci USA*, Jan. 27, 2009, vol. 106(4), pp. 1285-1290, doi:10.1073/pnas.0806720106, Epub Jan. 21, 2009.

Lu, et al., "Diabetes and Risk of Parkinson's Disease: An Updated Meta-Analysis of Case-Control Studies", *PloS One*, 2014, vol. 9(1), Article ID e85781, pp. 1-12.

Marcil, et al., "Modification in Oxidative Stress, Inflammation, and Lipoprotein Assembly in Response to Hepatocyte Nuclear Factor 4alpha Knockdown in Intestinal Epithelial Cells", *The Journal of Biological Chemistry*, 2010, vol. 285(52), pp. 40448-40460.

Mehanna, et al., "Unrecognized Vitamin D3 Deficiency is Common in Parkinson's Disease: Harvard Biomarker Study", *Neurology*, May 6, 2014, vol. 82(18), p. 1666, Discussion 1666, doi: 10.1212/01.wnl.0000449750.81263.7d.

Menon, et al., "Shared Molecular and Functional Frameworks Among Five Complex Human Disorders: A Comparative Study on Interactomes Linked to Susceptibility Genes", *PloS One*, 2011, vol. 6(4), Article ID e18660, pp. 1-9, Epub Apr. 21, 2011.

Mercado, et al., "An ERcentric View of Parkinson's Disease", *Trends Mol Med*, Mar. 2013, vol. 19(3), pp. 165-175, doi: 10.1016/j.molmed.2012.12.005, Epub Jan. 24, 2013. (Abstract only).

Moher, et al., "Preferred Reporting Items for Systematic Reviews and Meta-Analysis: the PRISMA Statement", *PLoS Med*, Jul. 21, 2009, vol. 6(7), Article ID e1000097, pp. 1-6, doi:10.1371/journal.pmed.1000097, Epub Jul. 21, 2009.

Molochnikov, et al., "A Molecular Signature in Blood Identifies Early Parkinson's Disease", *Mol Neurodegener*, May 31, 2012, vol. 7, p. 26, doi:10.1186/1750-1326-7-26.

Moroo, et al., "Loss of Insulin Receptor Immunoreactivity from the Substantia Nigra Pars Compacta Neurons in Parkinson's Disease", *Acta Neuropathol*, 1994, vol. 87(4), pp. 343-348. (Abstract only).

Morris, et, al., "Neurodegeneration in an Animal Model of Parkinson's Disease is Exacerbated by a High-Fat Diet", *Am J Physiol Regul Integr Comp Physiol*, Oct. 2010, vol. 299(4), pp. R1082-1090, doi:10.1152/ajpregu.00449.2010, Epub Aug. 11, 2010.

Morris, et al., "Insulin Resistance Impairs Nigrostriatal Dopamine Function", *Exp Neurol*, Sep. 2011, vol. 231(1), pp. 171-180, doi:10.1016/j.expneurol.2011.06.005.

Mutez, et al., "Transcriptional Profile of Parkinson's Blood Mononuclear Cells with LRRK2 Mutation", *Neurobiol Aging*, Oct. 2011, vol. 32(10), pp. 1839-1848, doi: 10.1016/j.neurobiolaging.2009.10.016, Epub Jan. 22, 2010. (Abstract only).

Nolan, et al., "Parkinson's Disease in the Nuclear Age of Neuroinflammation", *Trends in Molecular Medicine*, Mar. 2013, vol. 19, pp. 187-196, Epub Jan. 11, 2013. (Abstract only).

Potashkin, et al., "Biosignatures for Parkinson's Disease and Atypical Parkinsonian Disorders Patients", *PloS One*, 2012, vol. 7(8), Article ID e43595, pp. 1-13.

Przedborski, "Inflammation and Parkinson's Disease Pathogenesis", *Movement Disorders: Official Journal of the Movement Disorder Society*, 2010, vol. 25, Suppl 1, pp. S55-S57.

Puigserver, et al., "Insulin-Regulated Hepatic Gluconeogenesis Through FOXO1-PGC-1alpha Interaction", *Nature*, May 29, 2003, vol. 423(6939), pp. 550-555, Epub May 18, 2003. (Abstract only).

Rajput, et al., "Accuracy of Parkinson's Disease Diagnosis Unchanged in 2 Decades", *Neurology*, 2014, vol. 85(5), pp. 386-387, Epub Jun. 27, 2014. (Abstract only).

Rhee, et al., "Regulation of Hepatic Fasting Response by PPARgamma Coactivator-1 alpha (PGC-1): Requirement for Hepatocyte Nuclear Factor 4alpha in Gluconeogenesis", *Proc Natl Acad Sci USA*, Apr. 1, 2003, vol. 100(7), pp. 4012-4017.

Rhodes, et al., "Meta-Analysis of Microarrays: Interstudy Validation of Gene Expression Profiles Reveals Pathway Dysregulation in Prostate Cancer", *Cancer Res*, Aug. 1, 2002, vol. 62(15), pp. 4427-4433.

Rothman, et al, "Metabolic Abnormalities and Hypoleptinemia in Alpha-Synuclein A53T Mutant Mice", *Neurobiol Aging*, May 2014, vol. 35(5), pp. 1153-1161, doi:10.1016/j.neurobiolaging.2013.10.088.

Rotermund, et al., "Diet-Induced Obesity Accelerates the Onset of Terminal Phenotypes in Alpha-Synuclein Transgenic Mice", *J Neurochem*, Dec. 2014, vol. 131(6), pp. 848-858, doi:10.1111/jnc.12813, Epub Aug. 11, 2014. (Abstract only).

Santiago, et al., "Integrative Network Analysis Unveils Convergent Molecular Pathways in Parkinson's Disease and Diabetes", *PloS One*, Dec. 2013, vol. 8(12), Article ID e83940, pp. 1-8.

Santiago, et al., "A Network Approach to Diagnostic Biomarkers in Progressive Supranuclear Palsy", *Movement Disorders*, 2014, vol. 29(4), pp. 550-555.

Santiago, et al., "Shared Dysregulated Pathways Lead to Parkinson's Disease and Diabetes", *Trends in Molecular Medicine*, 2013, vol. 19(3), pp. 176-186.

Santiago, et al., "System-Based Approaches to Decode the Molecular Links in Parkinson's Disease and Diabetes", *Neurobiology of Disease*, 2014, http://dx.doi.org/10.1016/j.nbd.2014.03.019.

Santiago, et al., "Specific Splice Variants are Associated with Parkinson's Disease", *Movement Disorders*, 2013, vol. 28(12), pp. 1724-1727.

Santiago, et al., "Network Analysis Identifies SOD2 mRNA as a Potential Biomarker for Parkinson's Disease", *PloS One*, Oct. 2014, vol. 9(10), Article ID e109042, pp. 1-9.

Santiago, et al., "Network-Based Metaanalysis Identifies HNF4A and PTBP1 as Longitudinally Dynamic Biomarkers for Parkinson's Disease", *PNAS*, Feb. 17, 2015, vol. 112(7), pp. 2257-2262.

Santiago, et al., "A Network Approach to Clinical Intervention in Neurodegenerative Diseases", *Trends Mol Med*, Dec. 2014, vol. 20(12), pp. 694-703, doi:10.1016/j.molmed.2014.10.002, Epub Oct. 30, 2014. (Abstract only).

(56) References Cited

OTHER PUBLICATIONS

Scheele, et al., "Altered Regulation of the PINK1 Locus: A Link Between Type 2 Diabetes and Neurodegeneration", *FASEB Journal*, 2007, vol. 21, pp. 3653-3665.
Scherzer, et al., "Molecular Markers of Early Parkinson's Disease Based on Gene Expression in Blood", *Proceedings of the National Academy of Sciences of the United States of America*, 2007, vol. 104(3), pp. 955-960.
Scherzer, et al., "GATA Transcription Factors Directly Regulate the Parkinson's Disease-Linked Gene Alpha-Synuclein", *Proc Natl Acad Sci USA*, Aug. 5, 2008, vol. 105(31), pp. 10907-10912.
Shehadeh, et al., "SRRM2, a Potential Blood Biomarker Revealing High Alternative Splicing in Parkinson's Disease", PLoS One, Feb. 8, 2010, vol. 5(2), Article ID e9104, pp. 1-8, doi:10.1371/journal.pone.0009104.
Soreq, et al., "Exon Arrays Reveal Alternative Splicing Aberrations in Parkinson's Disease Leukocytes", *Neurodegener Dis*, 2012, vol. 10(1-4), pp. 203-206, doi:10.1159/000332598, Epub Dec. 9, 2011.
Soreq, et al, "Small RNA Sequencing-Microarray Analyses in Parkinson's Leukocytes Reveal Deep Brain Stimulation-Induced Splicing Changes that Classify Brain Region Transcriptomes", *Front Mol Neurosci*, May 13, 2013, vol. 6, Article ID 10, pp. 1-20, doi:10.3389/fnmol.2013.00010, eCollection 2013.
Soreq, et al, "Long Non-Coding RNA and Alternative Splicing Modulations in Parkinson's Leukocytes Identified by RNA Sequencing", *PLoS Comput Biol*, Mar. 20, 2014, vol. 10(3), Article ID e1003517, pp. 1-22, doi:10.1371/journal.pcbi.1003517, eCollection 2014.
Tseng, et al, "Comprehensive Literature Review and Statistical Considerations for Microarray Meta-Analysis", *Nucleic Acids Res*, 2012, vol. 40(9), pp. 3785-3799, doi:10.1093/nar/gkr1265, Epub Jan. 19, 2012.
Valdes, et al., "Control of Dopaminergic Neuron Survival by the Unfolded Protein Response Transcription Factor XBP1", *Proc Natl Acad Sci USA*, May 6, 2014, vol. 111(18), pp. 6804-6809.
Wang, et al., "Metabolic Inflammation Exacerbates Dopaminergic Neuronal Degeneration in Response to Acute MPTP Challenge in Type 2 Diabetes Mice" *Experimental Neurology*,2014, vol. 251, pp. 22-29, Epub Nov. 9, 2013. (Abstract only).
Xia, et al., "INMEX—A Web-based Tool for Integrative Meta-Analysis of Expression Data", *Nucleic Acids Res*, 2013, vol. 41 (Web Server issue), pp. W63-70, doi:10.1093/nar/gkt338, Epub Jun. 12, 2013.
Xia, et al., "Network Analyst—Integrative Approaches for Protein—Protein Interaction Network Analysis and Visual Exploration" *Nucleic Acids Res*, Jul. 2014, vol. 42(Web Server issue), pp. W167-174, doi:10.1093/nar/gku443, Epub May 26, 2014.
Yin, et al., "Hepatic Hepatocyte Nuclear Factor 4alpha is Essential for Maintaining Triglyceride and Cholesterol Homeostasis", *Arterioscler Throm Vasc Biol*, Feb. 2011, vol. 31(2), pp. 328-336, doi:10.1161/ATVBAHA.110.217828.
Zheng, et al., "PGC-1alpha, a Potential Therapeutic Target for Early Intervention in Parkinson's Disease", *Sci Transl Med*, Oct. 6, 2010, vol. 2(52), pp. 52ra73, doi:10.1126/scitranslmed.3001059.
Zoubarev, et al., "Gemma: A Resource for the Reuse, Sharing and Meta-Analysis of Expression Profiling Data", *Bioinformatics*, 2012, vol. 28(17), pp. 2272-2273, doi:10.1093/bioinformatics/bts430, Epub Jul. 10, 2012.

\* cited by examiner

FIG.1A Microarrays

INMEX: Meta-analysis

NetworkAnalyst

Biomarker discovery

FIG.1B

Meta-DE / Individual-DE

Gain 921 | 1860 | Loss 491

Class: PD, HC
Microarrays: GSE18838, GSE22491, GSE54536, GSE6613

FIG.1C

SLC4A1, DAZAP2, PTBP1, RTN3, MEF2D, CACNA1E, CACNA1I, SF3A2, CKB, CYP11B1, SEMA6B, SPATA2L, BCAM, SYNGR4, EN2, TPSG1, SPEF1, HNF4A, THY1

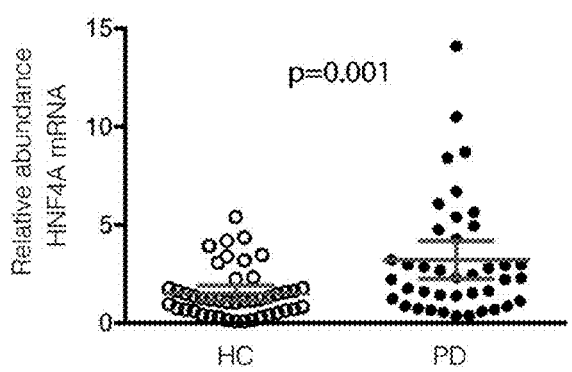
FIG. 3A PROBE Cohort
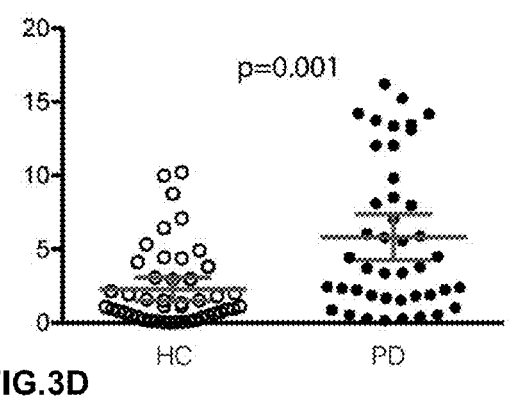
FIG. 3B HBS Cohort
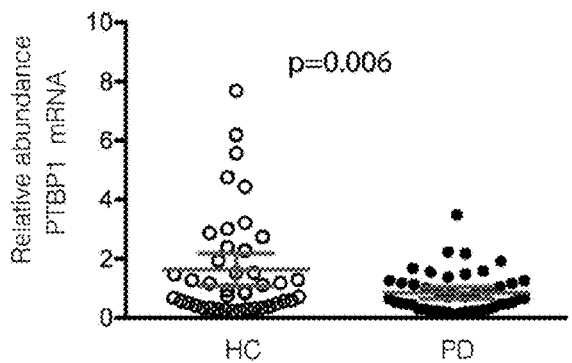
FIG. 3C
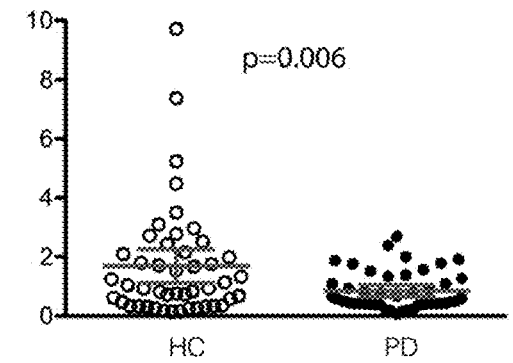
FIG. 3D

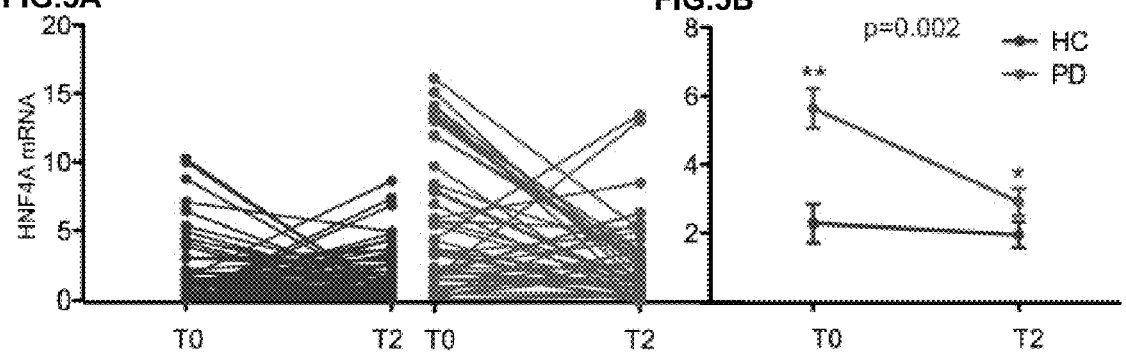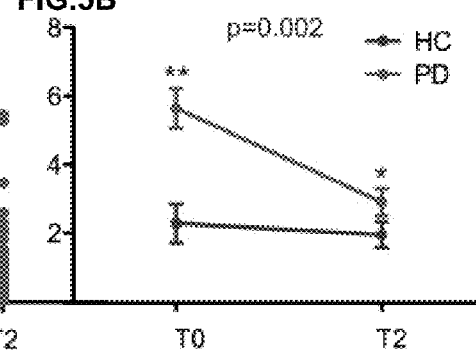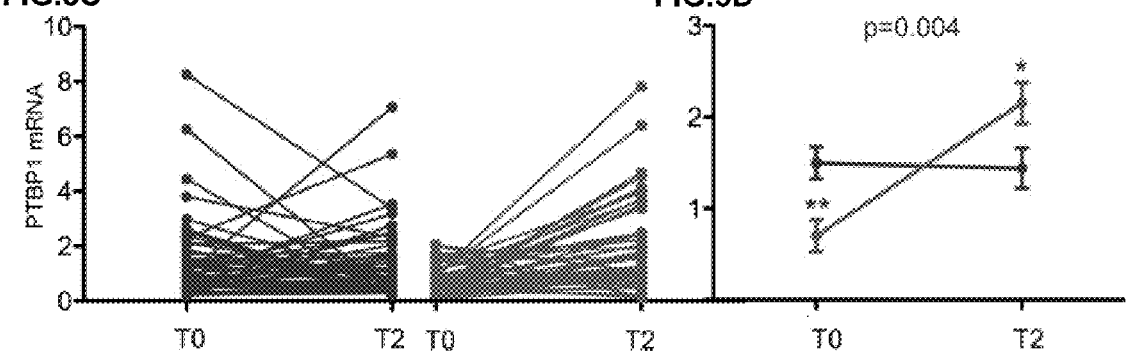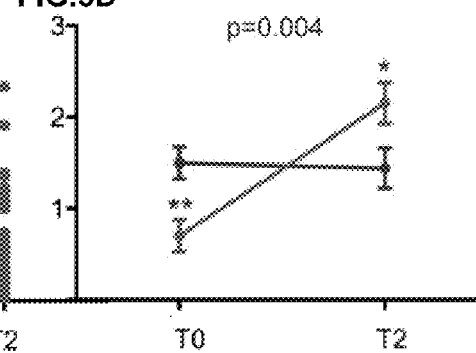

FIG. 7A Upregulated splicing factors
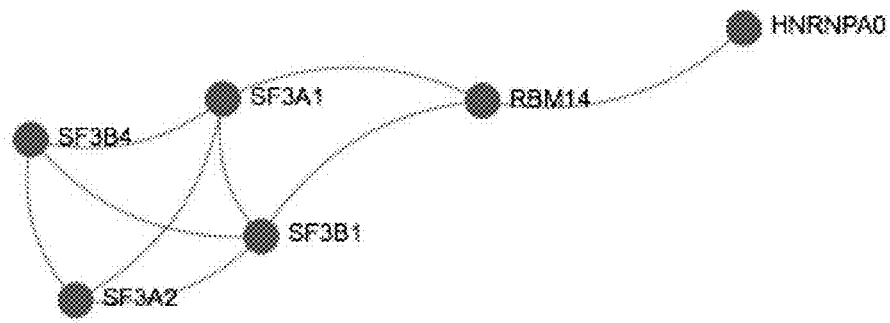
FIG. 7B Downregulated splicing factors
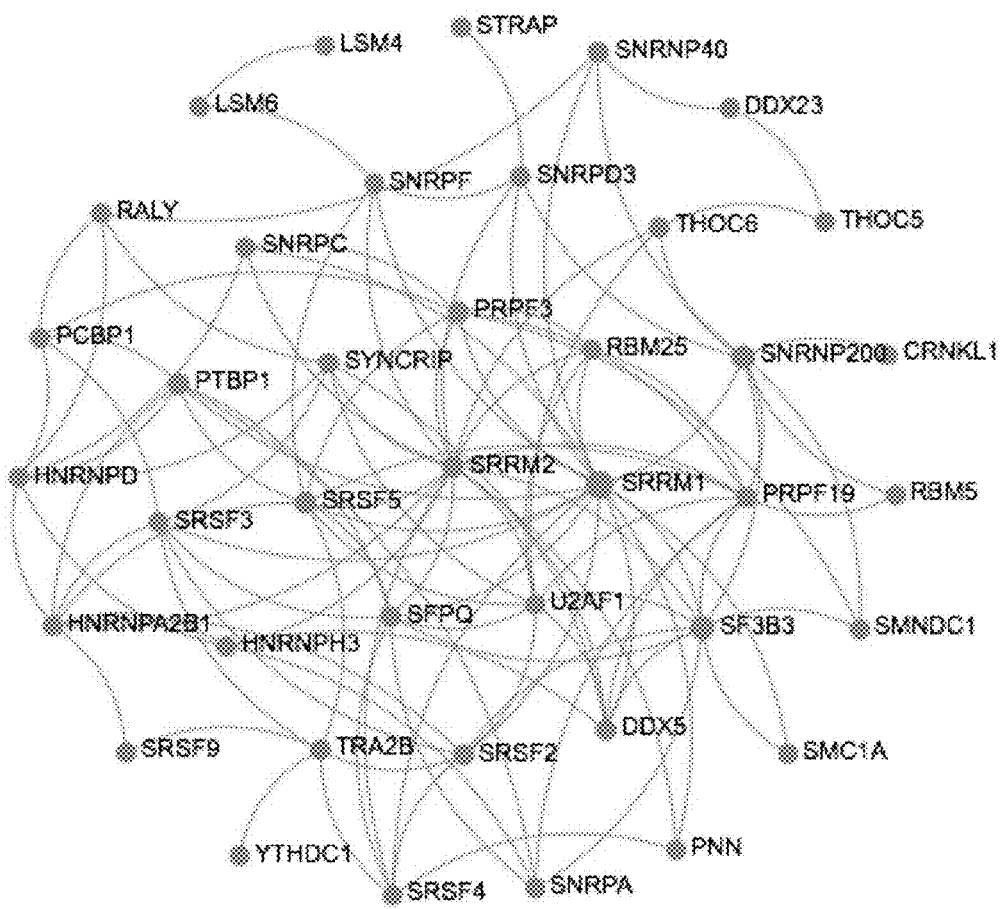

METHODS AND KITS FOR DIAGNOSING, PROGNOSING AND MONITORING PARKINSON'S DISEASE

CROSS REFERENCE

This application is related to U.S. provisional patent application No. 62/120,848, filed Feb. 25, 2015, the disclosure of which is incorporated by reference herein in its entirety. The sequence listing submitted herewith is incorporated by reference in its entirety.

STATEMENT REGARDING FEDERALLY SPONSORED RESEARCH

This invention was made with U.S. government support by the US Army Medical Research and Materiel Command under awards number W81XWH-09-0708 and W81XWH13-1-0025.

BACKGROUND OF THE DISCLOSURE

Parkinson's disease (PD; also known as idiopathic or primary parkinsonism, hypokinetic rigid syndrome (HRS), or paralysis agitans) belongs to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 60. Early symptoms of PD are subtle and occur gradually. In some people the disease progresses more quickly than in others. As the disease progresses, the shaking, or tremor, which affects the majority of people with PD may begin to interfere with daily activities. Other symptoms may include depression and other emotional changes; difficulty in swallowing, chewing, and speaking; urinary problems or constipation; skin problems; and sleep disruptions. There are currently no blood or laboratory tests that have been proven to help in diagnosing sporadic PD. Therefore the diagnosis is based on medical history and a neurological examination, but the disease can be difficult to diagnose accurately. Doctors may sometimes request brain scans or laboratory tests in order to rule out other diseases.

At present, there is no cure for PD, but a variety of medications provide dramatic relief from the symptoms. Usually, affected individuals are given levodopa (L-DOPA; SINEMET™, PARCOPA™, ATAMET™, STALEVO™, MADOPAR™, and PROLOPA™) combined with carbidopa (LODOSYN™) (products containing a combination of levodopa and carbidopa include DUOPA® and RYTARY®). Carbidopa delays the conversion of levodopa into dopamine until it reaches the brain. Nerve cells can use levodopa to make dopamine and replenish the brain's dwindling supply. Although levodopa helps at least three-quarters of PD cases, not all symptoms respond equally to the drug. Bradykinesia and rigidity typically respond best, while tremor may be only marginally reduced. Problems with balance and other symptoms may not be alleviated at all. Anticholinergics may help control tremor and rigidity. Dopamine agonists, such as bromocriptine, pergolide, pramipexole, ropinirole, piribedil, cabergoline, apomorphine and lisuride, mimic the role of dopamine in the brain, causing the neurons to react as they would to dopamine. An antiviral drug, amantadine, also appears to reduce symptoms. In May 2006, the FDA approved rasagiline to be used along with levodopa for patients with advanced PD or as a single-drug treatment for early PD.

In some cases, surgery may be appropriate if the disease does not respond to drugs. A therapy called deep brain stimulation (DBS) has now been approved by the U.S. Food and Drug Administration. In DBS, electrodes are implanted into the brain and connected to a small electrical device called a pulse generator that can be externally programmed. DBS can reduce the need for levodopa and related drugs, which in turn decreases the involuntary movements called dyskinesias that are a common side effect of levodopa. It also helps to alleviate fluctuations of symptoms and to reduce tremors, slowness of movements, and gait problems. DBS requires careful programming of the stimulator device in order to work correctly.

There is a need in the art for a better understanding of the underlying disease mechanism and methods to facilitate the discovery of accurate biomarkers and therapeutic targets for Parkinson's disease.

SUMMARY OF THE DISCLOSURE

This disclosure demonstrates that network-based meta-analysis of four independent microarray studies provides a useful framework to identify candidate biomarkers, and that expression of highly ranked genes identified can be used as diagnostic and prognostic biomarkers for PD.

In one aspect, the disclosure provides a method for diagnosing, prognosing or monitoring Parkinson's Disease (PD) in a human subject, comprising: (a) obtaining a blood sample from a human subject suspected of having PD; (b) determining the expression level of at least one gene in the blood sample from the human subject suspected of having PD, wherein the at least one gene is selected from: HNF4A, THY1, SPEF1, SF3A2, SEMA6B, EN2, RTN3, BCAM, SPATA2L and TPSG1; and (c) comparing the expression level of the at least one gene expressed in the blood sample to the expression level of the at least one gene expressed in a non-PD, healthy control sample, whereby the increased expression level of the at least one gene expressed in the blood sample from the human subject suspected of having PD as compared to the non-PD sample is indicative of PD, thereby diagnosing the human subject as having PD.

In another aspect, the disclosure provides a method of treating a human subject for Parkinson's Disease (PD), the method comprising: (a) obtaining a diagnosis identifying a human subject as having PD, wherein the diagnosis was obtained by: (i) obtaining a blood sample from a human subject suspected of having PD; (ii) determining the expression level of at least one gene selected from: HNF4A, THY1, SPEF1, SF3A2, SEMA6B, EN2, RTN3, BCAM, SPATA2L and TPSG1; and (iii) comparing the expression level of the at least one gene expressed in the blood sample to the expression level of the at least one gene expressed in a non-PD, healthy control sample, whereby the increased expression level of the at least one gene expressed in the blood sample from the human subject suspected of having PD as compared to the non-PD sample is indicative of PD, thereby diagnosing the human subject as having PD; and (b) administering to the subject a PD treatment regimen.

In yet another aspect, the disclosure provides a Parkinson's Disease (PD) diagnosis, prognosis or monitoring kit, consisting of a set of probes suitable for the detection and quantification of the nucleic acid expression of at least one gene selected from: HNF4A, THY1, SPEF1, SF3A2, SEMA6B, EN2, RTN3, BCAM, SPATA2L and TPSG1.

In a second aspect, the disclosure provides a method for diagnosing, prognosing or monitoring Parkinson's Disease (PD) in a human subject, comprising: (a) obtaining a blood sample from a human subject suspected of having PD; (b) determining the expression level of at least one gene in the blood sample from the human subject suspected of having PD, wherein the at least one gene is selected from: PTBP1, SLC4A1, DAZAP2, EPB42, HELZ, SELENBP1, NUDT4, CA1, AHSP and ALAS2; and (c) comparing the expression level of the at least one gene expressed in the blood sample to the expression level of the at least one gene expressed in a non-PD, healthy control sample, whereby the decreased expression level of the at least one gene expressed in the blood sample from the human subject suspected of having PD as compared to the non-PD sample is indicative of PD, thereby diagnosing the human subject as having PD.

In another aspect, the disclosure provides a method of treating a human subject for Parkinson's Disease (PD), the method comprising: (a) obtaining a diagnosis identifying a human subject diagnosed as having PD, wherein the diagnosis was obtained by: (i) obtaining a blood sample from a human subject suspected of having PD; (ii) determining the expression level of at least one gene in the blood sample from the human subject suspected of having PD selected from: PTBP1, SLC4A1, DAZAP2, EPB42, HELZ, SELENBP1, NUDT4, CA1, AHSP and ALAS2; and (iii) comparing the expression level of the at least one gene expressed in the blood sample to the expression level of the at least one gene expressed in a non-PD, healthy control sample, whereby the decreased expression level of the at least one gene expressed in the blood sample from the human subject suspected of having PD as compared to the non-PD sample is indicative of PD, thereby diagnosing the human subject as having PD; and (b) administering to the subject a PD treatment regimen.

In yet another aspect, the disclosure provides a Parkinson's Disease (PD) diagnosis, prognosis or monitoring kit, consisting of a set of probes suitable for the detection and quantification of the nucleic acid expression of at least one gene: PTBP1, SLC4A1, DAZAP2, EPB42, HELZ, SELENBP1, NUDT4, CA1, AHSP and ALAS2.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

FIGS. 1A, 1B and 1C show the network-based and transcriptomic meta-analysis. FIG. 1A. Four independent microarray datasets were downloaded from the Gene Expression Ommibus (GEO) and preprocessed in INMEX where meta-analysis was undertaken using the Fisher's method. Datasets were subsequently uploaded into NetworkAnalyst to perform network and functional analysis and to identify key regulatory hub genes across the multiple microarray studies. Finally, the most significant genes were evaluated as biomakers for PD in blood samples obtained from two independent cohorts of patients. FIG. 1B. Venn diagram of differentially expressed genes identified from the meta-analysis (Meta-DE) and those from each individual microarray analysis (Individual-DE). FIG. 1C. Heat map representation of the top 50 differentially expressed genes across different microarrays identified from the meta-analysis (row-wise comparison). The heat map was re-scaled to prevent domination by study-specific effects. PD denotes Parkinson's disease and HC denotes healthy controls.

FIG. 2A. Zero-order interaction network of genes upregulated in blood of PD (Red). FIG. 2B. Zero-order interaction network of genes downregulated in blood of PD (Green).

FIGS. 3A, 3B, 3C and 3D show the evaluation of HNF4A and PTBP1 mRNAs as biomarkers for PD at baseline. FIG. 3A. Relative abundance of HNF4A mRNA in blood of PD patients (black circles) compared to HC (white circles) in samples from the PROBE cohort. FIG. 3B. Replication of biomarker expression in an independent set of samples from patients enrolled in the Harvard Biomarker Study (HBS) study. FIG. 3C. Relative abundance of PTBP1 mRNA in blood of PD patients compared to HC in samples from the PROBE cohort. FIG. 3D. Replication of PTBP1 mRNA expression in an independent set of samples from patients enrolled in the HBS study. Relative abundance of each biomarker was calculated using GAPDH as a reference gene and HC as calibrator. A student t-test (two-tailed) was used to estimate the significance between PD cases and controls. Post-hoc pair-wise comparisons were performed using a Tukey test of significance. Error bars represent 95% confidence intervals.

FIG. 4A. Pearson correlation analysis between HNF4A mRNA and PTBP1 mRNA in blood of PD patients (black circles) and HC (white circles) in samples from PROBE and HBS. FIG. 4B. Correlation analysis between HNF4A mRNA and Hoehn and Yahr scale in PD patients from both cohorts. Error bars represent 95% confidence intervals.

FIGS. 5A, 5B, 5C and 5D show the longitudinal performance of HNF4A and PTBP1 mRNAs in the HBS study. FIG. 5A. Individual trajectories for the relative abundance of HNF4A mRNA over time for HC (blue) and PD patients (red) in the HBS study. FIG. 5B. Average rate of HNF4A mRNA in PD patients compared to HC calculated via linear mixed effects regression analysis adjusting for sex, age and BMI. FIG. 5C. Individual trajectories for the relative abundance of PTBP1 mRNA over time for HC and PD patients. FIG. 5D. Average rate of PTBP1 mRNA expression in PD patients compared to HC calculated via linear mixed effects regression analysis. Red and blue lines denote PD and HC, respectively. T0 and T2 indicate baseline and 3 years follow up period, respectively. Post-hoc pair-wise comparisons were performed using a Tukey test of significance (**p=0.0001, *p=0.001). Error bars represent standard error.

FIGS. 7A and 7B show the dysregulated splicing factors in blood of PD. FIG. 7A. Upregulated splicing factors in blood of PD identified across the four microarray datasets. FIG. 7B. Downregulated splicing factors in blood of PD identified across the four microarray datasets.

FIG. 8A. ROC analysis to evaluate the performance of HNF4A mRNA as a diagnostic biomarker in samples from PROBE and HBS studies. FIG. 8B. ROC analysis to evaluate the performance of PTBP1 mRNA as a diagnostic biomarker in PROBE and HBS. FIG. 8C. ROC analysis combining HNF4A and PTBP1 mRNAs as diagnostic biomarkers in PROBE and HBS. AUC denotes area under the curve.

DETAILED DESCRIPTION OF THE DISCLOSURE

Figure 2A:
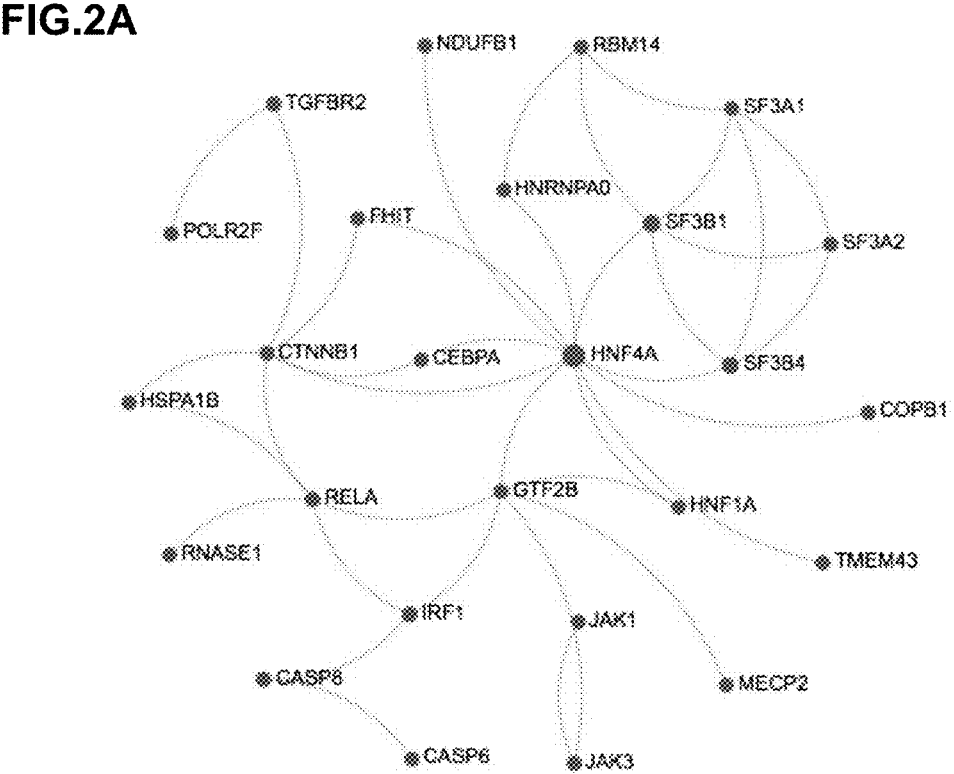
FIGS. 2A and 2B show the network analysis of differentially expressed genes in blood of PD.

The present disclosure demonstrates that network-based meta-analysis of four independent microarray studies provides a useful framework to identify candidate biomarkers, and that expression of highly ranked genes identified can be used as diagnostic and prognostic biomarkers for PD.

The development of therapeutic strategies for Parkinson's disease (PD) is hampered by the lack of reliable biomarkers to identify patients at early stages of the disease and track the therapeutic effect of potential drugs and neuroprotective agents. Readily accessible biomarkers capable of providing information about disease status are expected to accelerate this progress. Network-based meta-analysis identified promising blood biomarkers for recognizing early stage PD patients with high diagnostic accuracy. Longitudinal analysis demonstrated that HNF4A and PTBP1 are longitudinally dynamic biomarkers that provide insights into the molecular mechanisms underlying the altered insulin signaling in PD patients and may enable novel therapeutic strategies. Further, HNF4A was identified as a potential biomarker to monitor disease severity.

Substantial efforts have been devoted to the development of diagnostic strategies for PD. In particular, changes in mRNA from cellular whole blood can facilitate the identification of dysregulated processes and diagnostic biomarkers for PD. Several molecular signatures in blood have been identified. For example, 22 unique genes were found differentially expressed in blood of PD patients compared to healthy controls (Scherzer et al., (2007) Molecular markers of early Parkinson's disease based on gene expression in blood. *Proc Natl Acad Sci U.S.A* 104(3):955-960). Likewise, specific splice variants in blood were associated with PD in samples obtained from two independent clinical trials (Potashkin et al., (2012) Biosignatures for Parkinson's disease and atypical parkinsonian disorders patients. *PLoS One* 7(8):e43595, and Santiago et al., (2013) Specific splice variants are associated with Parkinson's disease. *Mov Disord* 28(12):1724-1727). In addition, altered expression of the vitamin D receptor (VDR) in blood and reduced plasma levels of 25-hydroxy vitamin $D_3$ have been associated with PD (Ding et al. (2013) Unrecognized vitamin D3 deficiency is common in Parkinson disease: Harvard Biomarker Study. *Neurology* 81(17):1531-1537). Furthermore, plasma levels of the epidermal growth factor (EGF) have been associated with cognitive decline in PD (Chen-Plotkin et al. (2011) Plasma epidermal growth factor levels predict cognitive decline in Parkinson disease. *Ann Neurol* 69(4):655-663).

Environmental stressors and genetic factors are most likely involved in the pathogenesis of PD. Among the genetic factors associated with PD, mutations in the gene encoding leucine-rich repeat kinase 2 (LRRK2) are the most common cause of autosomal dominant PD and a considerable risk factor in idiopathic forms of the disease. Given the complex interaction between environmental and genetic factors in sporadic PD, four independent microarray studies were integrated from patients harboring a mutation in the LRRK2 gene (G2019S; glycine to serine substitution at amino acid 2019), sporadic, and untreated PD patients in order to identify a universal signature in blood associated with PD. A transcriptomic and network-based meta-analysis was performed to identify key regulators and potential diagnostic biomarkers. This is a powerful approach to integrate gene expression data and to gain insight into complex diseases. The utility of network biology to identify biologically relevant biomarkers for neurodegenerative diseases has been demonstrated recently (Santiago & Potashkin (2014) A network approach to clinical intervention in neurodegenerative diseases. *Trends Mol Med* 20(12):694-703; Santiago & Potashkin (2013) Integrative network analysis unveils convergent molecular pathways in Parkinson's disease and diabetes. *PLoS One* 8(12):e83940; Santiago & Potashkin (2014) A network approach to diagnostic biomarkers in progressive supranuclear palsy. *Mov Disord* 29(4):550-555).

Network-based meta-analysis identified HNF4A and PTBP1, previously implicated in diabetes, as the most significant up and downregulated genes in blood of PD patients. These results were confirmed in blood samples from two independent clinical trials. Relative abundance of HNF4A mRNA correlated with disease severity in PD patients. Moreover, longitudinal analysis of HNF4A and PTBP1 revealed that their relative abundance changed over time indicating their potential use to track the clinical course of PD patients.

It should be understood that the embodiments described herein, are provided for explanatory purposes, and are not intended to be limiting.

All publications, patents and patent applications cited herein are hereby expressly incorporated by reference for all purposes to the extent they are consistent with this disclosure.

Methods well known to those skilled in the art can be used to construct expression vectors and recombinant bacterial cells according to this disclosure. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

In one aspect, the disclosure provides a method for diagnosing, prognosing or monitoring Parkinson's Disease (PD) in a human subject, comprising: (a) obtaining a blood sample from a human subject suspected of having PD; (b) determining the expression level of at least one gene in the blood sample from the human subject suspected of having PD, wherein the at least one gene is selected from: HNF4A, THY1, SPEF1, SF3A2, SEMA6B, EN2, RTN3, BCAM, SPATA2L and TPSG1; and (c) comparing the expression level of the at least one gene expressed in the blood sample to the expression level of the at least one gene expressed in a non-PD, healthy control sample, whereby the increased expression level of the at least one gene expressed in the blood sample from the human subject suspected of having PD as compared to the non-PD sample is indicative of PD, thereby diagnosing the human subject as having PD.

In another aspect, the disclosure provides a method of treating a human subject for Parkinson's Disease (PD), the method comprising: (a) obtaining a diagnosis identifying a human subject as having PD, wherein the diagnosis was obtained by: (i) obtaining a blood sample from a human subject suspected of having PD; (ii) determining the expression level of at least one gene selected from: HNF4A, THY1, SPEF1, SF3A2, SEMA6B, EN2, RTN3, BCAM, SPATA2L and TPSG1; and (iii) comparing the expression level of the at least one gene expressed in the blood sample to the expression level of the at least one gene expressed in a non-PD, healthy control sample, whereby the increased expression level of the at least one gene expressed in the blood sample from the human subject suspected of having PD as compared to the non-PD sample is indicative of PD, thereby diagnosing the human subject as having PD; and (b) administering to the subject a PD treatment regimen.

In an embodiment, the methods disclosed herein typically involve determining expression levels of at least one gene in a biological sample obtained from a human subject suspected of having PD. The methods may involve determining expression levels of at least 2, at least 3, at least 4, at least 5, at least 6, at least 7, at least 8, at least 9, at least 10, at least 20, at least 30, at least 40, at least 50, at least 60, at least 70, at least 80, at least 100, at least 200 or more genes in a biological sample obtained from an individual, wherein the genes are selected from: HNF4A, THY1, SPEF1, SF3A2, SEMA6B, EN2, RTN3, BCAM, SPATA2L and TPSG1; or the genes listed in Table 2 or Table 3.

In one embodiment, the at least one gene is HNF4A hepatocyte nuclear factor 4, alpha (official symbol: HNF4A; and official full name: hepatocyte nuclear factor 4, alpha; provided by HGNC). HNF4A is also known as: TCF; HNF4; MODY; FRTS4; MODY1; NR2A1; TCF14; HNF4a7; HNF4a8; HNF4a9; NR2A21; HNF4alpha. Nucleic acid accession number: >gi|385298689|ref|NM_000457.4| *Homo sapiens* hepatocyte nuclear factor 4, alpha (HNF4A), transcript variant 2, mRNA (SEQ ID NO: 07). Protein accession number: >gi|31077205|ref|NP_000448.3| *Homo sapiens* hepatocyte nuclear factor 4-alpha isoform HNF4alpha2 (SEQ ID NO: 08).

In another embodiment, the expression level is determined by detecting messenger RNA of the at least one gene. If mRNA is determined, then the method may further comprise reverse transcription of the messenger RNA prior to detecting. In an embodiment, determining the expression level of the at least one gene is by measuring a level of fluorescence by a sequence detection system following a quantitative, real-time polymerase chain reaction (PCR) assay.

In yet another embodiment, an increased HNF4A expression level of the human subject at a later time point compared to the HNF4A expression level at an initial time point or expression levels the same as a healthy control indicates an improved or steady prognosis of PD in the subject.

In a second aspect, the disclosure provides a method for diagnosing, prognosing or monitoring Parkinson's Disease (PD) in a human subject, comprising: (a) obtaining a blood sample from a human subject suspected of having PD; (b) determining the expression level of at least one gene in the blood sample from the human subject suspected of having PD, wherein the at least one gene is selected from: PTBP1, SLC4A1, DAZAP2, EPB42, HELZ, SELENBP1, NUDT4, CA1, AHSP and ALAS2; and (c) comparing the expression level of the at least one gene expressed in the blood sample to the expression level of the at least one gene expressed in a non-PD, healthy control sample, whereby the decreased expression level of the at least one gene expressed in the blood sample from the human subject suspected of having PD as compared to the non-PD sample is indicative of PD, thereby diagnosing the human subject as having PD.

In another aspect, the disclosure provides a method of treating a human subject for Parkinson's Disease (PD), the method comprising: (a) obtaining a diagnosis identifying a human subject diagnosed as having PD, wherein the diagnosis was obtained by: (i) obtaining a blood sample from a human subject suspected of having PD; (ii) determining the expression level of at least one gene in the blood sample from the human subject suspected of having PD selected from: PTBP1, SLC4A1, DAZAP2, EPB42, HELZ, SELENBP1, NUDT4, CA1, AHSP and ALAS2; and (iii) comparing the expression level of the at least one gene expressed in the blood sample to the expression level of the at least one gene expressed in a non-PD, healthy control sample, whereby the decreased expression level of the at least one gene expressed in the blood sample from the human subject suspected of having PD as compared to the non-PD sample is indicative of PD, thereby diagnosing the human subject as having PD; and (b) administering to the subject a PD treatment regimen.

In an embodiment, the methods disclosed herein typically involve determining expression levels of at least one gene in a biological sample obtained from a human subject suspected of having PD. The methods may involve determining expression levels of at least 2, at least 3, at least 4, at least 5, at least 6, at least 7, at least 8, at least 9, at least 10, at least 20, at least 30, at least 40, at least 50, at least 60, at least 70, at least 80, at least 100, at least 200 or more genes in a biological sample obtained from an individual, wherein the genes are selected from: PTBP1, SLC4A1, DAZAP2, EPB42, HELZ, SELENBP1, NUDT4, CA1, AHSP and ALAS2; or the genes listed in Table 2 or Table 3.

In one embodiment, the at least one gene is PTBP1 polypyrimidine tract binding protein 1 (official symbol: PTBP1; official full name: polypyrimidine tract binding protein 1; provided by HGNC). PTBP1 is also known as: PTB; PTB2; PTB3; PTB4; pPTB; HNRPI; PTB-1; PTB-T; HNRNPI; HNRNP-I). Nucleic acid accession number: >gi|209870087|ref|NM_002819.4| *Homo sapiens* polypyrimidine tract binding protein 1 (PTBP1), transcript variant 1, mRNA (SEQ ID NO: 09). Protein accession number: >gi|4506243|ref|NP_002810.1| *Homo sapiens* polypyrimidine tract-binding protein 1 isoform a (SEQ ID NO: 10).

In another embodiment, the expression level is determined by detecting messenger RNA of the at least one gene. If mRNA is determined, then the method may further comprise reverse transcription of the messenger RNA prior to detecting. In an embodiment, determining the expression level of the at least one gene is by measuring a level of fluorescence by a sequence detection system following a quantitative, real-time polymerase chain reaction (PCR) assay.

In yet another embodiment, an increased PTBP1 expression level of the human subject at a later time point compared to the PTBP1 expression level at an initial time point indicates a worse prognosis of PD in the subject. Furthermore, a decreased PTBP1 expression level of the human subject after treatment compared to the PTBP1 expression level prior to treatment or PTB1 expression levels similar to the healthy control sample indicates a better prognosis of PD in the subject.

As used herein, a "sample" is a biological sample isolated from a subject and can include, but is not limited to, whole blood, serum, plasma, blood cells, endothelial cells, tissue biopsies, lymphatic fluid, ascites fluid, interstitial fluid, bone marrow, cerebrospinal fluid (CSF), saliva, mucous, sputum, sweat, urine, or any other secretion, excretion, or other bodily fluids. A "blood sample" refers to whole blood or any fraction thereof, including blood cells, serum and plasma.

As used herein, the terms "diagnosis", "diagnostic", "diagnosing", refer to an identification of PD or to a predisposition of developing PD, based on a detection of at least one gene. The terms "prognosis", "prognostic", "prognosing", refer to the ability of predicting, forecasting or correlating a given detection or measurement with a future outcome of PD in the patient (e.g., severity, likelihood of successfully treating, or survival). The disclosure also relates to monitoring the influence of agents, treatments or therapies for PD (e.g., drugs, compounds). As used herein, "monitoring" refers to determining the regression, progression, course and/or onset of, and/or prognoses of PD before any treatment or during treatment in order to assess the PD patient's improvement or lack thereof over time.

As used herein, the term "control sample" or "healthy control" refers to a sample from a subject that does not have PD or subject that does not have PD. In a particular embodiment, the control sample or healthy control does not have PD or is indicative of the absence of PD. Control samples can be obtained from patients/individuals not afflicted with PD. Other types of control samples may also be used. In a related facet, a control reaction may be designed to control the method itself (e.g., cell extraction, the capture, the amplification reaction or detection method, number of cells present in the sample, a combination thereof or any step which could be monitored to positively validate that the absence of a signal (e.g., the expression level of a gene) is not the result of a defect in one or more of the steps). Once a cut-off value is determined, a control sample giving a signal characteristic of the predetermined cut-off value can also be designed and used in the methods of the present invention. Diagnosis/prognosis tests are commonly characterized by the following 4 performance indicators: sensitivity (Se), specificity (Sp), positive predictive value (PPV), and negative predictive value (NPV).

As used herein, the terms "nucleic acid", "polynucleotide", "nucleotide", and "oligonucleotide" can be used interchangeably to refer to single stranded or double stranded, nucleic acid comprising DNA, RNA, derivatives thereof, or combinations thereof.

Expression of the genes disclosed herein can be measured at the RNA level using any method known in the art. For example, expression can be measured using Real-Time PCR assays (RT-PCR), e.g., using primers specific for the differentially expressed sequences. As used herein, the term "real-time PCR" (also called quantitative real-time polymerase chain reaction) refers to a method for the detection and quantitation of an amplified PCR product based on incorporation of a fluorescent reporter dye; the fluorescent signal increases in direct proportion to the amount of PCR product produced and is monitored at each cycle, 'in real-time', such that the time point at which the first significant increase in the amount of PCR product correlates with the initial amount of target template. In one embodiment, real-time PCR can be preceded by reverse-transcription of the messenger RNA. RNA can also be quantified using, for example, other target amplification methods (e.g., TMA, SDA, NASBA), or signal amplification methods (e.g., bDNA). Alternatively, northern hybridization analysis using probes which specifically recognize one or more of the sequences or each gene can be used to determine gene expression.

The difference in the level of biomarker between normal and abnormal is preferably statistically significant and may be an increase in biomarker expression level or a decrease in biomarker expression level, and without any limitation of the method, achieving statistical significance, and thus the preferred analytical and clinical accuracy, generally but not always requires that combinations of several biomarkers be used together in panels and combined with mathematical algorithms in order to achieve a statistically significant biomarker index.

As used herein, the term "primer set" or "primers" refers to a pair of PCR primers that include a forward primer and reverse primer used in a PCR reaction and allows the generation of an amplicon. Numerous primers used in the context of the present disclosure can be readily determined by a person of ordinary skill in the art to which the present invention pertains. Non-limiting examples of primers are shown in SEQ ID NO: 3-6. A person skilled in the art can design numerous other primers based on the teachings herein and the common general knowledge. As used herein, the term "probes" refers to a nucleic acid molecule which typically ranges in size from about 8 nucleotides to several hundred nucleotides in length. Such a molecule is typically used to identify a target nucleic acid sequence in a sample by hybridizing to such target nucleic acid sequence under stringent hybridization conditions. Generally, an oligonucleotide useful as a probe or primer that selectively hybridizes to a selected nucleotide sequence is at least about 15 nucleotides in length, usually at least about 18 nucleotides, and particularly about 21 nucleotides in length or more in length. Primer and probe design software programs are also commercially available, including without limitation, Primer Detective (ClonTech, Palo Alto, Calif.), Lasergene, (DNASTAR, Inc., Madison, Wis.); and Oligo software (National Biosciences, Inc., Plymouth, Minn.) and iOligo (Caesar Software, Portsmouth, N.H.).

As used herein, a "sequence detection system" is any computational method in the art that can be used to analyze the results of a PCR reaction. One example is the Applied Biosystems HT7900 fast Real-Time PCR system. In certain embodiments, gene expression can be analyzed using, e.g., direct DNA expression in microarray, Sanger sequencing analysis, Northern blot, the Nanostring® technology, serial analysis of gene expression (SAGE), RNA-seq, tissue microarray, or protein expression with immunohistochemistry or western blot technique.

In an embodiment, the methods disclosed here further comprise determining a treatment regimen for the human subject. The methods could be used to generate a prescription treatment to treat, delay development or prevent progression of PD in an individual identified by the methods disclose herein as having PD. Furthermore, the method disclosed herein to adapt the correct or most appropriate treatment regimen and/or monitor the patient response to therapy.

In yet another aspect, the disclosure provides a Parkinson's Disease (PD) diagnosis, prognosis or monitoring kit, consisting of a set of probes suitable for the detection and quantification of the nucleic acid expression of at least one gene selected from: HNF4A, THY1, SPEF1, SF3A2, SEMA6B, EN2, RTN3, BCAM, SPATA2L and TPSG1. In another aspect, the disclosure provides a Parkinson's Disease (PD) diagnosis, prognosis or monitoring kit, consisting of a set of probes suitable for the detection and quantification of the nucleic acid expression of at least one gene: PTBP1, SLC4A1, DAZAP2, EPB42, HELZ, SELENBP1, NUDT4, CA1, AHSP and ALAS2.

In an embodiment, the present disclosure also relates to kits containing nucleic acid primers and kits containing nucleic acid primers and nucleic acid probes to diagnose and prognose PD in a sample of human thought to be afflicted with PD or known to be afflicted with PD. Such kit generally comprises a first container means having at least one oligonucleotide probe and/or primer that hybridizes to a target nucleic acid (e.g., HNF4A or PTBP1 RNA) and a second container means containing at least one other oligonucleotide primer and/or probe that hybridizes to the above-mentioned nucleic acid specific sequences. The kit may further include other containers comprising additional components such as an additional oligonucleotide or primer and/or one or more of the following: buffers, reagents to be used in the assay (e.g., wash reagents, polymerases, internal controls or else) and reagents capable of detecting the presence of bound nucleic acid probe(s)/primer(s). Numerous embodiments of the kits of the present invention are possible. For example, the different container means can be divided in amplifying reagents and detection reagents. In addition, the kits may further include instructions for practicing the diagnostic and/or prognostic methods of the present disclosure. Such instructions can concern details relating to the experimental protocol as well as to the cut-off values for the PD specific biomarker ratio that may be used.

EXAMPLES

Methods
Microarray Meta-Analysis

Gene expression data from microarrays studies was downloaded from the Gene Expression Omnibus (GEO) and GEMMA database (Zoubarev et al. (2012) Gemma: a resource for the reuse, sharing and meta-analysis of expression profiling data. *Bioinformatics* 28(17):2272-2273) by using the terms "Parkinson's disease" and "blood" or "transcriptional profiling" as of May 31, 2014. Microarray studies using RNA prepared from human blood with 10 samples or more were included in the study. Only samples from PD patients and healthy controls were analyzed. A total of four microarray studies met the inclusion criteria and were considered for subsequent analysis. The microarray studies analyzed in this study are listed in Table 1. GSE6613 included 50 predominantly early stage sporadic PD patients with a mean Hoehn and Yahr stage of 2.3 from which nine were untreated patients and 22 age and sex matched healthy controls. GSE8838 included 18 sporadic PD patients treated with different PD medications and 12 HC. GSE22491 included 10 PD patients carrying a LRRK2 mutation from which one patient was untreated and seven HC. GSE54536 included 5 untreated PD patients and 5 HC. A microarray meta-analysis was conducted using the Integrative Meta-Analysis of Expression Data (INMEX; Xia et al. (2013) INMEX—a web-based tool for integrative meta-analysis of expression data. *Nucleic Acids Res* 41(Web Server issue): W63-70) in accordance with the PRISMA guidelines for meta-analysis (Moher et al., (2009) Preferred reporting items for systematic reviews and meta-analyses: the PRISMA statement. *PLoS Med* 6(7):e1000097). All gene probes were converted to a common Entrez ID using the gene/probe conversion tool in INMEX. After matching all probes to a common Entrez ID, all datasets were preprocessed using the $log_2$-transformation and quantile normalization. Each individual dataset was visualized in box-plots to ensure identical distribution among the samples. Differential expression analysis was performed with INMEX for each dataset independently using a false discovery rate (FDR) of 0.05, a significance of p<0.05 and moderated t-test based on the Limma algorithm. In INMEX, the results from individual microarray dataset analyses are only for reference comparison and not required for meta-analysis in the subsequent steps. After microarray preprocessing steps, a data integrity check was performed before proceeding to the meta-analysis. For meta-analysis, the Fisher's method was used with a significance level of p<0.05 to combine p-values from the multiple datasets. Fisher's method is a widely used statistical approach in meta-analysis to combine p-values from different studies independently of the sample size (Xia et al. (2013) INMEX—a web-based tool for integrative meta-analysis of expression data. *Nucleic Acids Res* 41(Web Server issue):W63-70; Tseng et al., (2012) Comprehensive literature review and statistical considerations for microarray meta-analysis. *Nucleic Acids Res* 40(9):3785-3799). Gene ontology and functional analysis was performed using NetworkAnalyst (Xia et al., (2014) NetworkAnalyst—integrative approaches for protein-protein interaction network analysis and visual exploration. *Nucleic Acids Res* 42(Web Server issue):W167-74. Epub May 26, 2014).

TABLE 1

Microarray studies in blood used for meta-analysis.

| GEO accession number | No. of samples | Description | Platform | Ref. |
|---|---|---|---|---|
| GSE6613 | PD = 50; HC = 22 | Early stage sporadic PD patients (mean Hoehn and Yahr = 2.3) | Affymetrix Human Genome U133A | 1 |
| GSE18838 | PD = 18; HC = 12 | Sporadic PD patients (treated) | Affymetrix Exon Arrays | 2 |
| GSE22491 | PD = 10; HC = 7 | (G2019S) LRRK2 mutation carriers with PD | Agilent Whole Human Genome | 3 |
| GSE54536 | PD = 5; HC = 5 | Untreated sporadic PD Patients (mean Hoehn and Yahr stage = 1) | Ilumina HT-12 V4 | 4 |

1 - Scherzer et al. (2007) Molecular markers of early Parkinson's disease based on gene expression in blood. *Proc Natl Acad Sci U.S.A.* 104(3): 955-960.
2 - Shehadeh et al. (2010) SRRM2, a potential blood biomarker revealing high alternative splicing in Parkinson's disease. *PLoS One* 5(2): e9104.
3 - Mutez et al. (2011) Transcriptional profile of Parkinson blood mononuclear cells with LRRK2 mutation. *Neurobiol Aging* 32(10): 1839-1848.
4 - Alieva et al. (2014) Involvement of endocytosis and alternative splicing in the formation of the pathological process in the early stages of Parkinson's disease. *Biomed Res Int* 2014: 718732.

Network-Based Meta-Analysis

Network-based meta-analysis was performed using NetworkAnalyst (Xia et al., (2014) NetworkAnalyst—integrative approaches for protein-protein interaction network analysis and visual exploration. *Nucleic Acids Res* 42(Web Server issue):W167-74. Epub May 26, 2014). Microarray datasets were processed as described above. Briefly, microarray datasets were preprocessed by a $log_2$ transformation followed by quantile normalization. Duplicate genes were replaced by their mean value. A significance value of p<0.05 and a $log_2$ fold change of 1 were used as a cut-off value. Network construction was restricted to contain only the original seed proteins.

Information about Study Participants

The Institutional Review Boards of Rosalind Franklin University of Medicine and Science approved the study protocol. Written informed consent was received from all participants. Clinical characteristics of the participants used in this study have been reported elsewhere in (Potashkin et al., (2012) Biosignatures for Parkinson's disease and atypical parkinsonian disorders patients. *PLoS One* 7(8):e43595; Santiago et al., (2013) Specific splice variants are associated with Parkinson's disease. *Mov Disord* 28(12):1724-1727; and Santiago & Potashkin (2013) Integrative network analysis unveils convergent molecular pathways in Parkinson's disease and diabetes. *PLoS One* 8(12):e83940. Briefly, 51 PD patients (29 men, 22 women; mean age at enrollment 63.16±6.42; Hoehn and Yahr scale 2±0.28) and 45 healthy age-matched controls (24 male, 21 women; mean age at enrollment 65.12±8.60) enrolled in the Diagnostic and Prognostic Biomarkers for Parkinson's Disease (PROBE) (#NCT00653783). Clinical diagnosis of PD was based on the United Kingdom Parkinson's Disease Society Brain Bank criteria. Healthy individuals had no history of neurological disease and a Mini-Mental State Examination (MMSE) test score higher than 27. Inclusion and exclusion criteria for patients enrolled in the PROBE study have been reported in Potashkin et al., (2012) Biosignatures for Parkinson's disease and atypical parkinsonian disorders patients. *PLoS One* 7(8):e43595. As an independent replication cohort of patients 96 individuals were used, including 50 PD patients (31 men, 19 women; Hoehn and Yahr scale 1.97±0.62; mean age at enrollment 63.12±8.96; mean age at onset 58.75±10.17) and 46 healthy age-matched controls (26 men, 20 women; mean age at enrollment 64.28±10.42) enrolled in the Harvard Biomarker Study (HBS). Three years follow-up samples from cases and controls enrolled in the HBS were collected and analyzed in this study. Diagnosis of cases and controls was assessed at each visit to ensure high diagnostic accuracy. Additional information about the participants enrolled in the HBS clinical trial has been published previously Ding et al. (2011) Association of SNCA with Parkinson: replication in the Harvard Neuro-Discovery Center Biomarker Study. *Mov Disord* 26(12): 2283-2286.

Quantitative Real Time Polymerase Chain Reactions

Blood was collected and prepared as described using the PAXgene Blood RNA system (Qiagen, Valencia, Calif., USA) (Scherzer et al. (2007) Molecular markers of early Parkinson's disease based on gene expression in blood. *Proc Natl Acad Sci U.S.A.* 104(3):955-960; and Potashkin et al., (2012) Biosignatures for Parkinson's disease and atypical parkinsonian disorders patients. *PLoS One* 7(8):e43595). Samples with RNA integrity values >7.0 and ratio of absorbances at 260/280 nm between 1.7 and 2.4 were used in the current study. A total of 1 µg of RNA was reversed transcribed using the High Capacity RNA transcription kit (Life Technologies, Carlsbad, Calif., USA). Primers were designed using Primer Express software and ordered (Life Technologies, Carlsbad, Calif., USA). The primer sequences used in this study are as follows:

```
GAPDH forward:
                                    (SEQ ID NO: 01)
5'-CAACGGATTTGGTCGTATTGG-3';

GAPDH reverse:
                                    (SEQ ID NO: 02)
5'-TGATGGCAACAATATCCACTTTACC-3', HNF4A forward:
                                    (SEQ ID NO: 03)
5'-CAGAATGAGCGGGACCGGATC-3';

HNF4A reverse:
                                    (SEQ ID NO: 04)
5'-CAGCAGCTGCTCCTTCATGGAC-3', PTBP1 forward:
                                    (SEQ ID NO: 05)
5'-GCTCAGGATCATCGTGGAGAA-3';

PTBP1 reverse:
                                    (SEQ ID NO: 06)
5'-ATCTTCAACACTGTGCCGAACTT-3'.
```

Quantitative PCR assays were carried using 25 µl reactions containing Power SYBR Green master mix (Life Technologies, Carlsbad, Calif., USA), primer at a concentration of 5 µM and nuclease free water. PCR reactions were amplified using a DNA engine Opticon 2 Analyzer (Bio-Rad Life Sciences, Hercules, Calif., USA). Amplification conditions and detailed description of qPCR experiments are reported elsewhere in Potashkin et al., (2012) Biosignatures for Parkinson's disease and atypical parkinsonian disorders patients. *PLoS One* 7(8):e43595; and Santiago et al., (2013) Specific splice variants are associated with Parkinson's disease. *Mov Disord* 28(12):1724-1727).

Statistical Analysis

Network-based microarray meta-analysis was performed using INMEX and NetworkAnalyst. A student t-test (two-tailed) was used to estimate the significance between PD cases and controls for numerical variables. Post-hoc pairwise comparisons were performed using a Tukey test. Pearson correlation analysis was used to determine statistical significance for HNF4A and PTBP1 adjusting for sex, age, Hoehn and Yahr scale in both cohorts and BMI in the HBS study. A ROC curve analysis was used to evaluate the diagnostic accuracy. A step-wise linear discriminant analysis was performed to determine the sensitivity and specificity values for the linear combination of both biomarkers. Power analyses of completed experiments were performed to demonstrate that the sample size used in this study allowed the detection of a difference of 0.5 in fold change with a power of 99% and a significance of 0.05. A p-value less than 0.05 was regarded statistically significant. For the longitudinal analysis we used a linear mixed effects regression model including subjects as random effects and adjusting for sex, age and BMI. Longitudinal data was analyzed using SuperMix (Scientific Software International Inc., IL, USA) and Statistica 12 (StatSoft Inc., OK, USA). All other statistical analyses were undertaken using Prism4.0 (GraphPad, CA, USA).

Example 1

Meta-Analysis of Blood Microarrays in PD

In order to identify a common transcriptional signature in blood of PD patients, four microarray studies (Table 1) were analyzed using INMEX, a web interface for the integrative meta-analysis. The overall meta-analysis workflow used in this study is shown in FIG. 1A. Meta-analysis using a Fisher's test identified a total of 2,781 genes differentially expressed consistently across four microarray studies. Among this group, 680 genes were upregulated and 2,101 were downregulated in PD compared to healthy controls. The thy-1 cell surface antigen (THY1) and HNF4A were the most significant upregulated genes across the four microarray datasets. The top ten upregulated and downregulated genes are listed in Table 2. The complete list of differentially expressed genes is provided in Table 3. There were 921 gained genes uniquely identified in the meta-analysis that show relatively weak, but consistent expression across the four datasets. A total of 491 genes were classified as lost genes (i.e., genes identified as differentially expressed genes in individual datasets but not in the meta-analysis). Venn diagram of meta-analysis results is shown in FIG. 1B and heat map visualization of the top 50 genes across the different studies is displayed in FIG. 1C.

TABLE 2

Top 10 upregulated and downregulated genes in PD identified by meta-analysis.

| Entrez ID | Gene Symbol | Combined Tstat | Combined P-value |
|---|---|---|---|
| Upregulated genes | | | |
| 7070 | THY1 | 74.145 | 5.46E-09 |
| 3172 | HNF4A | 66.421 | 8.49E-08 |
| 25876 | SPEF1 | 65.538 | 8.49E-08 |
| 8175 | SF3A2 | 65.127 | 8.49E-08 |
| 10501 | SEMA6B | 61.057 | 4.23E-07 |
| 2020 | EN2 | 60.476 | 4.23E-07 |
| 10313 | RTN3 | 60.224 | 4.23E-07 |
| 4059 | BCAM | 60.06 | 4.23E-07 |
| 124044 | SPATA2L | 59.655 | 4.51E-07 |
| 25823 | TPSG1 | 59.018 | 5.41E-07 |
| Downregulated genes | | | |
| 5725 | PTBP1 | -58.731 | 5.60E-07 |
| 6521 | SLC4A1 | -58.117 | 6.77E-07 |
| 9802 | DAZAP2 | -56.939 | 9.20E-07 |
| 2038 | EPB42 | -55.377 | 1.39E-06 |
| 9931 | HELZ | -54.311 | 1.83E-06 |
| 8991 | SELENBP1 | -54.268 | 1.83E-06 |
| 11163 | NUDT4 | -53.277 | 2.54E-06 |
| 759 | CA1 | -52.77 | 2.97E-06 |
| 51327 | AHSP | -52.673 | 3.00E-06 |
| 212 | ALAS2 | -52.324 | 3.40E-06 |

TABLE 3

Complete list of differentially expressed genes.

| Entrez ID | Gene symbol (Name) | Combined Tstat | Combined Pval |
|---|---|---|---|
| Upregulated genes | | | |
| 7070 | THY1 | 74.145 | 5.46E-09 |
| 3172 | HNF4A | 66.421 | 8.49E-08 |
| 25876 | SPEF1 | 65.538 | 8.49E-08 |
| 8175 | SF3A2 | 65.127 | 8.49E-08 |
| 10501 | SEMA6B | 61.057 | 4.23E-07 |
| 2020 | EN2 | 60.476 | 4.23E-07 |
| 10313 | RTN3 | 60.224 | 4.23E-07 |
| 4059 | BCAM | 60.06 | 4.23E-07 |
| 124044 | SPATA2L | 59.655 | 4.51E-07 |
| 25823 | TPSG1 | 59.018 | 5.41E-07 |
| 1584 | CYP11B1 | 57.882 | 6.95E-07 |
| 1152 | CKB | 57.629 | 7.23E-07 |
| 23546 | SYNGR4 | 56.785 | 9.24E-07 |
| 8911 | CACNA1I | 56.141 | 1.15E-06 |
| 777 | CACNA1E | 56.031 | 1.15E-06 |
| 4209 | MEF2D | 55.754 | 1.24E-06 |
| 6601 | SMARCC2 | 54.901 | 1.59E-06 |
| 5430 | POLR2A | 54.861 | 1.59E-06 |
| 5586 | PKN2 | 54.471 | 1.81E-06 |
| 2272 | FHIT | 53.787 | 2.18E-06 |
| 23038 | WDTC1 | 53.556 | 2.32E-06 |
| 168544 | ZNF467 | 53.135 | 2.61E-06 |
| 64067 | NPAS3 | 52.247 | 3.41E-06 |
| 23492 | CBX7 | 51.876 | 3.63E-06 |
| 60506 | NYX | 51.846 | 3.63E-06 |
| 115703 | ARHGAP33 | 50.931 | 5.09E-06 |
| 4654 | MYOD1 | 50.909 | 5.09E-06 |
| 64405 | CDH22 | 50.434 | 6.13E-06 |
| 81693 | AMN | 49.975 | 7.16E-06 |
| 354 | KLK3 | 49.809 | 7.37E-06 |
| 150094 | SIK1 | 49.518 | 8.20E-06 |
| 7356 | SCGB1A1 | 49.43 | 8.34E-06 |
| 51286 | CEND1 | 48.614 | 1.09E-05 |
| 63940 | GPSM3 | 48.45 | 1.14E-05 |
| 6369 | CCL24 | 48.292 | 1.20E-05 |
| 387509 | GPR153 | 48.183 | 1.24E-05 |
| 9653 | HS2ST1 | 47.727 | 1.46E-05 |
| 54345 | SOX18 | 47.623 | 1.47E-05 |
| 5024 | P2RX3 | 47.149 | 1.73E-05 |
| 401 | PHOX2A | 46.83 | 1.96E-05 |
| 1628 | DBP | 46.744 | 2.00E-05 |
| 2128 | EVX1 | 46.565 | 2.07E-05 |
| 64321 | SOX17 | 46.262 | 2.23E-05 |
| 80023 | NRSN2 | 46.259 | 2.23E-05 |
| 8433 | UTF1 | 46.034 | 2.42E-05 |
| 23373 | CRTC1 | 46.008 | 2.42E-05 |
| 55653 | BCAS4 | 45.925 | 2.47E-05 |
| 1762 | DMWD | 45.88 | 2.49E-05 |
| 3837 | KPNB1 | 45.792 | 2.55E-05 |
| 4326 | MMP17 | 45.133 | 3.21E-05 |
| 57030 | SLC17A7 | 45.124 | 3.21E-05 |
| 1339 | COX6A2 | 44.443 | 4.12E-05 |
| 2696 | GIPR | 44.103 | 4.61E-05 |
| 920 | CD4 | 43.975 | 4.81E-05 |
| 51299 | NRN1 | 43.693 | 5.17E-05 |
| 79729 | SH3D21 | 43.542 | 5.39E-05 |
| 399664 | MEX3D | 43.392 | 5.70E-05 |
| 2786 | GNG4 | 43.049 | 6.11E-05 |
| 1137 | CHRNA4 | 43.02 | 6.13E-05 |
| 80758 | PRR7 | 42.981 | 6.17E-05 |
| 1822 | ATN1 | 42.113 | 8.32E-05 |
| 551 | AVP | 42.078 | 8.33E-05 |
| 27113 | BBC3 | 41.902 | 8.71E-05 |
| 784 | CACNB3 | 41.779 | 9.04E-05 |
| 27023 | FOXB1 | 41.622 | 9.46E-05 |
| 7475 | WNT6 | 41.387 | 0.0001018 |
| 10522 | DEAF1 | 41.373 | 0.0001018 |
| 3060 | HCRT | 41.197 | 0.00010816 |
| 80128 | TRIM46 | 41.131 | 0.00011046 |
| 84656 | GLYR1 | 40.668 | 0.00013086 |
| 26145 | IRF2BP1 | 40.603 | 0.00013319 |
| 10297 | APC2 | 40.544 | 0.00013508 |
| 50488 | MINK1 | 40.283 | 0.00014694 |
| 6927 | HNF1A | 39.781 | 0.00016912 |
| 359 | AQP2 | 39.487 | 0.00018366 |
| 1395 | CRHR2 | 39.292 | 0.00019407 |
| 25907 | TMEM158 | 39.288 | 0.00019407 |
| 8545 | CGGBP1 | 39.045 | 0.0002117 |
| 90993 | CREB3L1 | 38.752 | 0.00022835 |
| 2625 | GATA3 | 38.423 | 0.00024799 |
| 3200 | HOXA3 | 38.296 | 0.00025907 |
| 64840 | PORCN | 38.05 | 0.00027866 |
| 79870 | BAALC | 38.048 | 0.00027866 |
| 8484 | GALR3 | 38.04 | 0.00027866 |
| 79812 | MMRN2 | 37.868 | 0.00029769 |
| 79080 | CCDC86 | 37.806 | 0.00030175 |
| 226 | ALDOA | 36.95 | 0.00040211 |
| 51085 | MLXIPL | 36.696 | 0.00042987 |
| 9344 | TAOK2 | 36.556 | 0.00044836 |
| 2959 | GTF2B | 36.481 | 0.00045294 |
| 6524 | SLC5A2 | 36.481 | 0.00045294 |
| 79269 | DCAF10 | 36.384 | 0.00046395 |
| 26000 | TBC1D10B | 36.285 | 0.00048023 |
| 775 | CACNA1C | 36.244 | 0.00048419 |
| 54972 | TMEM132A | 36.216 | 0.00048779 |
| 5301 | PIN1P1 | 35.991 | 0.00052147 |
| 1997 | ELF1 | 35.979 | 0.00052201 |
| 79777 | ACBD4 | 35.938 | 0.00052703 |
| 8739 | HRK | 35.915 | 0.00053013 |
| 9330 | GTF3C3 | 35.746 | 0.0005604 |

TABLE 3-continued

Complete list of differentially expressed genes.

| Entrez ID | Gene symbol (Name) | Combined Tstat | Combined Pval |
|---|---|---|---|
| 1727 | CYB5R3 | 35.48 | 0.0006149 |
| 4150 | MAZ | 35.433 | 0.00061837 |
| 4037 | LRP3 | 35.344 | 0.00063441 |
| 56882 | CDC42SE1 | 35.241 | 0.00065511 |
| 80004 | ESRP2 | 35.153 | 0.00067249 |
| 5305 | PIP4K2A | 35.048 | 0.00069365 |
| 51230 | PHF20 | 35.045 | 0.00069365 |
| 11011 | TLK2 | 35.02 | 0.00069861 |
| 27344 | PCSK1N | 34.974 | 0.00070972 |
| 7841 | MOGS | 34.946 | 0.00071307 |
| 23295 | MGRN1 | 34.874 | 0.00072598 |
| 10671 | DCTN6 | 34.871 | 0.00072598 |
| 3891 | KRT85 | 34.644 | 0.00077757 |
| 392 | ARHGAP1 | 34.633 | 0.00077767 |
| 10195 | ALG3 | 34.452 | 0.00081204 |
| 8546 | AP3B1 | 34.446 | 0.00081204 |
| 11054 | OGFR | 34.422 | 0.0008139 |
| 90864 | SPSB3 | 34.396 | 0.00081501 |
| 51647 | FAM96B | 34.252 | 0.00085147 |
| 5020 | OXT | 34.231 | 0.00085147 |
| 10814 | CPLX2 | 34.223 | 0.00085168 |
| 79882 | ZC3H14 | 34.141 | 0.00087342 |
| 51367 | POP5 | 34.138 | 0.00087342 |
| 575 | BAI1 | 34.084 | 0.00088085 |
| 4342 | MOS | 34.084 | 0.00088085 |
| 6640 | SNTA1 | 34.076 | 0.0008812 |
| 4762 | NEUROG1 | 34.068 | 0.0008812 |
| 3846 | KRTAP5-9 | 34.039 | 0.00088679 |
| 79173 | C19orf57 | 34.001 | 0.0008962 |
| 55146 | ZDHHC4 | 33.857 | 0.00093452 |
| 79575 | ABHD8 | 33.794 | 0.00094852 |
| 1314 | COPA | 33.65 | 0.00099726 |
| 3716 | JAK1 | 33.646 | 0.00099726 |
| 79958 | DENND1C | 33.569 | 0.0010154 |
| 27076 | LYPD3 | 33.267 | 0.0011188 |
| 3292 | HSD17B1 | 33.21 | 0.0011406 |
| 9780 | PIEZO1 | 33.199 | 0.0011427 |
| 6688 | SPI1 | 33.135 | 0.0011671 |
| 374291 | NDUFS7 | 33.105 | 0.0011787 |
| 8398 | PLA2G6 | 33.071 | 0.0011922 |
| 8360 | HIST1H4D | 33.055 | 0.0011939 |
| 6658 | SOX3 | 32.965 | 0.0012244 |
| 64771 | C6orf106 | 32.899 | 0.0012372 |
| 147694 | ZNF548 | 32.824 | 0.0012651 |
| 23173 | METAP1 | 32.797 | 0.0012678 |
| 4504 | MT3 | 32.733 | 0.0012794 |
| 23185 | LARP4B | 32.726 | 0.0012797 |
| 11166 | SOX21 | 32.577 | 0.0013308 |
| 1050 | CEBPA | 32.483 | 0.0013672 |
| 56928 | SPPL2B | 32.475 | 0.0013688 |
| 7182 | NR2C2 | 32.438 | 0.0013746 |
| 23396 | PIP5K1C | 32.389 | 0.001395 |
| 79094 | CHAC1 | 32.193 | 0.0014881 |
| 23593 | HEBP2 | 31.923 | 0.0016257 |
| 170680 | PSORS1C2 | 31.726 | 0.0017164 |
| 5920 | RARRES3 | 31.651 | 0.0017505 |
| 7425 | VGF | 31.626 | 0.0017612 |
| 1813 | DRD2 | 31.617 | 0.0017642 |
| 1315 | COPB1 | 31.521 | 0.0018072 |
| 7517 | XRCC3 | 31.486 | 0.001813 |
| 2622 | GAS8 | 31.484 | 0.001813 |
| 1857 | DVL3 | 31.43 | 0.0018298 |
| 79927 | FAM110D | 31.389 | 0.0018453 |
| 9048 | ARTN | 31.38 | 0.0018479 |
| 11230 | PRAF2 | 31.264 | 0.0019146 |
| 10730 | YME1L1 | 31.242 | 0.0019284 |
| 9230 | RAB11B | 30.921 | 0.0021132 |
| 1849 | DUSP7 | 30.857 | 0.0021566 |
| 9112 | MTA1 | 30.812 | 0.0021859 |
| 6775 | STAT4 | 30.75 | 0.0022299 |
| 7005 | TEAD3 | 30.708 | 0.0022534 |
| 8506 | CNTNAP1 | 30.595 | 0.0023331 |
| 54954 | FAM120C | 30.575 | 0.0023458 |
| 6199 | RPS6KB2 | 30.556 | 0.0023566 |
| 23580 | CDC42EP4 | 30.531 | 0.0023635 |
| 56156 | TEX13B | 30.513 | 0.0023769 |
| 1376 | CPT2 | 30.49 | 0.0023901 |
| 6490 | PMEL | 30.446 | 0.0024202 |
| 55262 | C7orf43 | 30.356 | 0.0024695 |
| 11155 | LDB3 | 30.319 | 0.002498 |
| 11346 | SYNPO | 30.176 | 0.0026062 |
| 10861 | SLC26A1 | 30.064 | 0.002703 |
| 54531 | MIER2 | 29.945 | 0.0028074 |
| 221037 | JMJD1C | 29.753 | 0.0029788 |
| 64061 | TSPYL2 | 29.545 | 0.003156 |
| 22976 | PAXIP1 | 29.51 | 0.0031791 |
| 10401 | PIAS3 | 29.489 | 0.0031941 |
| 26088 | GGA1 | 29.478 | 0.0031993 |
| 10206 | TRIM13 | 29.465 | 0.0032112 |
| 10935 | PRDX3 | 29.41 | 0.0032568 |
| 56981 | PRDM11 | 29.278 | 0.0034075 |
| 916 | CD3E | 29.264 | 0.0034213 |
| 64130 | LIN7B | 29.142 | 0.0035598 |
| 83737 | ITCH | 29.098 | 0.0036012 |
| 51380 | CSAD | 29.075 | 0.0036231 |
| 9640 | ZNF592 | 29.05 | 0.003638 |
| 861 | RUNX1 | 29.047 | 0.003638 |
| 57446 | NDRG3 | 29.027 | 0.0036544 |
| 22859 | LPHN1 | 29.023 | 0.0036545 |
| 23308 | ICOSLG | 29.012 | 0.0036652 |
| 3117 | HLA-DQA1 | 28.994 | 0.0036696 |
| 4775 | NFATC3 | 28.969 | 0.0036772 |
| 610 | HCN2 | 28.934 | 0.0037121 |
| 8021 | NUP214 | 28.802 | 0.003874 |
| 5003 | SLC22A18AS | 28.757 | 0.0039071 |
| 8174 | MADCAM1 | 28.732 | 0.0039196 |
| 7036 | TFR2 | 28.516 | 0.0041571 |
| 5252 | PHF1 | 28.508 | 0.0041612 |
| 10949 | HNRNPA0 | 28.387 | 0.0043054 |
| 3626 | INHBC | 28.361 | 0.0043396 |
| 79594 | MUL1 | 28.143 | 0.0046115 |
| 1528 | CYB5A | 28.104 | 0.0046774 |
| 8805 | TRIM24 | 27.861 | 0.0050111 |
| 54897 | CASZ1 | 27.831 | 0.0050468 |
| 5976 | UPF1 | 27.8 | 0.0050946 |
| 8724 | SNX3 | 27.773 | 0.0051295 |
| 51167 | CYB5R4 | 27.763 | 0.0051429 |
| 80724 | ACAD10 | 27.715 | 0.005213 |
| 7737 | RNF113A | 27.704 | 0.0052153 |
| 23588 | KLHDC2 | 27.582 | 0.0053556 |
| 782 | CACNB1 | 27.58 | 0.0053556 |
| 4779 | NFE2L1 | 27.556 | 0.0053921 |
| 2264 | FGFR4 | 27.509 | 0.0054553 |
| 1107 | CHD3 | 27.457 | 0.0055362 |
| 51663 | ZFR | 27.452 | 0.0055362 |
| 2542 | SLC37A4 | 27.416 | 0.0055963 |
| 23495 | TNFRSF13B | 27.397 | 0.0056319 |
| 4707 | NDUFB1 | 27.337 | 0.0057107 |
| 5296 | PIK3R2 | 27.291 | 0.0057664 |
| 11247 | NXPH4 | 27.287 | 0.0057664 |
| 22875 | ENPP4 | 27.254 | 0.0057925 |
| 3857 | KRT9 | 27.127 | 0.0060305 |
| 2835 | GPR12 | 27.094 | 0.0060964 |
| 10572 | SIVA1 | 27.064 | 0.0061315 |
| 1113 | CHGA | 27.047 | 0.0061657 |
| 5030 | P2RY4 | 26.995 | 0.0062437 |
| 54891 | INO80D | 26.987 | 0.0062546 |
| 9709 | HERPUD1 | 26.963 | 0.0062629 |
| 25816 | TNFAIP8 | 26.897 | 0.0063702 |
| 949 | SCARB1 | 26.891 | 0.0063776 |
| 10534 | SSSCA1 | 26.874 | 0.0064004 |
| 91 | ACVR1B | 26.859 | 0.0064161 |
| 5192 | PEX10 | 26.818 | 0.0064687 |
| 79188 | TMEM43 | 26.814 | 0.0064718 |
| 22876 | INPP5F | 26.787 | 0.0065036 |
| 27141 | CIDEB | 26.783 | 0.0065036 |
| 54558 | SPATA6 | 26.772 | 0.0065137 |
| 27091 | CACNG5 | 26.675 | 0.0067005 |
| 10298 | PAK4 | 26.652 | 0.0067467 |
| 81492 | RSPH6A | 26.646 | 0.0067486 |

TABLE 3-continued

Complete list of differentially expressed genes.

| Entrez ID | Gene symbol (Name) | Combined Tstat | Combined Pval |
|---|---|---|---|
| 6867 | TACC1 | 26.541 | 0.0069817 |
| 9683 | N4BP1 | 26.293 | 0.0074202 |
| 54923 | LIME1 | 26.264 | 0.0074915 |
| 8364 | HIST1H4C | 26.23 | 0.0075366 |
| 3643 | INSR | 26.061 | 0.0078736 |
| 23367 | LARP1 | 26.006 | 0.0079814 |
| 1659 | DHX8 | 25.903 | 0.0082443 |
| 6618 | SNAPC2 | 25.857 | 0.0083523 |
| 55802 | DCP1A | 25.851 | 0.0083555 |
| 6305 | SBF1 | 25.783 | 0.0085214 |
| 7874 | USP7 | 25.763 | 0.0085612 |
| 4913 | NTHL1 | 25.755 | 0.0085644 |
| 81606 | LBH | 25.734 | 0.0086266 |
| 8767 | RIPK2 | 25.692 | 0.0087353 |
| 54905 | CYP2W1 | 25.677 | 0.0087499 |
| 6284 | S100A13 | 25.676 | 0.0087499 |
| 55274 | PHF10 | 25.675 | 0.0087499 |
| 3881 | KRT31 | 25.664 | 0.0087705 |
| 8874 | ARHGEF7 | 25.645 | 0.0088009 |
| 2829 | XCR1 | 25.639 | 0.0088127 |
| 6134 | RPL10 | 25.621 | 0.0088596 |
| 29883 | CNOT7 | 25.614 | 0.0088768 |
| 6559 | SLC12A3 | 25.6 | 0.0088825 |
| 65057 | ACD | 25.506 | 0.0091595 |
| 1880 | GPR183 | 25.457 | 0.0092841 |
| 27079 | RPUSD2 | 25.445 | 0.0093124 |
| 51052 | PRLH | 25.381 | 0.0094767 |
| 29123 | ANKRD11 | 25.34 | 0.009584 |
| 9091 | PIGQ | 25.321 | 0.0096224 |
| 7016 | TESK1 | 25.3 | 0.009661 |
| 7852 | CXCR4 | 25.226 | 0.0098413 |
| 924 | CD7 | 25.216 | 0.0098552 |
| 23368 | PPP1R13B | 25.163 | 0.010013 |
| 54858 | PGPEP1 | 25.151 | 0.010042 |
| 5170 | PDPK1 | 25.118 | 0.010126 |
| 3659 | IRF1 | 25.114 | 0.010126 |
| 4282 | MIF | 25.036 | 0.010363 |
| 2692 | GHRHR | 25.009 | 0.010427 |
| 83955 | NACAP1 | 24.966 | 0.010491 |
| 196403 | DTX3 | 24.95 | 0.010533 |
| 24146 | CLDN15 | 24.909 | 0.010654 |
| 23162 | MAPK8IP3 | 24.903 | 0.010673 |
| 11009 | IL24 | 24.875 | 0.010712 |
| 51406 | NOL7 | 24.861 | 0.010751 |
| 9146 | HGS | 24.791 | 0.010885 |
| 1633 | DCK | 24.723 | 0.011098 |
| 64410 | KLHL25 | 24.709 | 0.011127 |
| 9903 | KLHL21 | 24.625 | 0.011396 |
| 81853 | TMEM14B | 24.612 | 0.011434 |
| 27092 | CACNG4 | 24.598 | 0.011478 |
| 6928 | HNF1B | 24.568 | 0.011561 |
| 54800 | KLHL24 | 24.551 | 0.01161 |
| 64180 | DPEP3 | 24.504 | 0.011747 |
| 54939 | COMMD4 | 24.491 | 0.01179 |
| 1212 | CLTB | 24.472 | 0.011863 |
| 51106 | TFB1M | 24.467 | 0.011875 |
| 10075 | HUWE1 | 24.429 | 0.011962 |
| 56904 | SH3GLB2 | 24.387 | 0.012095 |
| 23639 | LRRC6 | 24.37 | 0.01214 |
| 54328 | GPR173 | 24.344 | 0.012204 |
| 54946 | SLC41A3 | 24.299 | 0.012327 |
| 23376 | UFL1 | 24.287 | 0.012372 |
| 25948 | KBTBD2 | 24.268 | 0.012456 |
| 4771 | NF2 | 24.202 | 0.012703 |
| 2303 | FOXC2 | 24.155 | 0.012875 |
| 51150 | SDF4 | 24.054 | 0.013206 |
| 3094 | HINT1 | 24.049 | 0.013211 |
| 5984 | RFC4 | 24.039 | 0.013233 |
| 11260 | XPOT | 23.906 | 0.013717 |
| 140467 | ZNF358 | 23.898 | 0.013737 |
| 689 | BTF3 | 23.887 | 0.013776 |
| 56650 | CLDND1 | 23.846 | 0.013909 |
| 1513 | CTSK | 23.716 | 0.014299 |
| 6497 | SKI | 23.681 | 0.01443 |
| 5970 | RELA | 23.676 | 0.014447 |
| 79413 | ZBED2 | 23.595 | 0.014807 |
| 2810 | SFN | 23.519 | 0.015173 |
| 894 | CCND2 | 23.517 | 0.015173 |
| 79622 | SNRNP25 | 23.506 | 0.015173 |
| 1198 | CLK3 | 23.503 | 0.015173 |
| 55337 | C19orf66 | 23.476 | 0.015302 |
| 2843 | GPR20 | 23.426 | 0.015499 |
| 65988 | ZNF747 | 23.423 | 0.015508 |
| 56994 | CHPT1 | 23.406 | 0.015539 |
| 5140 | PDE3B | 23.382 | 0.01564 |
| 4487 | MSX1 | 23.376 | 0.01566 |
| 1877 | E4F1 | 23.348 | 0.015743 |
| 9516 | LITAF | 23.321 | 0.015845 |
| 57820 | CCNB1IP1 | 23.291 | 0.015959 |
| 79414 | LRFN3 | 23.253 | 0.016134 |
| 6440 | SFTPC | 23.166 | 0.016517 |
| 4841 | NONO | 23.148 | 0.016589 |
| 11124 | FAF1 | 23.129 | 0.016673 |
| 84124 | ZNF394 | 23.108 | 0.016751 |
| 2010 | EMD | 23.091 | 0.016801 |
| 79034 | C7orf26 | 22.998 | 0.017211 |
| 54915 | YTHDF1 | 22.951 | 0.017421 |
| 8483 | CILP | 22.892 | 0.017577 |
| 93 | ACVR2B | 22.888 | 0.017583 |
| 3748 | KCNC3 | 22.86 | 0.017725 |
| 3957 | LGALS2 | 22.855 | 0.017742 |
| 2359 | FPR3 | 22.829 | 0.017888 |
| 23383 | MAU2 | 22.822 | 0.017909 |
| 8560 | DEGS1 | 22.82 | 0.017909 |
| 146542 | ZNF688 | 22.808 | 0.017935 |
| 54851 | ANKRD49 | 22.807 | 0.017935 |
| 1543 | CYP1A1 | 22.803 | 0.017943 |
| 79656 | BEND5 | 22.799 | 0.017951 |
| 26232 | FBXO2 | 22.79 | 0.017971 |
| 23013 | SPEN | 22.783 | 0.017995 |
| 51596 | CUTA | 22.776 | 0.018002 |
| 8542 | APOL1 | 22.766 | 0.018038 |
| 55178 | RNMTL1 | 22.759 | 0.018063 |
| 6357 | CCL13 | 22.753 | 0.018098 |
| 1739 | DLG1 | 22.746 | 0.018132 |
| 1523 | CUX1 | 22.732 | 0.018206 |
| 3954 | LETM1 | 22.727 | 0.018207 |
| 8045 | RASSF7 | 22.726 | 0.018207 |
| 55339 | WDR33 | 22.724 | 0.018214 |
| 57007 | PNPLA2 | 22.683 | 0.018368 |
| 54344 | DPM3 | 22.681 | 0.018368 |
| 7352 | UCP3 | 22.673 | 0.018375 |
| 9128 | PRPF4 | 22.645 | 0.018481 |
| 5955 | RCN2 | 22.62 | 0.018597 |
| 3817 | KLK2 | 22.62 | 0.018597 |
| 9362 | CPNE6 | 22.604 | 0.018635 |
| 6861 | SYT5 | 22.596 | 0.018658 |
| 84986 | ARHGAP19 | 22.592 | 0.018662 |
| 3704 | ITPA | 22.574 | 0.01872 |
| 84705 | GTPBP3 | 22.566 | 0.01876 |
| 6146 | RPL22 | 22.541 | 0.018847 |
| 10933 | MORF4L1 | 22.502 | 0.019081 |
| 10865 | ARID5A | 22.498 | 0.019099 |
| 9969 | MED13 | 22.492 | 0.019127 |
| 6881 | TAF10 | 22.485 | 0.019161 |
| 55267 | C22orf26 | 22.473 | 0.019232 |
| 5096 | PCCB | 22.46 | 0.019289 |
| 105 | ADARB2 | 22.448 | 0.019312 |
| 4107 | MAGE A8 | 22.435 | 0.019337 |
| 2339 | FNTA | 22.419 | 0.019421 |
| 4824 | NKX3-1 | 22.419 | 0.019421 |
| 203 | AK1 | 22.417 | 0.019421 |
| 58478 | ENOPH1 | 22.387 | 0.019522 |
| 55311 | ZNF444 | 22.38 | 0.019543 |
| 1394 | CRHR1 | 22.333 | 0.01975 |
| 10585 | POMT1 | 22.302 | 0.019906 |
| 5652 | PRSS8 | 22.286 | 0.019989 |
| 5007 | OSBP | 22.273 | 0.020053 |
| 23334 | SZT2 | 22.27 | 0.02006 |
| 114884 | OSBPL10 | 22.238 | 0.020209 |

TABLE 3-continued

Complete list of differentially expressed genes.

| Entrez ID | Gene symbol (Name) | Combined Tstat | Combined Pval |
|---|---|---|---|
| 5195 | PEX14 | 22.232 | 0.020209 |
| 23043 | TNIK | 22.231 | 0.020209 |
| 253782 | CERS6 | 22.227 | 0.02023 |
| 51611 | DPH5 | 22.223 | 0.020246 |
| 7048 | TGFBR2 | 22.192 | 0.020344 |
| 6794 | STK11 | 22.173 | 0.020465 |
| 25844 | YIPF3 | 22.173 | 0.020465 |
| 4204 | MECP2 | 22.151 | 0.020574 |
| 9815 | GIT2 | 22.15 | 0.020574 |
| 5435 | POLR2F | 22.138 | 0.020588 |
| 5957 | RCVRN | 22.11 | 0.020709 |
| 2539 | G6PD | 22.101 | 0.020767 |
| 2002 | ELK1 | 22.037 | 0.021165 |
| 1355 | COX15 | 22.029 | 0.021176 |
| 51634 | RBMX2 | 21.98 | 0.021424 |
| 80011 | FAM192A | 21.973 | 0.021454 |
| 63892 | THADA | 21.96 | 0.021543 |
| 148066 | ZNRF4 | 21.927 | 0.021729 |
| 79695 | GALNT12 | 21.906 | 0.021809 |
| 22837 | COBLL1 | 21.888 | 0.021909 |
| 10845 | CLPX | 21.876 | 0.021961 |
| 8366 | HIST1H4B | 21.871 | 0.021972 |
| 4210 | MEFV | 21.867 | 0.021992 |
| 10107 | TRIM10 | 21.825 | 0.022222 |
| 9982 | FGFBP1 | 21.803 | 0.022327 |
| 6865 | TACR2 | 21.779 | 0.022475 |
| 246126 | TXLNG2P | 21.766 | 0.02255 |
| 54733 | SLC35F2 | 21.751 | 0.022629 |
| 5450 | POU2AF1 | 21.746 | 0.022643 |
| 23468 | CBX5 | 21.725 | 0.022763 |
| 54971 | BANP | 21.719 | 0.022797 |
| 757 | TMEM50B | 21.702 | 0.022811 |
| 10608 | MXD4 | 21.678 | 0.022948 |
| 4284 | MIP | 21.636 | 0.023167 |
| 7260 | TSSC1 | 21.598 | 0.023402 |
| 5730 | PTGDS | 21.582 | 0.023496 |
| 55323 | LARP6 | 21.577 | 0.023563 |
| 114881 | OSBPL7 | 21.564 | 0.02359 |
| 54149 | C21orf91 | 21.556 | 0.02359 |
| 4752 | NEK3 | 21.556 | 0.02359 |
| 10519 | CIB1 | 21.551 | 0.023604 |
| 7270 | TTF1 | 21.526 | 0.023725 |
| 25873 | RPL36 | 21.52 | 0.023748 |
| 55630 | SLC39A4 | 21.5 | 0.023814 |
| 55508 | SLC35E3 | 21.49 | 0.023892 |
| 3718 | JAK3 | 21.482 | 0.023947 |
| 56731 | SLC2A4RG | 21.44 | 0.024171 |
| 1760 | DMPK | 21.394 | 0.024467 |
| 256949 | KANK3 | 21.384 | 0.024525 |
| 8786 | RGS11 | 21.339 | 0.02482 |
| 80183 | KIAA0226L | 21.338 | 0.02482 |
| 10201 | NME6 | 21.311 | 0.024953 |
| 10456 | HAX1 | 21.272 | 0.025256 |
| 7392 | USF2 | 21.261 | 0.025317 |
| 66035 | SLC2A11 | 21.224 | 0.025485 |
| 3484 | IGFBP1 | 21.179 | 0.025795 |
| 3664 | IRF6 | 21.176 | 0.025804 |
| 3764 | KCNJ8 | 21.156 | 0.025961 |
| 4255 | MGMT | 21.151 | 0.025993 |
| 58494 | JAM2 | 21.148 | 0.026009 |
| 26959 | HBP1 | 21.133 | 0.026089 |
| 60370 | AVPI1 | 21.073 | 0.026486 |
| 5148 | PDE6G | 21.055 | 0.026602 |
| 51333 | ZNF771 | 21.047 | 0.026639 |
| 886 | CCKAR | 21.042 | 0.026663 |
| 4332 | MNDA | 21.037 | 0.026697 |
| 1967 | EIF2B1 | 21.028 | 0.026747 |
| 8934 | RAB7L1 | 21.023 | 0.026776 |
| 55321 | TMEM74B | 21.017 | 0.026817 |
| 2644 | GCHFR | 21.011 | 0.026844 |
| 55854 | ZC3H15 | 20.988 | 0.027013 |
| 2962 | GTF2F1 | 20.984 | 0.027034 |
| 1933 | EEF1B2 | 20.98 | 0.027052 |
| 4826 | NNAT | 20.98 | 0.027052 |
| 29924 | EPN1 | 20.908 | 0.027482 |
| 9482 | STX8 | 20.901 | 0.027511 |
| 10892 | MALT1 | 20.891 | 0.027567 |
| 54681 | P4HTM | 20.891 | 0.027567 |
| 2841 | GPR18 | 20.883 | 0.027621 |
| 26136 | TES | 20.88 | 0.027638 |
| 4807 | NHLH1 | 20.879 | 0.027638 |
| 48 | ACO1 | 20.87 | 0.027716 |
| 26156 | RSL1D1 | 20.864 | 0.02775 |
| 7707 | ZNF148 | 20.849 | 0.02783 |
| 23386 | NUDCD3 | 20.83 | 0.027968 |
| 973 | CD79A | 20.802 | 0.028184 |
| 5698 | PSMB9 | 20.79 | 0.028263 |
| 55794 | DDX28 | 20.786 | 0.028268 |
| 6474 | SHOX2 | 20.782 | 0.028293 |
| 4629 | MYH11 | 20.763 | 0.028387 |
| 5303 | PIN4 | 20.762 | 0.028387 |
| 10202 | DHRS2 | 20.74 | 0.02852 |
| 81858 | SHARPIN | 20.737 | 0.028539 |
| 23332 | CLASP1 | 20.733 | 0.028566 |
| 79803 | HPS6 | 20.725 | 0.02859 |
| 79600 | TCTN1 | 20.718 | 0.02859 |
| 581 | BAX | 20.716 | 0.02859 |
| 127833 | SYT2 | 20.684 | 0.028812 |
| 1233 | CCR4 | 20.681 | 0.028812 |
| 23471 | TRAM1 | 20.676 | 0.028821 |
| 572 | BAD | 20.649 | 0.029002 |
| 54861 | SNRK | 20.621 | 0.029227 |
| 135138 | PACRG | 20.588 | 0.029452 |
| 7693 | ZNF134 | 20.584 | 0.029459 |
| 8624 | PSMG1 | 20.573 | 0.029504 |
| 56245 | C21orf62 | 20.553 | 0.029664 |
| 3217 | HOXB7 | 20.539 | 0.029774 |
| 4192 | MDK | 20.529 | 0.029842 |
| 2817 | GPC1 | 20.528 | 0.029846 |
| 51295 | ECSIT | 20.52 | 0.02989 |
| 6810 | STX4 | 20.496 | 0.030035 |
| 4176 | MCM7 | 20.494 | 0.030035 |
| 3589 | IL11 | 20.489 | 0.030051 |
| 3739 | KCNA4 | 20.484 | 0.03006 |
| 7404 | UTY | 20.462 | 0.03023 |
| 9296 | ATP6V1F | 20.441 | 0.030408 |
| 9329 | GTF3C4 | 20.44 | 0.030408 |
| 5583 | PRKCH | 20.435 | 0.030425 |
| 11092 | C9orf9 | 20.411 | 0.03064 |
| 57827 | C6orf47 | 20.406 | 0.030677 |
| 1548 | CYP2A6 | 20.373 | 0.03093 |
| 25999 | CLIP3 | 20.369 | 0.030952 |
| 10922 | FASTK | 20.367 | 0.030952 |
| 55009 | C19orf24 | 20.336 | 0.031154 |
| 9022 | CLIC3 | 20.324 | 0.031262 |
| 54961 | SSH3 | 20.291 | 0.031526 |
| 64077 | LHPP | 20.253 | 0.03186 |
| 23451 | SF3B1 | 20.252 | 0.03186 |
| 867 | CBL | 20.25 | 0.031871 |
| 54093 | SETD4 | 20.226 | 0.032043 |
| 1419 | CRYGB | 20.225 | 0.032043 |
| 28962 | OSTM1 | 20.218 | 0.032058 |
| 868 | CBLB | 20.194 | 0.032276 |
| 9778 | KIAA0232 | 20.173 | 0.032437 |
| 11161 | C14orf1 | 20.149 | 0.032652 |
| 2245 | FGD1 | 20.146 | 0.032654 |
| 80153 | EDC3 | 20.134 | 0.032764 |
| 56548 | CHST7 | 20.133 | 0.032764 |
| 10220 | GDF11 | 20.088 | 0.033259 |
| 10174 | SORBS3 | 20.08 | 0.033336 |
| 4832 | NME3 | 20.068 | 0.033427 |
| 10291 | SF3A1 | 20.067 | 0.033427 |
| 29761 | USP25 | 20.03 | 0.033716 |
| 51151 | SLC45A2 | 20.03 | 0.033716 |
| 2788 | GNG7 | 20.014 | 0.033807 |
| 80774 | LIMD2 | 20.014 | 0.033807 |
| 25790 | CCDC19 | 20.014 | 0.033807 |
| 10262 | SF3B4 | 19.992 | 0.033999 |
| 23484 | LEPROTL1 | 19.985 | 0.034038 |
| 64793 | CEP85 | 19.985 | 0.034038 |

TABLE 3-continued

Complete list of differentially expressed genes.

| Entrez ID | Gene symbol (Name) | Combined Tstat | Combined Pval |
|---|---|---|---|
| 26015 | RPAP1 | 19.962 | 0.03423 |
| 7586 | ZKSCAN1 | 19.926 | 0.034511 |
| 79668 | PARP8 | 19.914 | 0.034565 |
| 29855 | UBN1 | 19.894 | 0.034744 |
| 5143 | PDE4C | 19.853 | 0.035179 |
| 27132 | CPNE7 | 19.846 | 0.035197 |
| 7471 | WNT1 | 19.842 | 0.035243 |
| 10452 | TOMM40 | 19.819 | 0.035478 |
| 4124 | MAN2A1 | 19.813 | 0.035498 |
| 81030 | ZBP1 | 19.811 | 0.035498 |
| 79929 | MAP6D1 | 19.811 | 0.035498 |
| 5345 | SERPINF2 | 19.807 | 0.035506 |
| 64063 | PRSS22 | 19.795 | 0.035601 |
| 4482 | MSRA | 19.783 | 0.035682 |
| 1482 | NKX2-5 | 19.767 | 0.035833 |
| 1499 | CTNNB1 | 19.75 | 0.035954 |
| 57835 | SLC4A5 | 19.701 | 0.036418 |
| 1369 | CPN1 | 19.7 | 0.036418 |
| 5695 | PSMB7 | 19.697 | 0.036437 |
| 839 | CASP6 | 19.676 | 0.036655 |
| 83714 | NRIP2 | 19.653 | 0.036894 |
| 55063 | ZCWPW1 | 19.643 | 0.036966 |
| 10520 | ZNF211 | 19.635 | 0.037004 |
| 10897 | YIF1A | 19.634 | 0.037004 |
| 171586 | ABHD3 | 19.633 | 0.037004 |
| 7375 | USP4 | 19.627 | 0.03701 |
| 696 | BTN1A1 | 19.603 | 0.037287 |
| 5371 | PML | 19.601 | 0.037301 |
| 230 | ALDOC | 19.598 | 0.037326 |
| 10469 | TIMM44 | 19.59 | 0.037376 |
| 3658 | IREB2 | 19.589 | 0.037376 |
| 5037 | PEBP1 | 19.589 | 0.037376 |
| 55145 | THAP1 | 19.554 | 0.037709 |
| 7423 | VEGFB | 19.549 | 0.03776 |
| 9403 | SEP15 | 19.539 | 0.037882 |
| 55090 | MED9 | 19.537 | 0.037896 |
| 22800 | RRAS2 | 19.513 | 0.038098 |
| 6750 | SST | 19.501 | 0.038185 |
| 4858 | NOVA2 | 19.487 | 0.038303 |
| 6282 | S100A11 | 19.475 | 0.038387 |
| 8526 | DGKE | 19.474 | 0.038387 |
| 1488 | CTBP2 | 19.43 | 0.038804 |
| 222161 | DKFZP586I1420 | 19.406 | 0.039053 |
| 956 | ENTPD3 | 19.397 | 0.039139 |
| 3669 | ISG20 | 19.395 | 0.039139 |
| 23 | ABCF1 | 19.382 | 0.039243 |
| 78996 | C7orf49 | 19.362 | 0.039443 |
| 64097 | EPB41L4A | 19.304 | 0.040077 |
| 55030 | FBXO34 | 19.296 | 0.040179 |
| 1298 | COL9A2 | 19.295 | 0.040179 |
| 29098 | RANGRF | 19.292 | 0.040193 |
| 8824 | CES2 | 19.268 | 0.040446 |
| 734 | OSGIN2 | 19.252 | 0.040594 |
| 23452 | ANGPTL2 | 19.239 | 0.040738 |
| 29775 | CARD10 | 19.234 | 0.040782 |
| 28978 | TMEM14A | 19.217 | 0.041012 |
| 79068 | FTO | 19.21 | 0.041062 |
| 7275 | TUB | 19.206 | 0.041082 |
| 1381 | CRABP1 | 19.188 | 0.041266 |
| 22897 | CEP164 | 19.182 | 0.041302 |
| 201254 | STRA13 | 19.176 | 0.041361 |
| 9922 | IQSEC1 | 19.174 | 0.041361 |
| 54476 | RNF216 | 19.167 | 0.04142 |
| 5031 | P2RY6 | 19.159 | 0.041491 |
| 1059 | CENPB | 19.147 | 0.041602 |
| 23429 | RYBP | 19.109 | 0.04202 |
| 1174 | AP1S1 | 19.106 | 0.04202 |
| 4649 | MYO9A | 19.104 | 0.042027 |
| 51283 | BFAR | 19.094 | 0.04214 |
| 55422 | ZNF331 | 19.078 | 0.042326 |
| 6992 | PPP1R11 | 19.067 | 0.042455 |
| 921 | CD5 | 19.048 | 0.042703 |
| 23648 | SSBP3 | 19.033 | 0.042863 |
| 796 | CALCA | 19.032 | 0.042869 |
| 64284 | RAB17 | 19.018 | 0.042989 |
| 55222 | LRRC20 | 19.011 | 0.043055 |
| 57152 | SLURP1 | 19.01 | 0.043059 |
| 9779 | TBC1D5 | 19.007 | 0.043087 |
| 51170 | HSD17B11 | 19 | 0.043171 |
| 55223 | TRIM62 | 18.997 | 0.04319 |
| 8111 | GPR68 | 18.997 | 0.04319 |
| 63931 | MRPS14 | 18.97 | 0.043409 |
| 5442 | POLRMT | 18.964 | 0.043467 |
| 539 | ATP5O | 18.949 | 0.043581 |
| 79778 | MICALL2 | 18.943 | 0.043651 |
| 5995 | RGR | 18.938 | 0.043716 |
| 10432 | RBM14 | 18.915 | 0.043919 |
| 6035 | RNASE1 | 18.911 | 0.043937 |
| 26001 | RNF167 | 18.909 | 0.043937 |
| 79643 | CHMP6 | 18.903 | 0.043978 |
| 79029 | SPATA5L1 | 18.897 | 0.044044 |
| 10868 | USP20 | 18.885 | 0.044211 |
| 6314 | ATXN7 | 18.853 | 0.044485 |
| 3303 | HSPA1A | 18.842 | 0.044628 |
| 2877 | GPX2 | 18.822 | 0.044791 |
| 11168 | PSIP1 | 18.809 | 0.044863 |
| 841 | CASP8 | 18.804 | 0.044922 |
| 2806 | GOT2 | 18.776 | 0.045226 |
| 10927 | SPIN1 | 18.773 | 0.045246 |
| 9616 | RNF7 | 18.735 | 0.045718 |
| 8933 | FAM127A | 18.73 | 0.045791 |
| 4776 | NFATC4 | 18.722 | 0.045864 |
| 399979 | SNX19 | 18.709 | 0.046058 |
| 931 | MS4A1 | 18.701 | 0.046126 |
| 8929 | PHOX2B | 18.695 | 0.046215 |
| 56255 | TMX4 | 18.67 | 0.046501 |
| 8737 | RIPK1 | 18.65 | 0.046691 |
| 25813 | SAMM50 | 18.646 | 0.046705 |
| 7494 | XBP1 | 18.645 | 0.046705 |
| 161 | AP2A2 | 18.629 | 0.046923 |
| 7695 | ZNF136 | 18.614 | 0.047119 |
| 9908 | G3BP2 | 18.61 | 0.047156 |
| 54549 | SDK2 | 18.559 | 0.04775 |
| 8237 | USP11 | 18.555 | 0.047778 |
| 1103 | CHAT | 18.55 | 0.04778 |
| 55252 | ASXL2 | 18.544 | 0.047813 |
| 3177 | SLC29A2 | 18.531 | 0.047998 |
| 8776 | MTMR1 | 18.527 | 0.048042 |
| 60491 | NIF3L1 | 18.512 | 0.048219 |
| 23528 | ZNF281 | 18.498 | 0.048357 |
| 3480 | IGF1R | 18.488 | 0.048432 |
| 3489 | IGFBP6 | 18.484 | 0.04849 |
| 9032 | TM4SF5 | 18.471 | 0.048662 |
| 23394 | ADNP | 18.468 | 0.048686 |
| 5089 | PBX2 | 18.461 | 0.048761 |
| 64121 | RRAGC | 18.452 | 0.04883 |
| 23263 | MCF2L | 18.401 | 0.049564 |
| 51154 | MRTO4 | 18.401 | 0.049564 |
| 65992 | DDRGK1 | 18.399 | 0.049564 |
| 29992 | PILRA | 18.399 | 0.049564 |
| Downregulated genes | | | |
| 5725 | PTBP1 | −58.731 | 5.60E−07 |
| 6521 | SLC4A1 | −58.117 | 6.77E−07 |
| 9802 | DAZAP2 | −56.939 | 9.20E−07 |
| 2038 | EPB42 | −55.377 | 1.39E−06 |
| 9931 | HELZ | −54.311 | 1.83E−06 |
| 8991 | SELENBP1 | −54.268 | 1.83E−06 |
| 11163 | NUDT4 | −53.277 | 2.54E−06 |
| 759 | CA1 | −52.77 | 2.97E−06 |
| 51327 | AHSP | −52.673 | 3.00E−06 |
| 212 | ALAS2 | −52.324 | 3.40E−06 |
| 29978 | UBQLN2 | −52.105 | 3.52E−06 |
| 830 | CAPZA2 | −51.962 | 3.63E−06 |
| 66008 | TRAK2 | −51.502 | 4.12E−06 |
| 23392 | KIAA0368 | −50.109 | 6.91E−06 |
| 5538 | PPT1 | −49.825 | 7.37E−06 |
| 9741 | LAPTM4A | −48.994 | 9.90E−06 |
| 10523 | CHERP | −48.748 | 1.08E−05 |
| 4602 | MYB | −48.593 | 1.09E−05 |

TABLE 3-continued

Complete list of differentially expressed genes.

| Entrez ID | Gene symbol (Name) | Combined Tstat | Combined Pval |
|---|---|---|---|
| 3312 | HSPA8 | −48.59 | 1.09E−05 |
| 54518 | APBB1IP | −48.031 | 1.30E−05 |
| 374868 | ATP9B | −47.683 | 1.46E−05 |
| 9320 | TRIP12 | −47.407 | 1.59E−05 |
| 23262 | PPIP5K2 | −47.18 | 1.73E−05 |
| 54432 | YIPF1 | −46.662 | 2.04E−05 |
| 533 | ATP6V0B | −46.62 | 2.05E−05 |
| 5292 | PIM1 | −46.48 | 2.11E−05 |
| 10550 | ARL6IP5 | −46.428 | 2.13E−05 |
| 23406 | COTL1 | −45.707 | 2.62E−05 |
| 9131 | AIFM1 | −45.467 | 2.87E−05 |
| 1859 | DYRK1A | −45.42 | 2.89E−05 |
| 55421 | C17orf85 | −44.974 | 3.38E−05 |
| 204851 | HIPK1 | −44.829 | 3.56E−05 |
| 51385 | ZNF589 | −44.618 | 3.86E−05 |
| 7353 | UFD1L | −44.369 | 4.20E−05 |
| 3045 | HBD | −44.194 | 4.48E−05 |
| 55197 | RPRD1A | −43.955 | 4.81E−05 |
| 4677 | NARS | −43.741 | 5.17E−05 |
| 3049 | HBQ1 | −43.698 | 5.17E−05 |
| 1465 | CSRP1 | −43.687 | 5.17E−05 |
| 220972 | MARCH8 | −43.565 | 5.39E−05 |
| 23256 | SCFD1 | −43.314 | 5.83E−05 |
| 4694 | NDUFA1 | −43.262 | 5.90E−05 |
| 7411 | VBP1 | −43.217 | 5.96E−05 |
| 6713 | SQLE | −43.19 | 5.97E−05 |
| 8761 | PABPC4 | −43.113 | 6.05E−05 |
| 155066 | ATP6V0E2 | −43.111 | 6.05E−05 |
| 10908 | PNPLA6 | −43.091 | 6.05E−05 |
| 408 | ARRB1 | −42.665 | 7.01E−05 |
| 1349 | COX7B | −42.633 | 7.04E−05 |
| 5810 | RAD1 | −42.484 | 7.45E−05 |
| 1445 | CSK | −42.358 | 7.79E−05 |
| 54832 | VPS13C | −42.329 | 7.80E−05 |
| 11154 | AP4S1 | −42.316 | 7.80E−05 |
| 4726 | NDUFS6 | −42.295 | 7.80E−05 |
| 6510 | SLC1A5 | −42.105 | 8.32E−05 |
| 2235 | FECH | −42.062 | 8.33E−05 |
| 3134 | HLA-F | −41.962 | 8.62E−05 |
| 1154 | CISH | −41.92 | 8.71E−05 |
| 23741 | EID1 | −41.776 | 9.04E−05 |
| 55589 | BMP2K | −41.755 | 9.05E−05 |
| 892 | CCNC | −41.616 | 9.46E−05 |
| 56889 | TM9SF3 | −41.48 | 9.95E−05 |
| 7045 | TGFBI | −41.431 | 0.00010085 |
| 2752 | GLUL | −41.217 | 0.00010807 |
| 79415 | C17orf62 | −41.098 | 0.00011121 |
| 2994 | GYPB | −40.783 | 0.00012641 |
| 51582 | AZIN1 | −40.685 | 0.00013086 |
| 9166 | EBAG9 | −40.593 | 0.00013319 |
| 51552 | RAB14 | −40.506 | 0.00013633 |
| 25793 | FBXO7 | −40.375 | 0.00014221 |
| 3421 | IDH3G | −40.375 | 0.00014221 |
| 81929 | SEH1L | −40.257 | 0.00014756 |
| 6502 | SKP2 | −40.023 | 0.00016201 |
| 9816 | URB2 | −39.973 | 0.0001644 |
| 375 | ARF1 | −39.934 | 0.00016605 |
| 55907 | CMAS | −39.907 | 0.00016684 |
| 64761 | PARP12 | −39.849 | 0.00016842 |
| 1874 | E2F4 | −39.84 | 0.00016842 |
| 8720 | MBTPS1 | −39.839 | 0.00016842 |
| 50999 | TMED5 | −39.802 | 0.00016912 |
| 6612 | SUMO3 | −39.762 | 0.00016912 |
| 9528 | TMEM59 | −39.761 | 0.00016912 |
| 7979 | SHFM1 | −39.753 | 0.00016912 |
| 6434 | TRA2B | −39.676 | 0.00017373 |
| 669 | BPGM | −39.653 | 0.00017432 |
| 7323 | UBE2D3 | −39.627 | 0.0001752 |
| 3689 | ITGB2 | −39.494 | 0.00018366 |
| 94239 | H2AFV | −39.458 | 0.00018486 |
| 1084 | CEACAM3 | −39.43 | 0.00018592 |
| 29969 | MDFIC | −39.356 | 0.00019079 |
| 6135 | RPL11 | −39.066 | 0.0002117 |
| 79623 | GALNT14 | −39.043 | 0.0002117 |
| 27034 | ACAD8 | −39.023 | 0.00021223 |
| 6748 | SSR4 | −38.976 | 0.00021524 |
| 6500 | SKP1 | −38.922 | 0.00021851 |
| 8864 | PER2 | −38.914 | 0.00021851 |
| 1738 | DLD | −38.864 | 0.00022192 |
| 5634 | PRPS2 | −38.845 | 0.00022253 |
| 10923 | SUB1 | −38.752 | 0.00022835 |
| 6728 | SRP19 | −38.744 | 0.00022835 |
| 4893 | NRAS | −38.676 | 0.00023303 |
| 84890 | ADO | −38.671 | 0.00023303 |
| 10492 | SYNCRIP | −38.65 | 0.00023384 |
| 2193 | FARSA | −38.588 | 0.00023875 |
| 5423 | POLB | −38.554 | 0.0002398 |
| 5537 | PPP6C | −38.552 | 0.0002398 |
| 8850 | KAT2B | −38.519 | 0.00024147 |
| 51312 | SLC25A37 | −38.511 | 0.00024147 |
| 3646 | EIF3E | −38.497 | 0.00024164 |
| 5266 | PI3 | −38.403 | 0.0002488 |
| 54964 | C1orf56 | −38.262 | 0.00026149 |
| 6603 | SMARCD2 | −38.248 | 0.00026171 |
| 1785 | DNM2 | −38.148 | 0.00027163 |
| 2937 | GSS | −38.094 | 0.00027653 |
| 9491 | PSMF1 | −37.861 | 0.00029769 |
| 3157 | HMGCS1 | −37.818 | 0.00030172 |
| 7384 | UQCRC1 | −37.752 | 0.00030731 |
| 8677 | STX10 | −37.678 | 0.00031552 |
| 26019 | UPF2 | −37.625 | 0.00032107 |
| 23596 | OPN3 | −37.6 | 0.00032298 |
| 1939 | EIF2D | −37.432 | 0.00034518 |
| 1399 | CRKL | −37.405 | 0.00034751 |
| 57380 | MRS2 | −37.353 | 0.00035232 |
| 9519 | TBPL1 | −37.35 | 0.00035232 |
| 6782 | HSPA13 | −37.317 | 0.00035549 |
| 824 | CAPN2 | −37.196 | 0.00037248 |
| 55666 | NPLOC4 | −37.178 | 0.00037355 |
| 378 | ARF4 | −37.151 | 0.00037616 |
| 6950 | TCP1 | −37.108 | 0.00038126 |
| 10138 | YAF2 | −37.091 | 0.00038232 |
| 10180 | RBM6 | −37.065 | 0.00038462 |
| 58533 | SNX6 | −36.925 | 0.00040279 |
| 10539 | GLRX3 | −36.924 | 0.00040279 |
| 51019 | CCDC53 | −36.834 | 0.00041648 |
| 51185 | CRBN | −36.82 | 0.00041719 |
| 1327 | COX4I1 | −36.785 | 0.00042138 |
| 22820 | COPG1 | −36.76 | 0.00042412 |
| 83937 | RASSF4 | −36.733 | 0.00042518 |
| 64083 | GOLPH3 | −36.733 | 0.00042518 |
| 23499 | MACF1 | −36.66 | 0.00043453 |
| 79892 | MCMBP | −36.557 | 0.00044836 |
| 23404 | EXOSC2 | −36.555 | 0.00044836 |
| 10096 | ACTR3 | −36.537 | 0.00044995 |
| 23151 | GRAMD4 | −36.506 | 0.00045294 |
| 6745 | SSR1 | −36.497 | 0.00045294 |
| 9978 | RBX1 | −36.454 | 0.00045612 |
| 4670 | HNRNPM | −36.441 | 0.00045672 |
| 8780 | RIOK3 | −36.413 | 0.00046024 |
| 3692 | EIF6 | −36.275 | 0.00048023 |
| 2987 | GUK1 | −36.273 | 0.00048023 |
| 11345 | GABARAPL2 | −36.142 | 0.00050121 |
| 5826 | ABCD4 | −36.121 | 0.00050362 |
| 51109 | RDH11 | −36.106 | 0.00050445 |
| 55743 | CHFR | −36.098 | 0.00050445 |
| 83440 | ADPGK | −36.019 | 0.00051939 |
| 9526 | MPDU1 | −36.01 | 0.00051939 |
| 23166 | STAB1 | −35.945 | 0.00052703 |
| 55621 | TRMT1 | −35.905 | 0.00053013 |
| 81550 | TDRD3 | −35.896 | 0.00053013 |
| 832 | CAPZB | −35.786 | 0.00055314 |
| 4191 | MDH2 | −35.647 | 0.00058202 |
| 2353 | FOS | −35.579 | 0.00059467 |
| 4088 | SMAD3 | −35.578 | 0.00059467 |
| 1185 | CLCN6 | −35.49 | 0.00061464 |
| 875 | CBS | −35.471 | 0.0006149 |
| 9111 | NMI | −35.46 | 0.0006154 |
| 79026 | AHNAK | −35.431 | 0.00061837 |
| 65264 | UBE2Z | −35.421 | 0.00061882 |

TABLE 3-continued

Complete list of differentially expressed genes.

| Entrez ID | Gene symbol (Name) | Combined Tstat | Combined Pval |
|---|---|---|---|
| 23223 | RRP12 | −35.411 | 0.00061918 |
| 2617 | GARS | −35.293 | 0.00064581 |
| 89910 | UBE3B | −35.281 | 0.00064653 |
| 5025 | P2RX4 | −35.177 | 0.0006705 |
| 598 | BCL2L1 | −35.157 | 0.00067249 |
| 5127 | CDK16 | −35.088 | 0.00068853 |
| 1175 | AP2S1 | −35.051 | 0.00069365 |
| 6683 | SPAST | −34.952 | 0.00071307 |
| 27068 | PPA2 | −34.882 | 0.00072598 |
| 10489 | LRRC41 | −34.87 | 0.00072598 |
| 3189 | HNRNPH3 | −34.839 | 0.00073301 |
| 10948 | STARD3 | −34.762 | 0.00075303 |
| 80135 | RPF1 | −34.758 | 0.00075303 |
| 5515 | PPP2CA | −34.729 | 0.00075963 |
| 25932 | CLIC4 | −34.697 | 0.00076745 |
| 23315 | SLC9A8 | −34.682 | 0.00076941 |
| 5531 | PPP4C | −34.641 | 0.00077757 |
| 23201 | FAM168A | −34.597 | 0.00078687 |
| 5684 | PSMA3 | −34.567 | 0.00079266 |
| 4891 | SLC11A2 | −34.563 | 0.00079266 |
| 3949 | LDLR | −34.528 | 0.00080186 |
| 10049 | DNAJB6 | −34.514 | 0.00080383 |
| 23633 | KPNA6 | −34.506 | 0.00080389 |
| 5716 | PSMD10 | −34.49 | 0.00080682 |
| 303 | ANXA2P1 | −34.46 | 0.00081204 |
| 3364 | HUS1 | −34.438 | 0.00081204 |
| 1725 | DHPS | −34.435 | 0.00081204 |
| 9246 | UBE2L6 | −34.413 | 0.00081451 |
| 56995 | TULP4 | −34.404 | 0.00081501 |
| 1778 | DYNC1H1 | −34.345 | 0.00083006 |
| 81622 | UNC93B1 | −34.282 | 0.00084692 |
| 124565 | SLC38A10 | −34.282 | 0.00084692 |
| 51112 | TRAPPC12 | −34.253 | 0.00085147 |
| 5908 | RAP1B | −34.244 | 0.00085147 |
| 6418 | SET | −34.233 | 0.00085147 |
| 79982 | DNAJB14 | −34.211 | 0.00085336 |
| 52 | ACP1 | −34.134 | 0.00087342 |
| 23248 | RPRD2 | −34.113 | 0.00087824 |
| 64919 | BCL11B | −34.096 | 0.00088085 |
| 2997 | GYS1 | −34.062 | 0.0008812 |
| 6773 | STAT2 | −34 | 0.0008962 |
| 3035 | HARS | −33.969 | 0.0009032 |
| 665 | BNIP3L | −33.967 | 0.0009032 |
| 10347 | ABCA7 | −33.923 | 0.0009174 |
| 7378 | UPP1 | −33.905 | 0.00092165 |
| 6574 | SLC20A1 | −33.868 | 0.0009332 |
| 5256 | PHKA2 | −33.85 | 0.00093469 |
| 54942 | FAM206A | −33.839 | 0.00093616 |
| 488 | ATP2A2 | −33.804 | 0.00094727 |
| 51719 | CAB39 | −33.779 | 0.00095167 |
| 9530 | BAG4 | −33.71 | 0.00097654 |
| 10362 | HMG20B | −33.635 | 0.00099902 |
| 51479 | ANKFY1 | −33.613 | 0.0010054 |
| 8562 | DENR | −33.604 | 0.0010065 |
| 4778 | NFE2 | −33.57 | 0.0010154 |
| 55654 | TMEM127 | −33.477 | 0.0010521 |
| 11315 | PARK7 | −33.466 | 0.0010521 |
| 3956 | LGALS1 | −33.464 | 0.0010521 |
| 381 | ARF5 | −33.443 | 0.0010584 |
| 329 | BIRC2 | −33.417 | 0.0010669 |
| 6787 | NEK4 | −33.375 | 0.0010825 |
| 55108 | BSDC1 | −33.348 | 0.0010916 |
| 5269 | SERPINB6 | −33.34 | 0.0010926 |
| 6421 | SFPQ | −33.312 | 0.0011023 |
| 83452 | RAB33B | −33.263 | 0.0011188 |
| 56951 | C5orf15 | −33.138 | 0.0011671 |
| 71 | ACTG1 | −33.055 | 0.0011939 |
| 908 | CCT6A | −32.98 | 0.0012244 |
| 27071 | DAPP1 | −32.973 | 0.0012244 |
| 10250 | SRRM1 | −32.973 | 0.0012244 |
| 55326 | AGPAT5 | −32.962 | 0.0012244 |
| 10844 | TUBGCP2 | −32.938 | 0.0012333 |
| 79017 | GGCT | −32.922 | 0.0012372 |
| 10209 | EIF1 | −32.913 | 0.0012372 |
| 6651 | SON | −32.903 | 0.0012372 |
| 55759 | WDR12 | −32.901 | 0.0012372 |
| 8649 | LAMTOR3 | −32.884 | 0.0012419 |
| 9604 | RNF14 | −32.833 | 0.001265 |
| 51096 | UTP18 | −32.82 | 0.0012651 |
| 2802 | GOLGA3 | −32.811 | 0.0012651 |
| 240 | ALOX5 | −32.808 | 0.0012651 |
| 6133 | RPL9 | −32.776 | 0.0012755 |
| 5734 | PTGER4 | −32.77 | 0.0012758 |
| 8314 | BAP1 | −32.764 | 0.0012758 |
| 6117 | RPA1 | −32.738 | 0.0012794 |
| 28952 | CCDC22 | −32.738 | 0.0012794 |
| 9854 | C2CD2L | −32.733 | 0.0012794 |
| 80762 | NDFIP1 | −32.703 | 0.0012889 |
| 5479 | PPIB | −32.682 | 0.0012969 |
| 51015 | ISOC1 | −32.66 | 0.0013053 |
| 6619 | SNAPC3 | −32.635 | 0.0013141 |
| 23360 | FNBP4 | −32.626 | 0.0013141 |
| 5045 | FURIN | −32.626 | 0.0013141 |
| 8639 | AOC3 | −32.62 | 0.0013143 |
| 10159 | ATP6AP2 | −32.582 | 0.0013308 |
| 116985 | ARAP1 | −32.572 | 0.0013308 |
| 5036 | PA2G4 | −32.538 | 0.0013467 |
| 25940 | FAM98A | −32.531 | 0.0013472 |
| 23157 | SEPT6 | −32.513 | 0.0013536 |
| 254394 | MCM9 | −32.446 | 0.0013746 |
| 50 | ACO2 | −32.441 | 0.0013746 |
| 199870 | FAM76A | −32.438 | 0.0013746 |
| 64783 | RBM15 | −32.436 | 0.0013746 |
| 10552 | ARPC1A | −32.396 | 0.0013939 |
| 7360 | UGP2 | −32.351 | 0.0014138 |
| 7504 | XK | −32.337 | 0.0014185 |
| 10904 | BLCAP | −32.329 | 0.0014199 |
| 10396 | ATP8A1 | −32.255 | 0.0014602 |
| 51727 | CMPK1 | −32.221 | 0.0014775 |
| 6892 | TAPBP | −32.208 | 0.0014821 |
| 2268 | FGR | −32.117 | 0.0015318 |
| 10015 | PDCD6IP | −32.101 | 0.0015383 |
| 6890 | TAP1 | −32.087 | 0.0015437 |
| 283537 | SLC46A3 | −32.032 | 0.0015755 |
| 7086 | TKT | −31.998 | 0.0015928 |
| 27101 | CACYBP | −31.994 | 0.0015928 |
| 55246 | CCDC25 | −31.989 | 0.0015928 |
| 79712 | GTDC1 | −31.968 | 0.0016017 |
| 9188 | DDX21 | −31.964 | 0.0016017 |
| 22908 | SACM1L | −31.902 | 0.0016332 |
| 9140 | ATG12 | −31.901 | 0.0016332 |
| 4711 | NDUFB5 | −31.868 | 0.0016513 |
| 79666 | PLEKHF2 | −31.862 | 0.0016519 |
| 53 | ACP2 | −31.854 | 0.0016539 |
| 1848 | DUSP6 | −31.844 | 0.0016568 |
| 4952 | OCRL | −31.824 | 0.0016666 |
| 9968 | MED12 | −31.79 | 0.0016866 |
| 23172 | FAM175B | −31.771 | 0.0016962 |
| 8764 | TNFRSF14 | −31.752 | 0.0017055 |
| 840 | CASP7 | −31.732 | 0.001716 |
| 23644 | EDC4 | −31.714 | 0.0017201 |
| 54765 | TRIM44 | −31.71 | 0.0017201 |
| 51606 | ATP6V1H | −31.666 | 0.0017454 |
| 3636 | INPPL1 | −31.664 | 0.0017454 |
| 9641 | IKBKE | −31.636 | 0.0017579 |
| 57192 | MCOLN1 | −31.607 | 0.0017671 |
| 24144 | TFIP11 | −31.594 | 0.0017713 |
| 397 | ARHGDIB | −31.591 | 0.0017713 |
| 1965 | EIF2S1 | −31.571 | 0.0017823 |
| 5993 | RFX5 | −31.566 | 0.0017823 |
| 5160 | PDHA1 | −31.529 | 0.0018051 |
| 8667 | EIF3H | −31.494 | 0.001813 |
| 11335 | CBX3 | −31.487 | 0.001813 |
| 11237 | RNF24 | −31.485 | 0.001813 |
| 7126 | TNFAIP1 | −31.478 | 0.001813 |
| 2314 | FLII | −31.474 | 0.001813 |
| 51184 | GPN3 | −31.472 | 0.001813 |
| 9868 | TOMM70A | −31.452 | 0.0018237 |
| 7351 | UCP2 | −31.446 | 0.0018237 |
| 2935 | GSPT1 | −31.443 | 0.0018237 |

TABLE 3-continued

Complete list of differentially expressed genes.

| Entrez ID | Gene symbol (Name) | Combined Tstat | Combined Pval |
|---|---|---|---|
| 55754 | TMEM30A | −31.394 | 0.0018453 |
| 23549 | DNPEP | −31.393 | 0.0018453 |
| 6888 | TALDO1 | −31.389 | 0.0018453 |
| 9788 | MTSS1 | −31.34 | 0.0018746 |
| 26608 | TBL2 | −31.295 | 0.0019032 |
| 522 | ATP5J | −31.294 | 0.0019032 |
| 55379 | LRRC59 | −31.271 | 0.0019146 |
| 4144 | MAT2A | −31.264 | 0.0019146 |
| 10399 | GNB2L1 | −31.233 | 0.0019314 |
| 56910 | STARD7 | −31.166 | 0.0019775 |
| 51614 | ERGIC3 | −31.166 | 0.0019775 |
| 2821 | GPI | −31.14 | 0.0019877 |
| 10678 | B3GNT2 | −31.138 | 0.0019877 |
| 8536 | CAMK1 | −31.138 | 0.0019877 |
| 9610 | RIN1 | −31.126 | 0.0019938 |
| 23637 | RABGAP1 | −31.112 | 0.0020013 |
| 25939 | SAMHD1 | −31.075 | 0.0020273 |
| 6829 | SUPT5H | −31.06 | 0.002036 |
| 26528 | DAZAP1 | −31.049 | 0.0020415 |
| 5526 | PPP2R5B | −31.037 | 0.0020431 |
| 27163 | NAAA | −31.034 | 0.0020431 |
| 22868 | FASTKD2 | −31.032 | 0.0020431 |
| 4784 | NFIX | −31.025 | 0.0020431 |
| 10653 | SPINT2 | −31.023 | 0.0020433 |
| 55544 | RBM38 | −31.014 | 0.0020461 |
| 835 | CASP2 | −30.976 | 0.0020746 |
| 23608 | MKRN1 | −30.942 | 0.0020992 |
| 79036 | KXD1 | −30.905 | 0.0021228 |
| 4057 | LTF | −30.878 | 0.0021422 |
| 90273 | CEACAM21 | −30.828 | 0.0021781 |
| 6622 | SNCA | −30.81 | 0.0021859 |
| 23081 | KDM4C | −30.762 | 0.002225 |
| 10666 | CD226 | −30.747 | 0.0022299 |
| 6940 | ZNF354A | −30.731 | 0.0022409 |
| 9911 | TMCC2 | −30.713 | 0.0022524 |
| 22985 | ACIN1 | −30.686 | 0.0022681 |
| 58497 | PRUNE | −30.682 | 0.0022681 |
| 11116 | FGFR1OP | −30.655 | 0.0022891 |
| 873 | CBR1 | −30.639 | 0.0023003 |
| 91782 | CHMP7 | −30.621 | 0.0023125 |
| 55193 | PBRM1 | −30.572 | 0.0023458 |
| 1124 | CHN2 | −30.544 | 0.0023635 |
| 34 | ACADM | −30.538 | 0.0023635 |
| 7410 | VAV2 | −30.535 | 0.0023635 |
| 167227 | DCP2 | −30.5 | 0.0023849 |
| 29015 | SLC43A3 | −30.477 | 0.0023967 |
| 10480 | EIF3M | −30.474 | 0.0023967 |
| 3106 | HLA-B | −30.439 | 0.0024222 |
| 55082 | ARGLU1 | −30.427 | 0.0024286 |
| 6256 | RXRA | −30.424 | 0.0024286 |
| 919 | CD247 | −30.395 | 0.0024504 |
| 23309 | SIN3B | −30.393 | 0.0024504 |
| 8029 | CUBN | −30.384 | 0.0024524 |
| 6721 | SREBF2 | −30.382 | 0.0024524 |
| 22827 | PUF60 | −30.356 | 0.0024695 |
| 2969 | GTF2I | −30.327 | 0.0024948 |
| 5184 | PEPD | −30.275 | 0.0025387 |
| 822 | CAPG | −30.246 | 0.0025613 |
| 56950 | SMYD2 | −30.238 | 0.0025613 |
| 6902 | TBCA | −30.235 | 0.0025613 |
| 3054 | HCFC1 | −30.232 | 0.0025613 |
| 307 | ANXA4 | −30.231 | 0.0025613 |
| 22870 | PPP6R1 | −30.219 | 0.0025694 |
| 51316 | PLAC8 | −30.201 | 0.0025836 |
| 51566 | ARMCX3 | −30.137 | 0.0026427 |
| 55341 | LSG1 | −30.128 | 0.0026481 |
| 55810 | FOXJ2 | −30.11 | 0.0026621 |
| 5250 | SLC25A3 | −30.099 | 0.0026701 |
| 8683 | SRSF9 | −30.058 | 0.0027048 |
| 25896 | INTS7 | −30.047 | 0.002712 |
| 26499 | PLEK2 | −30.018 | 0.0027397 |
| 79718 | TBL1XR1 | −30.003 | 0.0027525 |
| 4287 | ATXN3 | −29.953 | 0.002804 |
| 4615 | MYD88 | −29.926 | 0.0028249 |
| 4860 | PNP | −29.886 | 0.0028665 |
| 261726 | TIPRL | −29.866 | 0.0028846 |
| 355 | FAS | −29.845 | 0.0029044 |
| 55291 | PPP6R3 | −29.817 | 0.0029321 |
| 162427 | FAM134C | −29.806 | 0.0029403 |
| 708 | C1QBP | −29.773 | 0.0029737 |
| 3184 | HNRNPD | −29.77 | 0.0029737 |
| 3267 | AGFG1 | −29.759 | 0.0029787 |
| 25771 | TBC1D22A | −29.757 | 0.0029787 |
| 1808 | DPYSL2 | −29.741 | 0.0029885 |
| 9208 | LRRFIP1 | −29.723 | 0.0030017 |
| 10859 | LILRB1 | −29.718 | 0.0030017 |
| 60684 | TRAPPC11 | −29.716 | 0.0030017 |
| 27430 | MAT2B | −29.713 | 0.0030017 |
| 5261 | PHKG2 | −29.708 | 0.0030029 |
| 4478 | MSN | −29.687 | 0.0030232 |
| 51084 | CRYL1 | −29.676 | 0.0030318 |
| 51755 | CDK12 | −29.669 | 0.0030343 |
| 55207 | ARL8B | −29.666 | 0.0030343 |
| 2550 | GABBR1 | −29.629 | 0.003075 |
| 27069 | GHITM | −29.62 | 0.0030804 |
| 2729 | GCLC | −29.573 | 0.0031352 |
| 4772 | NFATC1 | −29.559 | 0.003147 |
| 3181 | HNRNPA2B1 | −29.544 | 0.003156 |
| 9341 | VAMP3 | −29.523 | 0.0031782 |
| 645 | BLVRB | −29.514 | 0.0031791 |
| 5293 | PIK3CD | −29.51 | 0.0031791 |
| 9589 | WTAP | −29.504 | 0.0031813 |
| 3190 | HNRNPK | −29.486 | 0.0031941 |
| 23335 | WDR7 | −29.455 | 0.0032189 |
| 5584 | PRKCI | −29.448 | 0.0032229 |
| 55689 | YEATS2 | −29.435 | 0.0032342 |
| 5579 | PRKCB | −29.414 | 0.0032563 |
| 4141 | MARS | −29.389 | 0.0032796 |
| 89781 | HPS4 | −29.372 | 0.0032968 |
| 23064 | SETX | −29.362 | 0.0033043 |
| 6746 | SSR2 | −29.302 | 0.0033804 |
| 9402 | GRAP2 | −29.256 | 0.0034268 |
| 6947 | TCN1 | −29.228 | 0.0034603 |
| 4967 | OGDH | −29.219 | 0.0034673 |
| 578 | BAK1 | −29.178 | 0.0035202 |
| 5982 | RFC2 | −29.158 | 0.0035432 |
| 5310 | PKD1 | −29.137 | 0.0035617 |
| 10066 | SCAMP2 | −29.118 | 0.0035789 |
| 84726 | PRRC2B | −29.117 | 0.0035789 |
| 28951 | TRIB2 | −29.09 | 0.0036074 |
| 4061 | LY6E | −29.052 | 0.003638 |
| 10623 | POLR3C | −29.047 | 0.003638 |
| 51368 | TEX264 | −29.046 | 0.003638 |
| 29109 | FHOD1 | −29.029 | 0.0036544 |
| 2879 | GPX4 | −29.008 | 0.0036652 |
| 5782 | PTPN12 | −28.996 | 0.0036696 |
| 3566 | IL4R | −28.993 | 0.0036696 |
| 7127 | TNFAIP2 | −28.986 | 0.0036743 |
| 60468 | BACH2 | −28.975 | 0.0036772 |
| 1847 | DUSP5 | −28.974 | 0.0036772 |
| 113251 | LARP4 | −28.972 | 0.0036772 |
| 55072 | RNF31 | −28.948 | 0.0036989 |
| 6904 | TBCD | −28.947 | 0.0036989 |
| 399665 | FAM102A | −28.923 | 0.0037213 |
| 833 | CARS | −28.921 | 0.0037213 |
| 5447 | POR | −28.906 | 0.0037382 |
| 3936 | LCP1 | −28.892 | 0.0037527 |
| 997 | CDC34 | −28.845 | 0.0038195 |
| 10963 | STIP1 | −28.808 | 0.0038716 |
| 80256 | FAM214B | −28.793 | 0.0038822 |
| 1385 | CREB1 | −28.787 | 0.0038832 |
| 64419 | MTMR14 | −28.785 | 0.0038832 |
| 80169 | CTC1 | −28.781 | 0.0038846 |
| 30001 | ERO1L | −28.774 | 0.0038899 |
| 28511 | NKIRAS2 | −28.755 | 0.0039071 |
| 1938 | EEF2 | −28.745 | 0.0039121 |
| 51098 | IFT52 | −28.743 | 0.0039121 |
| 7347 | UCHL3 | −28.741 | 0.0039121 |
| 272 | AMPD3 | −28.709 | 0.0039511 |
| 57610 | RANBP10 | −28.703 | 0.0039541 |

TABLE 3-continued

Complete list of differentially expressed genes.

| Entrez ID | Gene symbol (Name) | Combined Tstat | Combined Pval |
|---|---|---|---|
| 9869 | SETDB1 | −28.696 | 0.0039603 |
| 1974 | EIF4A2 | −28.679 | 0.0039726 |
| 6277 | S100A6 | −28.679 | 0.0039726 |
| 6279 | S100A8 | −28.677 | 0.0039726 |
| 6760 | SS18 | −28.67 | 0.0039773 |
| 6132 | RPL8 | −28.643 | 0.0040108 |
| 57698 | KIAA1598 | −28.642 | 0.0040108 |
| 3087 | HHEX | −28.628 | 0.0040273 |
| 2548 | GAA | −28.598 | 0.0040705 |
| 9775 | EIF4A3 | −28.562 | 0.004122 |
| 4090 | SMAD5 | −28.558 | 0.004122 |
| 7317 | UBA1 | −28.556 | 0.004122 |
| 92017 | SNX29 | −28.544 | 0.0041367 |
| 4363 | ABCC1 | −28.525 | 0.0041571 |
| 3055 | HCK | −28.521 | 0.0041571 |
| 55623 | THUMPD1 | −28.516 | 0.0041571 |
| 4758 | NEU1 | −28.514 | 0.0041571 |
| 54440 | SASH3 | −28.5 | 0.0041684 |
| 51510 | CHMP5 | −28.491 | 0.0041762 |
| 79752 | ZFAND1 | −28.484 | 0.0041825 |
| 7024 | TFCP2 | −28.466 | 0.0042074 |
| 974 | CD79B | −28.443 | 0.0042402 |
| 81603 | TRIM8 | −28.424 | 0.0042671 |
| 10282 | BET1 | −28.401 | 0.0042996 |
| 23603 | CORO1C | −28.398 | 0.0042996 |
| 22934 | RPIA | −28.387 | 0.0043054 |
| 8674 | VAMP4 | −28.363 | 0.0043396 |
| 1796 | DOK1 | −28.351 | 0.0043495 |
| 57194 | ATP10A | −28.335 | 0.0043724 |
| 5739 | PTGIR | −28.314 | 0.0044036 |
| 4066 | LYL1 | −28.306 | 0.0044061 |
| 8312 | AXIN1 | −28.305 | 0.0044061 |
| 64343 | AZI2 | −28.293 | 0.0044211 |
| 6729 | SRP54 | −28.272 | 0.0044492 |
| 80301 | PLEKHO2 | −28.27 | 0.0044492 |
| 10299 | MARCH6 | −28.253 | 0.0044742 |
| 7316 | UBC | −28.238 | 0.0044943 |
| 7318 | UBA7 | −28.233 | 0.0044985 |
| 55039 | TRMT12 | −28.177 | 0.0045934 |
| 29915 | HCFC2 | −28.173 | 0.0045943 |
| 11040 | PIM2 | −28.163 | 0.0046059 |
| 4609 | MYC | −28.158 | 0.0046084 |
| 8774 | NAPG | −28.152 | 0.0046084 |
| 6924 | TCEB3 | −28.15 | 0.0046084 |
| 51329 | ARL6IP4 | −28.148 | 0.0046084 |
| 4190 | MDH1 | −28.091 | 0.004683 |
| 79065 | ATG9A | −28.089 | 0.004683 |
| 6883 | TAF12 | −28.088 | 0.004683 |
| 23299 | BICD2 | −28.085 | 0.004683 |
| 3093 | UBE2K | −28.082 | 0.004683 |
| 55293 | UEVLD | −28.081 | 0.004683 |
| 79939 | SLC35E1 | −28.074 | 0.004689 |
| 23244 | PDS5A | −28.061 | 0.0047073 |
| 5691 | PSMB3 | −28.042 | 0.0047362 |
| 5777 | PTPN6 | −28.032 | 0.0047498 |
| 29086 | BABAM1 | −28.011 | 0.0047828 |
| 166 | AES | −27.986 | 0.0048254 |
| 51008 | ASCC1 | −27.976 | 0.0048533 |
| 3418 | IDH2 | −27.961 | 0.0048533 |
| 56983 | POGLUT1 | −27.961 | 0.0048533 |
| 8650 | NUMB | −27.949 | 0.0048696 |
| 2120 | ETV6 | −27.925 | 0.0049103 |
| 23276 | KLHL18 | −27.911 | 0.0049326 |
| 27230 | SERP1 | −27.896 | 0.0049548 |
| 3590 | IL11RA | −27.889 | 0.0049631 |
| 4173 | MCM4 | −27.843 | 0.0050416 |
| 51637 | C14orf166 | −27.838 | 0.0050438 |
| 2773 | GNAI3 | −27.83 | 0.0050468 |
| 3104 | ZBTB48 | −27.827 | 0.0050468 |
| 9467 | SH3BP5 | −27.789 | 0.005109 |
| 2242 | FES | −27.786 | 0.005109 |
| 8243 | SMC1A | −27.733 | 0.0051976 |
| 81689 | ISCA1 | −27.728 | 0.0052027 |
| 5886 | RAD23A | −27.723 | 0.0052043 |
| 10379 | IRF9 | −27.713 | 0.005213 |
| 2222 | FDFT1 | −27.707 | 0.0052153 |
| 2764 | GMFB | −27.702 | 0.0052153 |
| 55823 | VPS11 | −27.696 | 0.0052153 |
| 54902 | TTC19 | −27.693 | 0.0052153 |
| 4063 | LY9 | −27.692 | 0.0052153 |
| 7818 | DAP3 | −27.685 | 0.0052199 |
| 5426 | POLE | −27.681 | 0.0052199 |
| 64768 | IPPK | −27.68 | 0.0052199 |
| 5909 | RAP1GAP | −27.671 | 0.005233 |
| 7100 | TLR5 | −27.663 | 0.0052383 |
| 5119 | CHMP1A | −27.662 | 0.0052383 |
| 4601 | MXI1 | −27.638 | 0.0052804 |
| 3326 | HSP90AB1 | −27.607 | 0.0053394 |
| 4296 | MAP3K11 | −27.596 | 0.0053502 |
| 79980 | DSN1 | −27.596 | 0.0053502 |
| 55156 | ARMC1 | −27.587 | 0.0053556 |
| 301 | ANXA1 | −27.583 | 0.0053556 |
| 29894 | CPSF1 | −27.557 | 0.0053921 |
| 3394 | IRF8 | −27.552 | 0.0053921 |
| 6723 | SRM | −27.549 | 0.0053921 |
| 81611 | ANP32E | −27.544 | 0.0053921 |
| 9852 | EPM2AIP1 | −27.544 | 0.0053921 |
| 7433 | VIPR1 | −27.535 | 0.0054041 |
| 22887 | FOXJ3 | −27.502 | 0.0054639 |
| 3661 | IRF3 | −27.492 | 0.0054771 |
| 6595 | SMARCA2 | −27.455 | 0.0055362 |
| 64897 | C12orf43 | −27.453 | 0.0055362 |
| 284904 | SEC14L4 | −27.45 | 0.0055362 |
| 3015 | H2AFZ | −27.443 | 0.0055448 |
| 10527 | IPO7 | −27.389 | 0.0056436 |
| 3429 | IFI27 | −27.385 | 0.0056461 |
| 55164 | SHQ1 | −27.375 | 0.0056597 |
| 3934 | LCN2 | −27.371 | 0.0056597 |
| 26354 | GNL3 | −27.369 | 0.0056597 |
| 5613 | PRKX | −27.361 | 0.0056701 |
| 64118 | DUS1L | −27.358 | 0.0056701 |
| 2181 | ACSL3 | −27.331 | 0.0057194 |
| 6990 | DYNLT3 | −27.324 | 0.0057275 |
| 6636 | SNRPF | −27.301 | 0.0057664 |
| 8451 | CUL4A | −27.296 | 0.0057664 |
| 23762 | OSBP2 | −27.295 | 0.0057664 |
| 4720 | NDUFS2 | −27.291 | 0.0057664 |
| 8462 | KLF11 | −27.285 | 0.0057664 |
| 51701 | NLK | −27.272 | 0.0057899 |
| 9203 | ZMYM3 | −27.266 | 0.0057925 |
| 1716 | DGUOK | −27.264 | 0.0057925 |
| 200081 | TXLNA | −27.254 | 0.0057925 |
| 1389 | CREBL2 | −27.253 | 0.0057925 |
| 26034 | IPCEF1 | −27.253 | 0.0057925 |
| 3784 | KCNQ1 | −27.245 | 0.0057986 |
| 26119 | LDLRAP1 | −27.244 | 0.0057986 |
| 10092 | ARPC5 | −27.236 | 0.0058092 |
| 11336 | EXOC3 | −27.221 | 0.0058364 |
| 11171 | STRAP | −27.212 | 0.0058516 |
| 9184 | BUB3 | −27.176 | 0.0059296 |
| 3313 | HSPA9 | −27.127 | 0.0060305 |
| 23457 | ABCB9 | −27.103 | 0.0060816 |
| 1200 | TPP1 | −27.085 | 0.0061111 |
| 8295 | TRRAP | −27.072 | 0.0061294 |
| 1642 | DDB1 | −27.071 | 0.0061294 |
| 10947 | AP3M2 | −27.067 | 0.0061315 |
| 9129 | PRPF3 | −27.044 | 0.0061669 |
| 2208 | FCER2 | −27.039 | 0.006169 |
| 10460 | TACC3 | −27.035 | 0.006169 |
| 10627 | MYL12A | −27.034 | 0.006169 |
| 10723 | SLC12A7 | −27.027 | 0.0061798 |
| 91860 | CALML4 | −27.01 | 0.0062129 |
| 4678 | NASP | −26.979 | 0.006258 |
| 9600 | PITPNM1 | −26.977 | 0.006258 |
| 10367 | MICU1 | −26.975 | 0.006258 |
| 6237 | RRAS | −26.972 | 0.006258 |
| 8891 | EIF2B3 | −26.971 | 0.006258 |
| 1408 | CRY2 | −26.968 | 0.0062589 |
| 23353 | SUN1 | −26.952 | 0.0062837 |
| 60488 | MRPS35 | −26.946 | 0.0062884 |

TABLE 3-continued

Complete list of differentially expressed genes.

| Entrez ID | Gene symbol (Name) | Combined Tstat | Combined Pval |
|---|---|---|---|
| 10549 | PRDX4 | −26.944 | 0.0062884 |
| 152006 | RNF38 | −26.931 | 0.0063147 |
| 80895 | ILKAP | −26.928 | 0.0063157 |
| 6293 | VPS52 | −26.922 | 0.0063222 |
| 900 | CCNG1 | −26.902 | 0.0063665 |
| 9993 | DGCR2 | −26.888 | 0.0063776 |
| 54606 | DDX56 | −26.876 | 0.0064004 |
| 6302 | TSPAN31 | −26.869 | 0.0064043 |
| 26190 | FBXW2 | −26.863 | 0.0064129 |
| 1176 | AP3S1 | −26.851 | 0.0064279 |
| 5685 | PSMA4 | −26.845 | 0.0064303 |
| 10128 | LRPPRC | −26.845 | 0.0064303 |
| 51074 | APIP | −26.839 | 0.0064357 |
| 55114 | ARHGAP17 | −26.827 | 0.0064605 |
| 3702 | ITK | −26.818 | 0.0064687 |
| 10482 | NXF1 | −26.808 | 0.0064771 |
| 29102 | DROSHA | −26.806 | 0.0064771 |
| 3726 | JUNB | −26.803 | 0.0064771 |
| 9044 | BTAF1 | −26.786 | 0.0065036 |
| 517 | ATP5G2 | −26.78 | 0.0065036 |
| 1843 | DUSP1 | −26.779 | 0.0065036 |
| 9150 | CTDP1 | −26.752 | 0.0065592 |
| 8775 | NAPA | −26.73 | 0.0066028 |
| 50807 | ASAP1 | −26.728 | 0.0066028 |
| 3759 | KCNJ2 | −26.726 | 0.0066028 |
| 10900 | RUNDC3A | −26.723 | 0.0066038 |
| 10404 | CPQ | −26.705 | 0.0066447 |
| 55738 | ARFGAP1 | −26.693 | 0.0066679 |
| 8662 | EIF3B | −26.69 | 0.0066687 |
| 5524 | PPP2R4 | −26.668 | 0.0067123 |
| 51279 | C1RL | −26.647 | 0.0067486 |
| 23171 | GPD1L | −26.586 | 0.006904 |
| 29916 | SNX11 | −26.582 | 0.0069059 |
| 55884 | WSB2 | −26.57 | 0.0069302 |
| 6480 | ST6GAL1 | −26.565 | 0.0069361 |
| 30844 | EHD4 | −26.553 | 0.0069623 |
| 8408 | ULK1 | −26.544 | 0.0069793 |
| 7453 | WARS | −26.535 | 0.0069838 |
| 53944 | CSNK1G1 | −26.534 | 0.0069838 |
| 103 | ADAR | −26.531 | 0.0069848 |
| 4123 | MAN2C1 | −26.525 | 0.0069949 |
| 23164 | MPRIP | −26.521 | 0.006996 |
| 9451 | EIF2AK3 | −26.518 | 0.0069969 |
| 10280 | SIGMAR1 | −26.513 | 0.007005 |
| 91137 | SLC25A46 | −26.51 | 0.0070061 |
| 60685 | ZFAND3 | −26.502 | 0.0070175 |
| 5610 | EIF2AK2 | −26.5 | 0.0070175 |
| 5598 | MAPK7 | −26.496 | 0.007022 |
| 8664 | EIF3D | −26.474 | 0.0070729 |
| 7726 | TRIM26 | −26.47 | 0.0070729 |
| 25941 | TPGS2 | −26.467 | 0.0070729 |
| 261734 | NPHP4 | −26.466 | 0.0070729 |
| 133 | ADM | −26.457 | 0.0070902 |
| 54622 | ARL15 | −26.455 | 0.0070902 |
| 63925 | ZNF335 | −26.434 | 0.0071398 |
| 3431 | SP110 | −26.43 | 0.0071448 |
| 6272 | SORT1 | −26.416 | 0.0071764 |
| 10954 | PDIA5 | −26.411 | 0.0071837 |
| 55249 | YY1AP1 | −26.392 | 0.0072284 |
| 80152 | CENPT | −26.384 | 0.0072429 |
| 80279 | CDK5RAP3 | −26.38 | 0.0072475 |
| 3460 | IFNGR2 | −26.371 | 0.0072649 |
| 54664 | TMEM106B | −26.358 | 0.0072876 |
| 55101 | ATP5SL | −26.357 | 0.0072876 |
| 1981 | EIF4G1 | −26.355 | 0.0072876 |
| 5747 | PTK2 | −26.345 | 0.00731 |
| 11180 | WDR6 | −26.329 | 0.0073438 |
| 10221 | TRIB1 | −26.328 | 0.0073438 |
| 6571 | SLC18A2 | −26.312 | 0.0073812 |
| 84164 | ASCC2 | −26.304 | 0.0073978 |
| 84061 | MAGT1 | −26.273 | 0.0074712 |
| 7297 | TYK2 | −26.257 | 0.0075 |
| 1431 | CS | −26.256 | 0.0075 |
| 2108 | ETFA | −26.246 | 0.007521 |
| 2733 | GLE1 | −26.24 | 0.0075299 |
| 27044 | SND1 | −26.236 | 0.0075329 |
| 79621 | RNASEH2B | −26.232 | 0.0075366 |
| 203197 | C9orf91 | −26.204 | 0.0076073 |
| 1536 | CYBB | −26.192 | 0.0076297 |
| 78991 | PCYOX1L | −26.189 | 0.0076297 |
| 10270 | AKAP8 | −26.188 | 0.0076297 |
| 30 | ACAA1 | −26.185 | 0.0076297 |
| 10445 | MCRS1 | −26.173 | 0.0076586 |
| 80218 | NAA50 | −26.169 | 0.0076626 |
| 54805 | CNNM2 | −26.167 | 0.0076626 |
| 2004 | ELK3 | −26.158 | 0.0076809 |
| 7536 | SF1 | −26.153 | 0.0076864 |
| 4354 | MPP1 | −26.149 | 0.0076905 |
| 124583 | CANT1 | −26.147 | 0.0076905 |
| 27332 | ZNF638 | −26.114 | 0.0077815 |
| 1432 | MAPK14 | −26.097 | 0.0078275 |
| 3148 | HMGB2 | −26.086 | 0.0078509 |
| 9314 | KLF4 | −26.081 | 0.0078509 |
| 9654 | TTLL4 | −26.077 | 0.0078509 |
| 8883 | NAE1 | −26.076 | 0.0078509 |
| 9181 | ARHGEF2 | −26.076 | 0.0078509 |
| 22902 | RUFY3 | −26.073 | 0.0078535 |
| 4659 | PPP1R12A | −26.062 | 0.0078736 |
| 7111 | TMOD1 | −26.049 | 0.007893 |
| 8260 | NAA10 | −26.049 | 0.007893 |
| 483 | ATP1B3 | −26.047 | 0.007893 |
| 27032 | ATP2C1 | −26.042 | 0.0078995 |
| 7071 | KLF10 | −26.019 | 0.0079634 |
| 55297 | CCDC91 | −26.011 | 0.0079794 |
| 51006 | SLC35C2 | −26.008 | 0.0079814 |
| 11078 | TRIOBP | −26.001 | 0.0079861 |
| 4713 | NDUFB7 | −25.999 | 0.0079861 |
| 6891 | TAP2 | −25.982 | 0.0080248 |
| 79573 | TTC13 | −25.981 | 0.0080248 |
| 8898 | MTMR2 | −25.975 | 0.0080367 |
| 54436 | SH3TC1 | −25.968 | 0.0080502 |
| 199 | AIF1 | −25.943 | 0.0081228 |
| 9738 | CCP110 | −25.885 | 0.008295 |
| 27183 | VPS4A | −25.874 | 0.0083224 |
| 5690 | PSMB2 | −25.868 | 0.0083316 |
| 1232 | CCR3 | −25.863 | 0.0083415 |
| 6446 | SGK1 | −25.852 | 0.0083555 |
| 2581 | GALC | −25.834 | 0.008403 |
| 5330 | PLCB2 | −25.826 | 0.0084203 |
| 7690 | ZNF131 | −25.818 | 0.0084359 |
| 55148 | UBR7 | −25.816 | 0.0084359 |
| 3932 | LCK | −25.813 | 0.0084382 |
| 55827 | DCAF6 | −25.789 | 0.0085086 |
| 7443 | VRK1 | −25.78 | 0.0085235 |
| 3043 | HBB | −25.769 | 0.0085512 |
| 56965 | PARP6 | −25.76 | 0.0085612 |
| 6427 | SRSF2 | −25.758 | 0.0085612 |
| 23214 | XPO6 | −25.712 | 0.0086809 |
| 8804 | CREG1 | −25.711 | 0.0086809 |
| 552889 | ATXN7L3B | −25.71 | 0.0086809 |
| 10295 | BCKDK | −25.689 | 0.008737 |
| 25839 | COG4 | −25.685 | 0.0087405 |
| 65980 | BRD9 | −25.667 | 0.0087683 |
| 57050 | UTP3 | −25.654 | 0.0087859 |
| 955 | ENTPD6 | −25.654 | 0.0087859 |
| 9325 | TRIP4 | −25.652 | 0.0087859 |
| 84516 | DCTN5 | −25.628 | 0.008843 |
| 26065 | LSM14A | −25.611 | 0.0088781 |
| 7342 | UBP1 | −25.603 | 0.0088825 |
| 7716 | VEZF1 | −25.601 | 0.0088825 |
| 2643 | GCH1 | −25.601 | 0.0088825 |
| 51728 | POLR3K | −25.586 | 0.0089219 |
| 29959 | NRBP1 | −25.583 | 0.0089221 |
| 51108 | METTL9 | −25.569 | 0.0089625 |
| 79134 | TMEM185B | −25.518 | 0.0091319 |
| 6814 | STXBP3 | −25.517 | 0.0091319 |
| 64210 | MMS19 | −25.489 | 0.0092145 |
| 3268 | AGFG2 | −25.476 | 0.0092479 |
| 55681 | SCYL2 | −25.475 | 0.0092479 |
| 10134 | BCAP31 | −25.468 | 0.0092621 |

TABLE 3-continued

Complete list of differentially expressed genes.

| Entrez ID | Gene symbol (Name) | Combined Tstat | Combined Pval |
|---|---|---|---|
| 5606 | MAP2K3 | −25.461 | 0.0092784 |
| 9810 | RNF40 | −25.445 | 0.0093124 |
| 55000 | TUG1 | −25.441 | 0.0093152 |
| 115353 | LRRC42 | −25.411 | 0.0094161 |
| 5550 | PREP | −25.409 | 0.0094161 |
| 5696 | PSMB8 | −25.394 | 0.0094626 |
| 682 | BSG | −25.387 | 0.0094767 |
| 10691 | GMEB1 | −25.382 | 0.0094767 |
| 10127 | ZNF263 | −25.381 | 0.0094767 |
| 9862 | MED24 | −25.376 | 0.0094843 |
| 7421 | VDR | −25.361 | 0.009532 |
| 22916 | NCBP2 | −25.349 | 0.009566 |
| 6182 | MRPL12 | −25.346 | 0.0095713 |
| 327 | APEH | −25.332 | 0.0096029 |
| 834 | CASP1 | −25.32 | 0.0096224 |
| 4076 | CAPRIN1 | −25.32 | 0.0096224 |
| 55863 | TMEM126B | −25.31 | 0.0096442 |
| 1236 | CCR7 | −25.309 | 0.0096442 |
| 51056 | LAP3 | −25.305 | 0.0096499 |
| 317662 | FAM149B1 | −25.29 | 0.0096913 |
| 5682 | PSMA1 | −25.28 | 0.0097201 |
| 596 | BCL2 | −25.266 | 0.0097619 |
| 9217 | VAPB | −25.264 | 0.0097619 |
| 6185 | RPN2 | −25.259 | 0.0097714 |
| 27247 | NFU1 | −25.247 | 0.0098104 |
| 26039 | SS18L1 | −25.234 | 0.0098413 |
| 3185 | HNRNPF | −25.231 | 0.0098413 |
| 210 | ALAD | −25.227 | 0.0098413 |
| 55803 | ADAP2 | −25.226 | 0.0098413 |
| 51564 | HDAC7 | −25.224 | 0.0098413 |
| 81542 | TMX1 | −25.222 | 0.0098413 |
| 9531 | BAG3 | −25.209 | 0.0098719 |
| 9039 | UBA3 | −25.189 | 0.009942 |
| 7095 | SEC62 | −25.186 | 0.0099435 |
| 5925 | RB1 | −25.176 | 0.0099732 |
| 8209 | C21orf33 | −25.161 | 0.010013 |
| 8893 | EIF2B5 | −25.144 | 0.01006 |
| 7385 | UQCRC2 | −25.133 | 0.010094 |
| 9990 | SLC12A6 | −25.128 | 0.010102 |
| 25966 | C2CD2 | −25.127 | 0.010102 |
| 829 | CAPZA1 | −25.114 | 0.010126 |
| 55719 | FAM178A | −25.091 | 0.010206 |
| 3836 | KPNA1 | −25.083 | 0.010229 |
| 9275 | BCL7B | −25.07 | 0.01027 |
| 65220 | NADK | −25.066 | 0.010277 |
| 6398 | SECTM1 | −25.053 | 0.010318 |
| 113 | ADCY7 | −25.052 | 0.010318 |
| 23324 | MAN2B2 | −25.044 | 0.010338 |
| 1994 | ELAVL1 | −25.032 | 0.010368 |
| 56901 | NDUFA4L2 | −25.028 | 0.010377 |
| 221 | ALDH3B1 | −25.023 | 0.010385 |
| 54708 | MARCH5 | −25.008 | 0.010427 |
| 55167 | MSL2 | −24.999 | 0.010448 |
| 8367 | HIST1H4E | −24.998 | 0.010448 |
| 2533 | FYB | −24.995 | 0.010448 |
| 79745 | CLIP4 | −24.994 | 0.010448 |
| 58488 | PCTP | −24.985 | 0.01047 |
| 23152 | CIC | −24.984 | 0.01047 |
| 163 | AP2B1 | −24.981 | 0.010472 |
| 11044 | PAPD7 | −24.979 | 0.010472 |
| 760 | CA2 | −24.976 | 0.010475 |
| 10363 | HMG20A | −24.971 | 0.010487 |
| 4976 | OPA1 | −24.965 | 0.010491 |
| 113791 | PIK3IP1 | −24.951 | 0.010533 |
| 8533 | COPS3 | −24.946 | 0.010541 |
| 6478 | SIAH2 | −24.934 | 0.010582 |
| 11034 | DSTN | −24.923 | 0.010616 |
| 27005 | USP21 | −24.913 | 0.010648 |
| 9552 | SPAG7 | −24.898 | 0.010684 |
| 9782 | MATR3 | −24.895 | 0.010685 |
| 29082 | CHMP4A | −24.891 | 0.010687 |
| 6843 | VAMP1 | −24.89 | 0.010687 |
| 27074 | LAMP3 | −24.888 | 0.010689 |
| 6184 | RPN1 | −24.876 | 0.010712 |
| 79654 | HECTD3 | −24.875 | 0.010712 |
| 3257 | HPS1 | −24.873 | 0.010713 |
| 6634 | SNRPD3 | −24.855 | 0.010767 |
| 3101 | HK3 | −24.848 | 0.010785 |
| 26017 | FAM32A | −24.847 | 0.010785 |
| 29926 | GMPPA | −24.841 | 0.010798 |
| 1032 | CDKN2D | −24.835 | 0.010816 |
| 79096 | C11orf49 | −24.832 | 0.010817 |
| 27020 | NPTN | −24.83 | 0.010819 |
| 23191 | CYFIP1 | −24.825 | 0.010829 |
| 80833 | APOL3 | −24.804 | 0.010885 |
| 1606 | DGKA | −24.803 | 0.010885 |
| 25792 | CIZ1 | −24.8 | 0.010885 |
| 3162 | HMOX1 | −24.798 | 0.010885 |
| 25977 | NECAP1 | −24.797 | 0.010885 |
| 6901 | TAZ | −24.795 | 0.010885 |
| 8115 | TCL1A | −24.794 | 0.010885 |
| 7009 | TMBIM6 | −24.792 | 0.010885 |
| 27240 | SIT1 | −24.78 | 0.010917 |
| 388 | RHOB | −24.779 | 0.010917 |
| 3684 | ITGAM | −24.775 | 0.010925 |
| 55788 | LMBRD1 | −24.764 | 0.010962 |
| 9474 | ATG5 | −24.75 | 0.01101 |
| 9489 | PGS1 | −24.748 | 0.01101 |
| 10312 | TCIRG1 | −24.747 | 0.01101 |
| 22818 | COPZ1 | −24.722 | 0.011098 |
| 2739 | GLO1 | −24.715 | 0.011117 |
| 81688 | C6orf62 | −24.708 | 0.011127 |
| 6934 | TCF7L2 | −24.704 | 0.011135 |
| 54941 | RNF125 | −24.698 | 0.011153 |
| 11157 | LSM6 | −24.691 | 0.011175 |
| 9049 | AIP | −24.672 | 0.011248 |
| 80740 | LY6G6C | −24.658 | 0.011296 |
| 256987 | SERINC5 | −24.657 | 0.011296 |
| 1089 | CEACAM4 | −24.648 | 0.011323 |
| 51069 | MRPL2 | −24.64 | 0.011345 |
| 10019 | SH2B3 | −24.639 | 0.011345 |
| 523 | ATP6V1A | −24.623 | 0.011396 |
| 57379 | AICDA | −24.61 | 0.011434 |
| 1211 | CLTA | −24.591 | 0.0115 |
| 967 | CD63 | −24.579 | 0.01154 |
| 80142 | PTGES2 | −24.577 | 0.01154 |
| 8019 | BRD3 | −24.574 | 0.011546 |
| 55092 | TMEM51 | −24.566 | 0.011561 |
| 7386 | UQCRFS1 | −24.557 | 0.011595 |
| 55791 | LRIF1 | −24.547 | 0.011618 |
| 64848 | YTHDC2 | −24.54 | 0.011639 |
| 7133 | TNFRSF1B | −24.538 | 0.011639 |
| 50856 | CLEC4A | −24.528 | 0.011674 |
| 22948 | CCT5 | −24.525 | 0.011674 |
| 57215 | THAP11 | −24.524 | 0.011674 |
| 6342 | SCP2 | −24.52 | 0.01168 |
| 2057 | EPOR | −24.49 | 0.01179 |
| 4170 | MCL1 | −24.46 | 0.011899 |
| 4055 | LTBR | −24.44 | 0.011962 |
| 10598 | AHSA1 | −24.439 | 0.011962 |
| 4689 | NCF4 | −24.437 | 0.011962 |
| 1810 | DR1 | −24.436 | 0.011962 |
| 51031 | GLOD4 | −24.434 | 0.011962 |
| 4522 | MTHFD1 | −24.431 | 0.011962 |
| 50717 | DCAF8 | −24.43 | 0.011962 |
| 55312 | RFK | −24.413 | 0.012028 |
| 6646 | SOAT1 | −24.409 | 0.012035 |
| 3981 | LIG4 | −24.404 | 0.012045 |
| 51465 | UBE2J1 | −24.403 | 0.012045 |
| 26073 | POLDIP2 | −24.387 | 0.012095 |
| 7165 | TPD52L2 | −24.386 | 0.012095 |
| 54453 | RIN2 | −24.382 | 0.012103 |
| 63901 | FAM111A | −24.368 | 0.01214 |
| 7019 | TFAM | −24.368 | 0.01214 |
| 9123 | SLC16A3 | −24.358 | 0.012163 |
| 22919 | MAPRE1 | −24.357 | 0.012163 |
| 8202 | NCOA3 | −24.356 | 0.012163 |
| 4898 | NRD1 | −24.348 | 0.012194 |
| 6464 | SHC1 | −24.34 | 0.012208 |
| 11046 | SLC35D2 | −24.336 | 0.012216 |

TABLE 3-continued

Complete list of differentially expressed genes.

| Entrez ID | Gene symbol (Name) | Combined Tstat | Combined Pval |
|---|---|---|---|
| 2588 | GALNS | −24.335 | 0.012216 |
| 57205 | ATP10D | −24.327 | 0.012239 |
| 54187 | NANS | −24.325 | 0.012239 |
| 6767 | ST13 | −24.311 | 0.012292 |
| 27130 | INVS | −24.31 | 0.012292 |
| 2015 | EMR1 | −24.299 | 0.012327 |
| 5125 | PCSK5 | −24.254 | 0.012514 |
| 9466 | IL27RA | −24.229 | 0.012623 |
| 1130 | LYST | −24.22 | 0.012657 |
| 9218 | VAPA | −24.206 | 0.012703 |
| 5023 | P2RX1 | −24.205 | 0.012703 |
| 1017 | CDK2 | −24.201 | 0.012703 |
| 2323 | FLT3LG | −24.2 | 0.012703 |
| 2734 | GLG1 | −24.196 | 0.012713 |
| 57591 | MKL1 | −24.191 | 0.01273 |
| 3611 | ILK | −24.182 | 0.012763 |
| 57140 | RNPEPL1 | −24.158 | 0.012872 |
| 3108 | HLA-DMA | −24.128 | 0.012996 |
| 4839 | NOP2 | −24.127 | 0.012996 |
| 9191 | DEDD | −24.125 | 0.012996 |
| 3783 | KCNN4 | −24.119 | 0.013005 |
| 112869 | CCDC101 | −24.118 | 0.013005 |
| 51304 | ZDHHC3 | −24.117 | 0.013005 |
| 51218 | GLRX5 | −24.112 | 0.013017 |
| 7846 | TUBA1A | −24.101 | 0.013066 |
| 8890 | EIF2B4 | −24.097 | 0.013074 |
| 8915 | BCL10 | −24.087 | 0.013112 |
| 962 | CD48 | −24.078 | 0.013132 |
| 2624 | GATA2 | −24.078 | 0.013132 |
| 5859 | QARS | −24.074 | 0.013132 |
| 3064 | HTT | −24.073 | 0.013132 |
| 6451 | SH3BGRL | −24.073 | 0.013132 |
| 6541 | SLC7A1 | −24.061 | 0.013182 |
| 10913 | EDAR | −24.052 | 0.013206 |
| 375035 | SFT2D2 | −24.047 | 0.013212 |
| 3068 | HDGF | −24.045 | 0.013212 |
| 57130 | ATP13A1 | −24.036 | 0.01324 |
| 4000 | LMNA | −24.028 | 0.013268 |
| 994 | CDC25B | −24.024 | 0.013277 |
| 11108 | PRDM4 | −24.009 | 0.013345 |
| 7866 | IFRD2 | −23.995 | 0.0134 |
| 1178 | CLC | −23.992 | 0.0134 |
| 178 | AGL | −23.991 | 0.0134 |
| 27352 | SGSM3 | −23.99 | 0.0134 |
| 4953 | ODC1 | −23.982 | 0.013433 |
| 154881 | KCTD7 | −23.97 | 0.013484 |
| 51571 | FAM49B | −23.958 | 0.013535 |
| 51573 | GDE1 | −23.952 | 0.013556 |
| 26051 | PPP1R16B | −23.946 | 0.013578 |
| 79144 | PPDPF | −23.937 | 0.013613 |
| 9159 | PCSK7 | −23.934 | 0.013619 |
| 9557 | CHD1L | −23.928 | 0.01364 |
| 55626 | AMBRA1 | −23.926 | 0.01364 |
| 10113 | PREB | −23.921 | 0.013657 |
| 9169 | SCAF11 | −23.91 | 0.013703 |
| 4899 | NRF1 | −23.898 | 0.013737 |
| 23478 | SEC11A | −23.885 | 0.013776 |
| 81537 | SGPP1 | −23.884 | 0.013776 |
| 25804 | LSM4 | −23.872 | 0.013824 |
| 286 | ANK1 | −23.871 | 0.013824 |
| 528 | ATP6V1C1 | −23.865 | 0.013846 |
| 321 | APBA2 | −23.863 | 0.013846 |
| 29957 | SLC25A24 | −23.858 | 0.013864 |
| 5912 | RAP2B | −23.845 | 0.013909 |
| 9935 | MAFB | −23.842 | 0.013909 |
| 6734 | SRPR | −23.841 | 0.013909 |
| 7296 | TXNRD1 | −23.839 | 0.01391 |
| 9019 | MPZL1 | −23.837 | 0.01391 |
| 6744 | SSFA2 | −23.826 | 0.013944 |
| 140459 | ASB6 | −23.825 | 0.013944 |
| 1116 | CHI3L1 | −23.825 | 0.013944 |
| 79228 | THOC6 | −23.818 | 0.01397 |
| 4790 | NFKB1 | −23.807 | 0.01402 |
| 57062 | DDX24 | −23.802 | 0.014027 |
| 60314 | C12orf10 | −23.8 | 0.014027 |
| 10802 | SEC24A | −23.8 | 0.014027 |
| 217 | ALDH2 | −23.795 | 0.014032 |
| 6240 | RRM1 | −23.795 | 0.014032 |
| 8935 | SKAP2 | −23.792 | 0.014036 |
| 80347 | COASY | −23.788 | 0.014049 |
| 51177 | PLEKHO1 | −23.782 | 0.014066 |
| 1519 | CTSO | −23.781 | 0.014066 |
| 3609 | ILF3 | −23.773 | 0.0141 |
| 4660 | PPP1R12B | −23.766 | 0.014123 |
| 79813 | EHMT1 | −23.764 | 0.014126 |
| 4938 | OAS1 | −23.759 | 0.014129 |
| 11329 | STK38 | −23.759 | 0.014129 |
| 27090 | ST6GALNAC4 | −23.757 | 0.014129 |
| 11022 | TDRKH | −23.733 | 0.014253 |
| 9961 | MVP | −23.724 | 0.014282 |
| 7145 | TNS1 | −23.724 | 0.014282 |
| 8818 | DPM2 | −23.721 | 0.014287 |
| 102 | ADAM10 | −23.713 | 0.0143 |
| 23198 | PSME4 | −23.712 | 0.0143 |
| 11186 | RASSF1 | −23.708 | 0.014316 |
| 11213 | IRAK3 | −23.693 | 0.014384 |
| 22794 | CASC3 | −23.687 | 0.014406 |
| 64422 | ATG3 | −23.673 | 0.014454 |
| 7090 | TLE3 | −23.666 | 0.014479 |
| 6873 | TAF2 | −23.657 | 0.014521 |
| 26118 | WSB1 | −23.652 | 0.014537 |
| 10116 | FEM1B | −23.65 | 0.014537 |
| 3071 | NCKAP1L | −23.648 | 0.014541 |
| 9665 | KIAA0430 | −23.636 | 0.014594 |
| 6830 | SUPT6H | −23.624 | 0.014653 |
| 5151 | PDE8A | −23.593 | 0.014807 |
| 6894 | TARBP1 | −23.567 | 0.014942 |
| 7336 | UBE2V2 | −23.565 | 0.014942 |
| 27440 | CECR5 | −23.543 | 0.01506 |
| 55343 | SLC35C1 | −23.519 | 0.015173 |
| 10857 | PGRMC1 | −23.512 | 0.015173 |
| 7706 | TRIM25 | −23.508 | 0.015173 |
| 7059 | THBS3 | −23.507 | 0.015173 |
| 550 | AUP1 | −23.506 | 0.015173 |
| 79073 | TMEM109 | −23.504 | 0.015173 |
| 4200 | ME2 | −23.502 | 0.015173 |
| 25840 | METTL7A | −23.49 | 0.015232 |
| 7292 | TNFSF4 | −23.472 | 0.015315 |
| 7574 | ZNF26 | −23.47 | 0.015319 |
| 28973 | MRPS18B | −23.466 | 0.015332 |
| 4318 | MMP9 | −23.456 | 0.01538 |
| 1053 | CEBPE | −23.451 | 0.01539 |
| 7535 | ZAP70 | −23.45 | 0.01539 |
| 51176 | LEF1 | −23.433 | 0.015479 |
| 55032 | SLC35A5 | −23.427 | 0.015499 |
| 79961 | DENND2D | −23.418 | 0.01551 |
| 92856 | IMP4 | −23.418 | 0.01551 |
| 25799 | ZNF324 | −23.417 | 0.01551 |
| 9612 | NCOR2 | −23.412 | 0.015524 |
| 56913 | C1GALT1 | −23.407 | 0.015539 |
| 2766 | GMPR | −23.389 | 0.015623 |
| 2230 | FDX1 | −23.388 | 0.015623 |
| 5093 | PCBP1 | −23.384 | 0.015638 |
| 25915 | NDUFAF3 | −23.369 | 0.015685 |
| 55717 | WDR11 | −23.369 | 0.015685 |
| 23310 | NCAPD3 | −23.361 | 0.015718 |
| 26469 | PTPN18 | −23.358 | 0.015718 |
| 4064 | CD180 | −23.356 | 0.015718 |
| 4524 | MTHFR | −23.355 | 0.015718 |
| 54811 | ZNF562 | −23.352 | 0.015729 |
| 55769 | ZNF83 | −23.342 | 0.015763 |
| 5799 | PTPRN2 | −23.334 | 0.015784 |
| 51021 | MRPS16 | −23.334 | 0.015784 |
| 65125 | WNK1 | −23.333 | 0.015784 |
| 51474 | LIMA1 | −23.318 | 0.015855 |
| 10077 | TSPAN32 | −23.31 | 0.015894 |
| 10014 | HDAC5 | −23.307 | 0.015898 |
| 7052 | TGM2 | −23.301 | 0.015921 |
| 7001 | PRDX2 | −23.296 | 0.015943 |
| 5335 | PLCG1 | −23.284 | 0.015993 |

TABLE 3-continued

Complete list of differentially expressed genes.

| Entrez ID | Gene symbol (Name) | Combined Tstat | Combined Pval |
|---|---|---|---|
| 4303 | FOXO4 | −23.266 | 0.01609 |
| 56905 | C15orf39 | −23.263 | 0.016097 |
| 81892 | SLIRP | −23.257 | 0.016123 |
| 9209 | LRRFIP2 | −23.25 | 0.016134 |
| 29927 | SEC61A1 | −23.25 | 0.016134 |
| 8509 | NDST2 | −23.23 | 0.016246 |
| 9138 | ARHGEF1 | −23.212 | 0.016351 |
| 9398 | CD101 | −23.206 | 0.016369 |
| 3707 | ITPKB | −23.205 | 0.016369 |
| 81544 | GDPD5 | −23.202 | 0.016374 |
| 4277 | MICB | −23.198 | 0.016386 |
| 3182 | HNRNPAB | −23.187 | 0.016444 |
| 4292 | MLH1 | −23.185 | 0.016445 |
| 2060 | EPS15 | −23.179 | 0.016471 |
| 27075 | TSPAN13 | −23.174 | 0.016484 |
| 79089 | TMUB2 | −23.174 | 0.016484 |
| 6428 | SRSF3 | −23.165 | 0.016517 |
| 6050 | RNH1 | −23.153 | 0.016579 |
| 1540 | CYLD | −23.151 | 0.016584 |
| 4940 | OAS3 | −23.135 | 0.016657 |
| 7030 | TFE3 | −23.133 | 0.016663 |
| 1616 | DAXX | −23.121 | 0.016711 |
| 6687 | SPG7 | −23.118 | 0.016711 |
| 9445 | ITM2B | −23.117 | 0.016711 |
| 1072 | CFL1 | −23.116 | 0.016711 |
| 4245 | MGAT1 | −23.105 | 0.016751 |
| 6715 | SRD5A1 | −23.104 | 0.016751 |
| 283232 | TMEM80 | −23.095 | 0.016795 |
| 9050 | PSTPIP2 | −23.094 | 0.016795 |
| 26277 | TINF2 | −23.088 | 0.016808 |
| 3281 | HSBP1 | −23.077 | 0.016867 |
| 6448 | SGSH | −23.072 | 0.016888 |
| 25782 | RAB3GAP2 | −23.058 | 0.016968 |
| 6158 | RPL28 | −23.055 | 0.016977 |
| 3577 | CXCR1 | −23.049 | 0.017 |
| 6708 | SPTA1 | −23.043 | 0.017026 |
| 51360 | MBTPS2 | −23.04 | 0.017033 |
| 27040 | LAT | −23.037 | 0.017033 |
| 23193 | GANAB | −23.037 | 0.017033 |
| 53635 | PTOV1 | −23.032 | 0.017056 |
| 79091 | METTL22 | −23.026 | 0.017084 |
| 31 | ACACA | −23.015 | 0.01714 |
| 9731 | CEP104 | −23.009 | 0.017168 |
| 6641 | SNTB1 | −23.006 | 0.017175 |
| 8766 | RAB11A | −22.997 | 0.017211 |
| 2258 | FGF13 | −22.995 | 0.017213 |
| 6590 | SLPI | −22.977 | 0.017321 |
| 2316 | FLNA | −22.971 | 0.017345 |
| 51094 | ADIPOR1 | −22.965 | 0.017377 |
| 10289 | EIF1B | −22.954 | 0.017421 |
| 23102 | TBC1D2B | −22.953 | 0.017421 |
| 26273 | FBXO3 | −22.951 | 0.017421 |
| 5476 | CTSA | −22.946 | 0.017477 |
| 8718 | TNFRSF25 | −22.938 | 0.017481 |
| 8436 | SDPR | −22.934 | 0.01749 |
| 7298 | TYMS | −22.933 | 0.01749 |
| 402055 | SRRD | −22.932 | 0.017491 |
| 200576 | PIKFYVE | −22.927 | 0.017504 |
| 57506 | MAVS | −22.926 | 0.017504 |
| 4140 | MARK3 | −22.923 | 0.017505 |
| 6908 | TBP | −22.922 | 0.017505 |
| 56257 | MEPCE | −22.921 | 0.017505 |
| 8888 | MCM3AP | −22.916 | 0.017522 |
| 566 | AZU1 | −22.913 | 0.01753 |
| 8315 | BRAP | −22.906 | 0.017558 |
| 2592 | GALT | −22.904 | 0.017558 |
| 55813 | UTP6 | −22.904 | 0.017558 |
| 55327 | LIN7C | −22.9 | 0.017572 |
| 4705 | NDUFA10 | −22.897 | 0.017577 |
| 10953 | TOMM34 | −22.893 | 0.017577 |
| 81555 | YIPF5 | −22.892 | 0.017577 |
| 7109 | TRAPPC10 | −22.889 | 0.017583 |
| 10525 | HYOU1 | −22.884 | 0.017594 |
| 55796 | MBNL3 | −22.882 | 0.017596 |
| 9855 | FARP2 | −22.875 | 0.017632 |
| 23118 | TAB2 | −22.848 | 0.017777 |
| 3916 | LAMP1 | −22.828 | 0.017888 |
| 4311 | MME | −22.823 | 0.017909 |
| 5717 | PSMD11 | −22.818 | 0.017909 |
| 9830 | TRIM14 | −22.815 | 0.017921 |
| 55611 | OTUB1 | −22.807 | 0.017935 |
| 60496 | AASDHPPT | −22.806 | 0.017935 |
| 1608 | DGKG | −22.797 | 0.017951 |
| 10681 | GNB5 | −22.797 | 0.017951 |
| 382 | ARF6 | −22.794 | 0.017957 |
| 64689 | GORASP1 | −22.787 | 0.017982 |
| 5585 | PKN1 | −22.782 | 0.017995 |
| 1639 | DCTN1 | −22.776 | 0.018002 |
| 5162 | PDHB | −22.775 | 0.018002 |
| 4691 | NCL | −22.771 | 0.018023 |
| 1718 | DHCR24 | −22.764 | 0.018043 |
| 7743 | ZNF189 | −22.735 | 0.018195 |
| 7994 | KAT6A | −22.727 | 0.018207 |
| 57178 | ZMIZ1 | −22.719 | 0.018237 |
| 1436 | CSF1R | −22.711 | 0.018254 |
| 23469 | PHF3 | −22.71 | 0.018254 |
| 4856 | NOV | −22.709 | 0.018254 |
| 5771 | PTPN2 | −22.709 | 0.018254 |
| 9761 | MLEC | −22.703 | 0.01829 |
| 9744 | ACAP1 | −22.697 | 0.018316 |
| 157 | ADRBK2 | −22.695 | 0.018316 |
| 902 | CCNH | −22.694 | 0.018316 |
| 3958 | LGALS3 | −22.687 | 0.018349 |
| 84861 | KLHL22 | −22.679 | 0.018372 |
| 8986 | RPS6KA4 | −22.674 | 0.018375 |
| 23524 | SRRM2 | −22.673 | 0.018375 |
| 10618 | TGOLN2 | −22.672 | 0.018375 |
| 3587 | IL10RA | −22.667 | 0.018387 |
| 55149 | MTPAP | −22.666 | 0.018387 |
| 7709 | ZBTB17 | −22.665 | 0.018387 |
| 5686 | PSMA5 | −22.66 | 0.018396 |
| 5880 | RAC2 | −22.66 | 0.018396 |
| 23020 | SNRNP200 | −22.645 | 0.018481 |
| 55486 | PARL | −22.632 | 0.018549 |
| 91289 | LMF2 | −22.631 | 0.018549 |
| 10155 | TRIM28 | −22.626 | 0.018579 |
| 6776 | STAT5A | −22.618 | 0.018597 |
| 4077 | NBR1 | −22.615 | 0.018597 |
| 7805 | LAPTM5 | −22.615 | 0.018597 |
| 55317 | AP5S1 | −22.61 | 0.018607 |
| 405 | ARNT | −22.61 | 0.018607 |
| 5518 | PPP2R1A | −22.6 | 0.018653 |
| 4152 | MBD1 | −22.596 | 0.018658 |
| 10970 | CKAP4 | −22.594 | 0.018662 |
| 5000 | ORC4 | −22.588 | 0.018668 |
| 4635 | MYL4 | −22.588 | 0.018668 |
| 4925 | NUCB2 | −22.583 | 0.018687 |
| 5830 | PEX5 | −22.581 | 0.01869 |
| 1861 | TOR1A | −22.579 | 0.018692 |
| 1155 | TBCB | −22.565 | 0.01876 |
| 4087 | SMAD2 | −22.562 | 0.018765 |
| 10982 | MAPRE2 | −22.553 | 0.018819 |
| 84364 | ARFGAP2 | −22.547 | 0.018847 |
| 2769 | GNA15 | −22.544 | 0.018847 |
| 923 | CD6 | −22.543 | 0.018847 |
| 55795 | PCID2 | −22.542 | 0.018847 |
| 8553 | BHLHE40 | −22.535 | 0.018877 |
| 9924 | PAN2 | −22.524 | 0.018942 |
| 820 | CAMP | −22.514 | 0.019007 |
| 10906 | TRAFD1 | −22.484 | 0.019161 |
| 9673 | SLC25A44 | −22.471 | 0.019232 |
| 23225 | NUP210 | −22.461 | 0.019289 |
| 6230 | RPS25 | −22.455 | 0.019308 |
| 552 | AVPR1A | −22.452 | 0.019308 |
| 9975 | NR1D2 | −22.452 | 0.019308 |
| 23530 | NNT | −22.446 | 0.019312 |
| 51340 | CRNKL1 | −22.445 | 0.019312 |
| 1643 | DDB2 | −22.445 | 0.019312 |
| 51559 | NT5DC3 | −22.441 | 0.019327 |
| 9921 | RNF10 | −22.436 | 0.019337 |

TABLE 3-continued

Complete list of differentially expressed genes.

| Entrez ID | Gene symbol (Name) | Combined Tstat | Combined Pval |
|---|---|---|---|
| 51070 | NOSIP | −22.435 | 0.019337 |
| 51393 | TRPV2 | −22.434 | 0.019337 |
| 196441 | ZFC3H1 | −22.408 | 0.019475 |
| 7355 | SLC35A2 | −22.404 | 0.019486 |
| 805 | CALM2 | −22.403 | 0.019486 |
| 25988 | HINFP | −22.397 | 0.019503 |
| 4939 | OAS2 | −22.396 | 0.019503 |
| 54433 | GAR1 | −22.393 | 0.019503 |
| 1783 | DYNC1LI2 | −22.393 | 0.019503 |
| 9812 | KIAA0141 | −22.393 | 0.019503 |
| 79618 | HMBOX1 | −22.391 | 0.019506 |
| 64429 | ZDHHC6 | −22.385 | 0.019523 |
| 64127 | NOD2 | −22.382 | 0.019539 |
| 55332 | DRAM1 | −22.377 | 0.019548 |
| 8031 | NCOA4 | −22.375 | 0.019549 |
| 54850 | FBXL12 | −22.374 | 0.019551 |
| 55213 | RCBTB1 | −22.369 | 0.019571 |
| 23352 | UBR4 | −22.366 | 0.019582 |
| 4701 | NDUFA7 | −22.36 | 0.019613 |
| 55251 | PCMTD2 | −22.347 | 0.019693 |
| 5452 | POU2F2 | −22.346 | 0.019693 |
| 55723 | ASF1B | −22.344 | 0.0197 |
| 8869 | ST3GAL5 | −22.341 | 0.019706 |
| 6388 | SDF2 | −22.332 | 0.01975 |
| 2887 | GRB10 | −22.326 | 0.019787 |
| 3727 | JUND | −22.318 | 0.019825 |
| 64386 | MMP25 | −22.317 | 0.019825 |
| 2535 | FZD2 | −22.312 | 0.01985 |
| 10961 | ERP29 | −22.308 | 0.019871 |
| 8793 | TNFRSF10D | −22.295 | 0.019945 |
| 10444 | ZER1 | −22.293 | 0.019945 |
| 8140 | SLC7A5 | −22.275 | 0.020053 |
| 54509 | RHOF | −22.273 | 0.020053 |
| 6597 | SMARCA4 | −22.266 | 0.020079 |
| 3660 | IRF2 | −22.257 | 0.020139 |
| 4717 | NDUFC1 | −22.25 | 0.020177 |
| 32 | ACACB | −22.243 | 0.020208 |
| 2313 | FLI1 | −22.242 | 0.020208 |
| 23197 | FAF2 | −22.241 | 0.020208 |
| 8125 | ANP32A | −22.238 | 0.020209 |
| 7321 | UBE2D1 | −22.235 | 0.020209 |
| 11235 | PDCD10 | −22.234 | 0.020209 |
| 64784 | CRTC3 | −22.219 | 0.020261 |
| 51604 | PIGT | −22.213 | 0.020261 |
| 8527 | DGKD | −22.213 | 0.020261 |
| 3695 | ITGB7 | −22.212 | 0.020261 |
| 4026 | LPP | −22.212 | 0.020261 |
| 10181 | RBM5 | −22.212 | 0.020261 |
| 4242 | MFNG | −22.207 | 0.020287 |
| 51466 | EVL | −22.205 | 0.020287 |
| 23195 | MDN1 | −22.2 | 0.02031 |
| 5965 | RECQL | −22.199 | 0.02031 |
| 22878 | TRAPPC8 | −22.194 | 0.020335 |
| 11070 | TMEM115 | −22.167 | 0.020499 |
| 10109 | ARPC2 | −22.155 | 0.020574 |
| 1520 | CTSS | −22.151 | 0.020574 |
| 8565 | YARS | −22.148 | 0.020574 |
| 8242 | KDM5C | −22.144 | 0.020574 |
| 1870 | E2F2 | −22.143 | 0.020574 |
| 8906 | AP1G2 | −22.142 | 0.020574 |
| 79890 | RIN3 | −22.142 | 0.020574 |
| 1947 | EFNB1 | −22.141 | 0.020574 |
| 6311 | ATXN2 | −22.135 | 0.020589 |
| 9444 | QKI | −22.135 | 0.020589 |
| 55683 | KANSL3 | −22.133 | 0.020591 |
| 57097 | PARP11 | −22.127 | 0.020627 |
| 25865 | PRKD2 | −22.124 | 0.020638 |
| 3687 | ITGAX | −22.122 | 0.020639 |
| 317 | APAF1 | −22.111 | 0.020709 |
| 55 | ACPP | −22.097 | 0.020785 |
| 5265 | SERPINA1 | −22.096 | 0.020785 |
| 55619 | DOCK10 | −22.09 | 0.020819 |
| 6786 | STIM1 | −22.087 | 0.020828 |
| 3551 | IKBKB | −22.083 | 0.020848 |
| 4836 | NMT1 | −22.068 | 0.02095 |
| 4089 | SMAD4 | −22.046 | 0.021114 |
| 1380 | CR2 | −22.044 | 0.021115 |
| 54877 | ZCCHC2 | −22.035 | 0.021165 |
| 6303 | SAT1 | −22.033 | 0.021165 |
| 29 | ABR | −22.032 | 0.021165 |
| 23095 | KIF1B | −22.026 | 0.021191 |
| 54918 | CMTM6 | −22.014 | 0.021272 |
| 55038 | CDCA4 | −22.009 | 0.021295 |
| 7786 | MAP3K12 | −22.008 | 0.021295 |
| 57147 | SCYL3 | −22.005 | 0.021298 |
| 6643 | SNX2 | −22.005 | 0.021298 |
| 23212 | RRS1 | −21.993 | 0.021375 |
| 51079 | NDUFA13 | −21.988 | 0.021405 |
| 23126 | POGZ | −21.986 | 0.021408 |
| 790 | CAD | −21.985 | 0.021408 |
| 11273 | ATXN2L | −21.982 | 0.021414 |
| 55707 | NECAP2 | −21.973 | 0.021454 |
| 2961 | GTF2E2 | −21.955 | 0.021571 |
| 79903 | NAA60 | −21.954 | 0.021571 |
| 3903 | LAIR1 | −21.939 | 0.021672 |
| 64844 | MARCH7 | −21.938 | 0.021672 |
| 169611 | OLFML2A | −21.935 | 0.021685 |
| 5110 | PCMT1 | −21.93 | 0.021717 |
| 1836 | SLC26A2 | −21.922 | 0.021756 |
| 4300 | MLLT3 | −21.919 | 0.02177 |
| 1147 | CHUK | −21.911 | 0.021807 |
| 5501 | PPP1CC | −21.91 | 0.021807 |
| 65083 | NOL6 | −21.91 | 0.021807 |
| 27175 | TUBG2 | −21.907 | 0.021809 |
| 10607 | TBL3 | −21.904 | 0.021816 |
| 5829 | PXN | −21.894 | 0.021886 |
| 29914 | UBIAD1 | −21.889 | 0.021909 |
| 79717 | PPCS | −21.88 | 0.021945 |
| 9904 | RBM19 | −21.879 | 0.021945 |
| 5702 | PSMC3 | −21.879 | 0.021945 |
| 688 | KLF5 | −21.874 | 0.021962 |
| 55841 | WWC3 | −21.865 | 0.021997 |
| 53347 | UBASH3A | −21.853 | 0.022079 |
| 80146 | UXS1 | −21.85 | 0.022079 |
| 2537 | IFI6 | −21.849 | 0.022079 |
| 3632 | INPP5A | −21.849 | 0.022079 |
| 1737 | DLAT | −21.848 | 0.022079 |
| 6280 | S100A9 | −21.846 | 0.022079 |
| 26036 | ZNF451 | −21.836 | 0.022155 |
| 55833 | UBAP2 | −21.829 | 0.022199 |
| 9725 | TMEM63A | −21.822 | 0.022234 |
| 6742 | SSBP1 | −21.819 | 0.022239 |
| 9453 | GGPS1 | −21.814 | 0.02227 |
| 2188 | FANCF | −21.809 | 0.022294 |
| 27314 | RAB30 | −21.808 | 0.022294 |
| 55303 | GIMAP4 | −21.801 | 0.022327 |
| 1524 | CX3CR1 | −21.8 | 0.022327 |
| 968 | CD68 | −21.783 | 0.022457 |
| 2873 | GPS1 | −21.773 | 0.022514 |
| 8454 | CUL1 | −21.771 | 0.022523 |
| 55690 | PACS1 | −21.764 | 0.022553 |
| 64760 | FAM160B2 | −21.756 | 0.022613 |
| 80742 | PRR3 | −21.751 | 0.022629 |
| 5577 | PRKAR2B | −21.749 | 0.022633 |
| 7189 | TRAF6 | −21.744 | 0.022644 |
| 81618 | ITM2C | −21.734 | 0.022722 |
| 9410 | SNRNP40 | −21.727 | 0.022763 |
| 10352 | WARS2 | −21.725 | 0.022763 |
| 23365 | ARHGEF12 | −21.718 | 0.022797 |
| 5514 | PPP1R10 | −21.714 | 0.022797 |
| 11160 | ERLIN2 | −21.711 | 0.022797 |
| 23761 | PISD | −21.711 | 0.022797 |
| 64581 | CLEC7A | −21.71 | 0.022797 |
| 9031 | BAZ1B | −21.71 | 0.022797 |
| 6812 | STXBP1 | −21.709 | 0.022797 |
| 26994 | RNF11 | −21.706 | 0.022802 |
| 476 | ATP1A1 | −21.705 | 0.022802 |
| 28977 | MRPL42 | −21.699 | 0.022833 |
| 60559 | SPCS3 | −21.697 | 0.022835 |
| 306 | ANXA3 | −21.69 | 0.022881 |

TABLE 3-continued

Complete list of differentially expressed genes.

| Entrez ID | Gene symbol (Name) | Combined Tstat | Combined Pval |
|---|---|---|---|
| 6563 | SLC14A1 | −21.681 | 0.022942 |
| 3735 | KARS | −21.676 | 0.022948 |
| 10261 | IGSF6 | −21.675 | 0.022948 |
| 310 | ANXA7 | −21.674 | 0.022948 |
| 22828 | SCAF8 | −21.672 | 0.022948 |
| 56940 | DUSP22 | −21.672 | 0.022948 |
| 51191 | HERC5 | −21.664 | 0.023006 |
| 1192 | CLIC1 | −21.655 | 0.023069 |
| 23533 | PIK3R5 | −21.652 | 0.023081 |
| 6598 | SMARCB1 | −21.648 | 0.023095 |
| 9219 | MTA2 | −21.647 | 0.023095 |
| 50650 | ARHGEF3 | −21.644 | 0.023114 |
| 5428 | POLG | −21.63 | 0.023211 |
| 9997 | SCO2 | −21.628 | 0.023215 |
| 92579 | G6PC3 | −21.62 | 0.023269 |
| 23240 | KIAA0922 | −21.613 | 0.023315 |
| 9962 | SLC23A2 | −21.612 | 0.023315 |
| 28960 | DCPS | −21.607 | 0.023345 |
| 57515 | SERINC1 | −21.598 | 0.023402 |
| 5510 | PPP1R7 | −21.588 | 0.023464 |
| 2934 | GSN | −21.588 | 0.023464 |
| 9764 | KIAA0513 | −21.569 | 0.02359 |
| 10533 | ATG7 | −21.563 | 0.02359 |
| 50853 | VILL | −21.563 | 0.02359 |
| 63875 | MRPL17 | −21.562 | 0.02359 |
| 7064 | THOP1 | −21.558 | 0.02359 |
| 22907 | DHX30 | −21.557 | 0.02359 |
| 23659 | PLA2G15 | −21.556 | 0.02359 |
| 27109 | ATP5S | −21.552 | 0.023604 |
| 25849 | PARM1 | −21.548 | 0.023615 |
| 83442 | SH3BGRL3 | −21.545 | 0.023622 |
| 29099 | COMMD9 | −21.544 | 0.023622 |
| 11334 | TUSC2 | −21.543 | 0.023622 |
| 7056 | THBD | −21.542 | 0.023622 |
| 23082 | PPRC1 | −21.539 | 0.023632 |
| 9592 | IER2 | −21.527 | 0.023725 |
| 84669 | USP32 | −21.521 | 0.023748 |
| 2185 | PTK2B | −21.517 | 0.023748 |
| 10423 | CDIPT | −21.516 | 0.023748 |
| 10943 | MSL3 | −21.516 | 0.023748 |
| 7073 | TIAL1 | −21.51 | 0.023786 |
| 1487 | CTBP1 | −21.509 | 0.02379 |
| 4817 | NIT1 | −21.503 | 0.023814 |
| 9097 | USP14 | −21.503 | 0.023814 |
| 373 | TRIM23 | −21.501 | 0.023814 |
| 3376 | IARS | −21.481 | 0.023947 |
| 695 | BTK | −21.475 | 0.023985 |
| 939 | CD27 | −21.472 | 0.023999 |
| 9985 | REC8 | −21.47 | 0.024003 |
| 622 | BDH1 | −21.468 | 0.024013 |
| 3710 | ITPR3 | −21.461 | 0.024062 |
| 7750 | ZMYM2 | −21.459 | 0.024069 |
| 51203 | NUSAP1 | −21.45 | 0.024136 |
| 23625 | FAM89B | −21.446 | 0.024153 |
| 2950 | GSTP1 | −21.445 | 0.024153 |
| 1497 | CTNS | −21.441 | 0.024171 |
| 23753 | SDF2L1 | −21.436 | 0.024197 |
| 27042 | DIEXF | −21.425 | 0.024282 |
| 23265 | EXOC7 | −21.424 | 0.024282 |
| 81558 | FAM117A | −21.42 | 0.024304 |
| 37 | ACADVL | −21.412 | 0.024346 |
| 8402 | SLC25A11 | −21.411 | 0.024346 |
| 10616 | RBCK1 | −21.411 | 0.024346 |
| 54676 | GTPBP2 | −21.396 | 0.024467 |
| 27284 | SULT1B1 | −21.393 | 0.024467 |
| 91746 | YTHDC1 | −21.378 | 0.024579 |
| 6948 | TCN2 | −21.372 | 0.02462 |
| 6556 | SLC11A1 | −21.37 | 0.02463 |
| 8518 | IKBKAP | −21.368 | 0.024631 |
| 8574 | AKR7A2 | −21.364 | 0.024661 |
| 7458 | EIF4H | −21.356 | 0.024713 |
| 1593 | CYP27A1 | −21.355 | 0.024713 |
| 10775 | POP4 | −21.347 | 0.024781 |
| 8835 | SOCS2 | −21.343 | 0.024801 |
| 5226 | PGD | −21.336 | 0.024822 |
| 79991 | OBFC1 | −21.335 | 0.024822 |
| 22913 | RALY | −21.332 | 0.024834 |
| 27099 | SND1-IT1 | −21.33 | 0.02484 |
| 6430 | SRSF5 | −21.328 | 0.024846 |
| 10428 | CFDP1 | −21.312 | 0.024953 |
| 55624 | POMGNT1 | −21.311 | 0.024953 |
| 7867 | MAPKAPK3 | −21.311 | 0.024953 |
| 51744 | CD244 | −21.306 | 0.024989 |
| 84065 | TMEM222 | −21.296 | 0.025059 |
| 940 | CD28 | −21.295 | 0.025059 |
| 334 | APLP2 | −21.274 | 0.025245 |
| 54973 | CPSF3L | −21.264 | 0.025308 |
| 5591 | PRKDC | −21.263 | 0.025308 |
| 2026 | ENO2 | −21.252 | 0.025382 |
| 64218 | SEMA4A | −21.251 | 0.025382 |
| 57472 | CNOT6 | −21.249 | 0.025387 |
| 23179 | RGL1 | −21.247 | 0.025395 |
| 1188 | CLCNKB | −21.245 | 0.025395 |
| 6449 | SGTA | −21.243 | 0.025395 |
| 57862 | ZNF410 | −21.243 | 0.025395 |
| 80219 | COQ10B | −21.24 | 0.025407 |
| 57020 | C16orf62 | −21.234 | 0.025451 |
| 22898 | DENND3 | −21.229 | 0.02548 |
| 54583 | EGLN1 | −21.228 | 0.02548 |
| 8216 | LZTR1 | −21.227 | 0.02548 |
| 2356 | FPGS | −21.226 | 0.02548 |
| 51107 | APH1A | −21.207 | 0.025617 |
| 54704 | PDP1 | −21.207 | 0.025617 |
| 347902 | AMIGO2 | −21.202 | 0.02565 |
| 79184 | BRCC3 | −21.2 | 0.025659 |
| 10951 | CBX1 | −21.192 | 0.025716 |
| 801 | CALM1 | −21.191 | 0.025716 |
| 5825 | ABCD3 | −21.186 | 0.025755 |
| 57148 | RALGAPB | −21.18 | 0.025795 |
| 948 | CD36 | −21.173 | 0.025827 |
| 6472 | SHMT2 | −21.158 | 0.025958 |
| 3995 | FADS3 | −21.146 | 0.026018 |
| 3732 | CD82 | −21.142 | 0.026039 |
| 7203 | CCT3 | −21.134 | 0.026089 |
| 1991 | ELANE | −21.133 | 0.026089 |
| 9887 | SMG7 | −21.129 | 0.026117 |
| 51397 | COMMD10 | −21.111 | 0.026277 |
| 215 | ABCD1 | −21.107 | 0.026306 |
| 23339 | VPS39 | −21.098 | 0.026363 |
| 7390 | UROS | −21.098 | 0.026363 |
| 3978 | LIG1 | −21.094 | 0.02639 |
| 5333 | PLCD1 | −21.09 | 0.02642 |
| 9459 | ARHGEF6 | −21.086 | 0.026441 |
| 27229 | TUBGCP4 | −21.084 | 0.026449 |
| 1827 | RCAN1 | −21.081 | 0.026461 |
| 684 | BST2 | −21.076 | 0.026483 |
| 8508 | NIPSNAP1 | −21.076 | 0.026483 |
| 328 | APEX1 | −21.075 | 0.026486 |
| 79652 | TMEM204 | −21.066 | 0.026542 |
| 1051 | CEBPB | −21.065 | 0.026542 |
| 8556 | CDC14A | −21.055 | 0.026602 |
| 8848 | TSC22D1 | −21.055 | 0.026602 |
| 23028 | KDM1A | −21.053 | 0.026602 |
| 4542 | MYO1F | −21.049 | 0.026627 |
| 6386 | SDCBP | −21.042 | 0.026663 |
| 5790 | PTPRCAP | −21.035 | 0.026698 |
| 7702 | ZNF143 | −21.034 | 0.026698 |
| 9647 | PPM1F | −21.02 | 0.026797 |
| 25777 | SUN2 | −21.011 | 0.026844 |
| 3708 | ITPR1 | −21.01 | 0.026844 |
| 6793 | STK10 | −20.992 | 0.027 |
| 25 | ABL1 | −20.992 | 0.027 |
| 6850 | SYK | −20.987 | 0.027013 |
| 51131 | PHF11 | −20.973 | 0.027106 |
| 11130 | ZWINT | −20.967 | 0.027144 |
| 50865 | HEBP1 | −20.966 | 0.027144 |
| 4683 | NBN | −20.963 | 0.027162 |
| 5164 | PDK2 | −20.959 | 0.027176 |
| 8505 | PARG | −20.959 | 0.027176 |
| 55278 | QRSL1 | −20.956 | 0.027187 |

TABLE 3-continued

Complete list of differentially expressed genes.

| Entrez ID | Gene symbol (Name) | Combined Tstat | Combined Pval |
|---|---|---|---|
| 5128 | CDK17 | −20.955 | 0.027187 |
| 8673 | VAMP8 | −20.952 | 0.027202 |
| 5111 | PCNA | −20.949 | 0.027202 |
| 55153 | SDAD1 | −20.949 | 0.027202 |
| 11072 | DUSP14 | −20.948 | 0.027202 |
| 10437 | IFI30 | −20.943 | 0.027245 |
| 11322 | TMC6 | −20.94 | 0.027263 |
| 56980 | PRDM10 | −20.938 | 0.027263 |
| 11142 | PKIG | −20.933 | 0.027301 |
| 710 | SERPING1 | −20.927 | 0.027349 |
| 11339 | OIP5 | −20.911 | 0.027482 |
| 2317 | FLNB | −20.91 | 0.027482 |
| 6774 | STAT3 | −20.909 | 0.027482 |
| 51102 | MECR | −20.907 | 0.027482 |
| 84864 | MINA | −20.906 | 0.027486 |
| 2132 | EXT2 | −20.9 | 0.027511 |
| 8682 | PEA15 | −20.892 | 0.027567 |
| 23450 | SF3B3 | −20.888 | 0.027582 |
| 23175 | LPIN1 | −20.865 | 0.02775 |
| 23673 | STX12 | −20.862 | 0.027751 |
| 140609 | NEK7 | −20.861 | 0.027751 |
| 373156 | GSTK1 | −20.86 | 0.027751 |
| 55819 | RNF130 | −20.857 | 0.027768 |
| 140885 | SIRPA | −20.842 | 0.027882 |
| 5519 | PPP2R1B | −20.842 | 0.027882 |
| 5411 | PNN | −20.839 | 0.0279 |
| 23569 | PADI4 | −20.829 | 0.027968 |
| 1386 | ATF2 | −20.82 | 0.028041 |
| 11183 | MAP4K5 | −20.82 | 0.028041 |
| 4074 | M6PR | −20.818 | 0.028041 |
| 1235 | CCR6 | −20.805 | 0.028167 |
| 54855 | FAM46C | −20.796 | 0.028232 |
| 79443 | FYCO1 | −20.795 | 0.028232 |
| 8030 | CCDC6 | −20.789 | 0.028264 |
| 4800 | NFYA | −20.786 | 0.028268 |
| 22881 | ANKRD6 | −20.779 | 0.028311 |
| 5362 | PLXNA2 | −20.774 | 0.028353 |
| 51816 | CECR1 | −20.772 | 0.028355 |
| 10463 | SLC30A9 | −20.769 | 0.028375 |
| 55832 | CAND1 | −20.766 | 0.028387 |
| 3133 | HLA-E | −20.764 | 0.028387 |
| 55697 | VAC14 | −20.762 | 0.028387 |
| 47 | ACLY | −20.758 | 0.028408 |
| 7264 | TSTA3 | −20.757 | 0.028408 |
| 4643 | MYO1E | −20.75 | 0.028467 |
| 998 | CDC42 | −20.744 | 0.028514 |
| 57185 | NIPAL3 | −20.742 | 0.02852 |
| 29890 | RBM15B | −20.741 | 0.02852 |
| 468 | ATF4 | −20.73 | 0.028576 |
| 9917 | FAM20B | −20.729 | 0.028577 |
| 81571 | MIR600HG | −20.727 | 0.028582 |
| 59307 | SIGIRR | −20.722 | 0.02859 |
| 3676 | ITGA4 | −20.719 | 0.02859 |
| 9781 | RNF144A | −20.717 | 0.02859 |
| 249 | ALPL | −20.716 | 0.02859 |
| 55020 | TTC38 | −20.716 | 0.02859 |
| 10238 | DCAF7 | −20.706 | 0.028678 |
| 2665 | GDI2 | −20.704 | 0.02869 |
| 80005 | DOCK5 | −20.702 | 0.028697 |
| 2869 | GRK5 | −20.7 | 0.028701 |
| 10724 | MGEA5 | −20.694 | 0.028749 |
| 9698 | PUM1 | −20.692 | 0.028749 |
| 80342 | TRAF3IP3 | −20.692 | 0.028749 |
| 51144 | HSD17B12 | −20.681 | 0.028812 |
| 10144 | FAM13A | −20.68 | 0.028812 |
| 50615 | IL21R | −20.679 | 0.028812 |
| 30000 | TNPO2 | −20.678 | 0.028812 |
| 7307 | U2AF1 | −20.674 | 0.028827 |
| 4926 | NUMA1 | −20.672 | 0.02883 |
| 10211 | FLOT1 | −20.671 | 0.02883 |
| 3848 | KRT1 | −20.667 | 0.028863 |
| 3840 | KPNA4 | −20.663 | 0.028888 |
| 54901 | CDKAL1 | −20.662 | 0.028891 |
| 10346 | TRIM22 | −20.655 | 0.028954 |
| 6119 | RPA3 | −20.646 | 0.029022 |
| 6499 | SKIV2L | −20.644 | 0.029029 |
| 10272 | FSTL3 | −20.637 | 0.029091 |
| 2650 | GCNT1 | −20.631 | 0.029141 |
| 79624 | C6orf211 | −20.62 | 0.029227 |
| 10147 | SUGP2 | −20.619 | 0.029227 |
| 9477 | MED20 | −20.618 | 0.029227 |
| 54505 | DHX29 | −20.615 | 0.029245 |
| 10384 | BTN3A3 | −20.599 | 0.029391 |
| 3122 | HLA-DRA | −20.599 | 0.029391 |
| 3419 | IDH3A | −20.595 | 0.029417 |
| 58477 | SRPRB | −20.591 | 0.029445 |
| 3560 | IL2RB | −20.59 | 0.029445 |
| 9110 | MTMR4 | −20.583 | 0.029459 |
| 65123 | INTS3 | −20.583 | 0.029459 |
| 991 | CDC20 | −20.582 | 0.029459 |
| 6722 | SRF | −20.576 | 0.029504 |
| 953 | ENTPD1 | −20.573 | 0.029504 |
| 10605 | PAIP1 | −20.573 | 0.029504 |
| 23312 | DMXL2 | −20.563 | 0.029582 |
| 1173 | AP2M1 | −20.563 | 0.029582 |
| 79879 | CCDC134 | −20.56 | 0.0296 |
| 9867 | PJA2 | −20.545 | 0.029737 |
| 139322 | APOOL | −20.542 | 0.029757 |
| 958 | CD40 | −20.533 | 0.029823 |
| 5828 | PEX2 | −20.531 | 0.029837 |
| 26009 | ZZZ3 | −20.526 | 0.029849 |
| 115207 | KCTD12 | −20.52 | 0.02989 |
| 3561 | IL2RG | −20.517 | 0.029906 |
| 23344 | ESYT1 | −20.515 | 0.029917 |
| 1509 | CTSD | −20.507 | 0.029991 |
| 8395 | PIP5K1B | −20.505 | 0.029991 |
| 27128 | CYTH4 | −20.503 | 0.030001 |
| 55288 | RHOT1 | −20.502 | 0.030004 |
| 5571 | PRKAG1 | −20.5 | 0.030013 |
| 55002 | TMCO3 | −20.494 | 0.030035 |
| 89845 | ABCC10 | −20.491 | 0.030051 |
| 10745 | PHTF1 | −20.49 | 0.030051 |
| 26152 | ZNF337 | −20.487 | 0.030058 |
| 8645 | KCNK5 | −20.485 | 0.030058 |
| 55024 | BANK1 | −20.48 | 0.030089 |
| 1742 | DLG4 | −20.479 | 0.030089 |
| 5230 | PGK1 | −20.466 | 0.030208 |
| 22893 | BAHD1 | −20.466 | 0.030208 |
| 4253 | CTAGE5 | −20.45 | 0.030359 |
| 8897 | MTMR3 | −20.446 | 0.03038 |
| 10589 | DRAP1 | −20.445 | 0.030384 |
| 55662 | HIF1AN | −20.435 | 0.030425 |
| 9913 | SUPT7L | −20.435 | 0.030425 |
| 10801 | SEPT9 | −20.434 | 0.030425 |
| 4708 | NDUFB2 | −20.418 | 0.03059 |
| 104 | ADARB1 | −20.415 | 0.03061 |
| 10629 | TAF6L | −20.405 | 0.030677 |
| 1371 | CPOX | −20.404 | 0.030677 |
| 9770 | RASSF2 | −20.394 | 0.030774 |
| 952 | CD38 | −20.391 | 0.030792 |
| 5033 | P4HA1 | −20.388 | 0.030804 |
| 10964 | IFI44L | −20.388 | 0.030804 |
| 4122 | MAN2A2 | −20.384 | 0.030818 |
| 9730 | VPRBP | −20.384 | 0.030818 |
| 5862 | RAB2A | −20.366 | 0.030952 |
| 10475 | TRIM38 | −20.366 | 0.030952 |
| 432 | ASGR1 | −20.364 | 0.030961 |
| 5983 | RFC3 | −20.361 | 0.030964 |
| 8602 | NOP14 | −20.361 | 0.030964 |
| 11222 | MRPL3 | −20.358 | 0.030978 |
| 25984 | KRT23 | −20.357 | 0.030978 |
| 2124 | EVI2B | −20.355 | 0.030986 |
| 9282 | MED14 | −20.34 | 0.031141 |
| 10921 | RNPS1 | −20.339 | 0.031147 |
| 55603 | FAM46A | −20.336 | 0.031154 |
| 7555 | CNBP | −20.334 | 0.031161 |
| 27339 | PRPF19 | −20.318 | 0.031316 |
| 55726 | ASUN | −20.314 | 0.031323 |
| 51366 | UBR5 | −20.314 | 0.031323 |
| 55324 | ABCF3 | −20.312 | 0.031323 |

TABLE 3-continued

Complete list of differentially expressed genes.

| Entrez ID | Gene symbol (Name) | Combined Tstat | Combined Pval |
|---|---|---|---|
| 8993 | PGLYRP1 | −20.311 | 0.031323 |
| 80308 | FLAD1 | −20.311 | 0.031323 |
| 9819 | TSC22D2 | −20.294 | 0.031503 |
| 55898 | UNC45A | −20.283 | 0.031602 |
| 56172 | ANKH | −20.281 | 0.031617 |
| 64219 | PJA1 | −20.275 | 0.031667 |
| 6429 | SRSF4 | −20.264 | 0.031784 |
| 5719 | PSMD13 | −20.257 | 0.031855 |
| 10288 | LILRB2 | −20.254 | 0.03186 |
| 8418 | CMAHP | −20.244 | 0.031932 |
| 55233 | MOB1A | −20.234 | 0.032017 |
| 2395 | FXN | −20.234 | 0.032017 |
| 57658 | CALCOCO1 | −20.233 | 0.032017 |
| 83480 | PUS3 | −20.23 | 0.032033 |
| 2130 | EWSR1 | −20.225 | 0.032043 |
| 10106 | CTDSP2 | −20.225 | 0.032043 |
| 79815 | NIPAL2 | −20.221 | 0.032058 |
| 6396 | SEC13 | −20.219 | 0.032058 |
| 64418 | TMEM168 | −20.219 | 0.032058 |
| 4680 | CEACAM6 | −20.209 | 0.032148 |
| 6821 | SUOX | −20.204 | 0.032201 |
| 9277 | WDR46 | −20.196 | 0.032276 |
| 84243 | ZDHHC18 | −20.194 | 0.032276 |
| 171023 | ASXL1 | −20.191 | 0.0323 |
| 5879 | RAC1 | −20.187 | 0.03232 |
| 3384 | ICAM2 | −20.186 | 0.03232 |
| 4052 | LTBP1 | −20.179 | 0.032395 |
| 5631 | PRPS1 | −20.173 | 0.032437 |
| 10054 | UBA2 | −20.169 | 0.032466 |
| 2907 | GRINA | −20.162 | 0.032542 |
| 9632 | SEC24C | −20.157 | 0.032585 |
| 8733 | GPAA1 | −20.153 | 0.032611 |
| 6856 | SYPL1 | −20.146 | 0.032654 |
| 2800 | GOLGA1 | −20.134 | 0.032764 |
| 79137 | FAM134A | −20.12 | 0.032913 |
| 23417 | MLYCD | −20.111 | 0.032999 |
| 9734 | HDAC9 | −20.099 | 0.033137 |
| 3705 | ITPK1 | −20.07 | 0.033427 |
| 9354 | UBE4A | −20.07 | 0.033427 |
| 55037 | PTCD3 | −20.066 | 0.033427 |
| 51371 | POMP | −20.065 | 0.033427 |
| 9973 | CCS | −20.058 | 0.033507 |
| 6160 | RPL31 | −20.052 | 0.033555 |
| 2219 | FCN1 | −20.046 | 0.033618 |
| 8473 | OGT | −20.045 | 0.033618 |
| 51776 | ZAK | −20.042 | 0.033634 |
| 8626 | TP63 | −20.039 | 0.033647 |
| 54963 | UCKL1 | −20.039 | 0.033647 |
| 10554 | AGPAT1 | −20.032 | 0.033716 |
| 23230 | VPS13A | −20.027 | 0.03373 |
| 3927 | LASP1 | −20.022 | 0.033778 |
| 64781 | CERK | −20.021 | 0.03378 |
| 1655 | DDX5 | −20.014 | 0.033807 |
| 4353 | MPO | −20.008 | 0.03387 |
| 116138 | KLHDC3 | −20.005 | 0.033884 |
| 3665 | IRF7 | −19.992 | 0.033999 |
| 4627 | MYH9 | −19.992 | 0.033999 |
| 10329 | TMEM5 | −19.991 | 0.033999 |
| 10235 | RASGRP2 | −19.984 | 0.034038 |
| 553115 | PEF1 | −19.973 | 0.034168 |
| 5199 | CFP | −19.972 | 0.034168 |
| 7290 | HIRA | −19.966 | 0.034227 |
| 2648 | KAT2A | −19.963 | 0.03423 |
| 11016 | ATF7 | −19.963 | 0.03423 |
| 7462 | LAT2 | −19.961 | 0.03423 |
| 51164 | DCTN4 | −19.957 | 0.034267 |
| 55558 | PLXNA3 | −19.955 | 0.034275 |
| 4125 | MAN2B1 | −19.948 | 0.034335 |
| 8669 | EIF3J | −19.948 | 0.034335 |
| 63893 | UBE2O | −19.944 | 0.034341 |
| 23169 | SLC35D1 | −19.944 | 0.034341 |
| 8086 | AAAS | −19.943 | 0.034341 |
| 3295 | HSD17B4 | −19.942 | 0.034341 |
| 6403 | SELP | −19.932 | 0.034455 |
| 11252 | PACSIN2 | −19.925 | 0.034518 |
| 7249 | TSC2 | −19.923 | 0.034525 |
| 22880 | MORC2 | −19.921 | 0.03453 |
| 54520 | CCDC93 | −19.919 | 0.034548 |
| 11337 | GABARAP | −19.916 | 0.034557 |
| 9860 | LRIG2 | −19.916 | 0.034557 |
| 55640 | FLVCR2 | −19.912 | 0.034576 |
| 7185 | TRAF1 | −19.902 | 0.034685 |
| 79571 | GCC1 | −19.899 | 0.034701 |
| 64087 | MCCC2 | −19.898 | 0.034701 |
| 5286 | PIK3C2A | −19.885 | 0.034838 |
| 25978 | CHMP2B | −19.88 | 0.034888 |
| 8558 | CDK10 | −19.878 | 0.034902 |
| 547 | KIF1A | −19.868 | 0.035013 |
| 8884 | SLC5A6 | −19.857 | 0.035132 |
| 6749 | SSRP1 | −19.851 | 0.035184 |
| 60492 | CCDC90B | −19.849 | 0.035191 |
| 3984 | LIMK1 | −19.848 | 0.035191 |
| 1964 | EIF1AX | −19.831 | 0.03537 |
| 63899 | NSUN3 | −19.821 | 0.035475 |
| 9710 | KIAA0355 | −19.82 | 0.035477 |
| 51706 | CYB5R1 | −19.813 | 0.035498 |
| 79156 | PLEKHF1 | −19.81 | 0.035498 |
| 60626 | RIC8A | −19.81 | 0.035498 |
| 8642 | DCHS1 | −19.807 | 0.035506 |
| 2815 | GP9 | −19.805 | 0.035516 |
| 9934 | P2RY14 | −19.804 | 0.035516 |
| 5905 | RANGAP1 | −19.8 | 0.035559 |
| 10301 | DLEU1 | −19.793 | 0.035605 |
| 9603 | NFE2L3 | −19.792 | 0.035605 |
| 4582 | MUC1 | −19.788 | 0.035649 |
| 127703 | C1orf216 | −19.783 | 0.035682 |
| 4350 | MPG | −19.778 | 0.035737 |
| 55128 | TRIM68 | −19.773 | 0.035778 |
| 10957 | PNRC1 | −19.772 | 0.035778 |
| 80777 | CYB5B | −19.765 | 0.035838 |
| 1656 | DDX6 | −19.76 | 0.035897 |
| 10365 | KLF2 | −19.758 | 0.035901 |
| 89941 | RHOT2 | −19.755 | 0.035928 |
| 9674 | KIAA0040 | −19.751 | 0.035954 |
| 55852 | TEX2 | −19.747 | 0.035983 |
| 9416 | DDX23 | −19.736 | 0.036112 |
| 26031 | OSBPL3 | −19.729 | 0.036187 |
| 3662 | IRF4 | −19.728 | 0.036187 |
| 79731 | NARS2 | −19.725 | 0.036214 |
| 6932 | TCF7 | −19.718 | 0.036295 |
| 58516 | FAM60A | −19.715 | 0.036309 |
| 22863 | ATG14 | −19.713 | 0.036309 |
| 9057 | SLC7A6 | −19.713 | 0.036309 |
| 10257 | ABCC4 | −19.711 | 0.036314 |
| 5890 | RAD51B | −19.71 | 0.036317 |
| 5660 | PSAP | −19.696 | 0.036437 |
| 9747 | FAM115A | −19.685 | 0.036563 |
| 6573 | SLC19A1 | −19.685 | 0.036563 |
| 8837 | CFLAR | −19.674 | 0.03667 |
| 1677 | DFFB | −19.673 | 0.03667 |
| 114049 | WBSCR22 | −19.672 | 0.036672 |
| 51181 | DCXR | −19.667 | 0.036714 |
| 51427 | ZNF107 | −19.652 | 0.036894 |
| 10233 | LRRC23 | −19.645 | 0.036965 |
| 10084 | PQBP1 | −19.644 | 0.036966 |
| 11188 | NISCH | −19.636 | 0.037004 |
| 54682 | MANSC1 | −19.634 | 0.037004 |
| 29893 | PSMC3IP | −19.634 | 0.037004 |
| 4047 | LSS | −19.629 | 0.03701 |
| 79947 | DHDDS | −19.629 | 0.03701 |
| 4261 | CIITA | −19.628 | 0.03701 |
| 23271 | CAMSAP2 | −19.628 | 0.03701 |
| 10097 | ACTR2 | −19.622 | 0.037061 |
| 51282 | SCAND1 | −19.618 | 0.037095 |
| 9655 | SOCS5 | −19.589 | 0.037376 |
| 23550 | PSD4 | −19.588 | 0.037376 |
| 55187 | VPS13D | −19.582 | 0.037444 |
| 2975 | GTF3C1 | −19.581 | 0.037445 |
| 389 | RHOC | −19.576 | 0.037492 |
| 10632 | ATP5L | −19.572 | 0.037528 |

TABLE 3-continued

Complete list of differentially expressed genes.

| Entrez ID | Gene symbol (Name) | Combined Tstat | Combined Pval |
|---|---|---|---|
| 27315 | PGAP2 | −19.571 | 0.037528 |
| 3959 | LGALS3BP | −19.569 | 0.037546 |
| 8407 | TAGLN2 | −19.556 | 0.037709 |
| 79719 | AAGAB | −19.554 | 0.037709 |
| 79567 | FAM65A | −19.531 | 0.037957 |
| 10973 | ASCC3 | −19.528 | 0.037966 |
| 2054 | STX2 | −19.528 | 0.037966 |
| 6010 | RHO | −19.522 | 0.038033 |
| 6626 | SNRPA | −19.517 | 0.038087 |
| 1743 | DLST | −19.515 | 0.038087 |
| 399 | RHOH | −19.515 | 0.038087 |
| 4650 | MYO9B | −19.51 | 0.038124 |
| 7107 | GPR137B | −19.508 | 0.038132 |
| 1434 | CSE1L | −19.507 | 0.038132 |
| 10020 | GNE | −19.502 | 0.038183 |
| 10285 | SMNDC1 | −19.495 | 0.038238 |
| 960 | CD44 | −19.495 | 0.038238 |
| 1387 | CREBBP | −19.491 | 0.038276 |
| 10540 | DCTN2 | −19.487 | 0.038303 |
| 57466 | SCAF4 | −19.484 | 0.03831 |
| 2799 | GNS | −19.483 | 0.03831 |
| 8079 | MLF2 | −19.483 | 0.03831 |
| 51780 | KDM3B | −19.474 | 0.038387 |
| 3683 | ITGAL | −19.471 | 0.038409 |
| 64777 | RMND5B | −19.464 | 0.03849 |
| 23122 | CLASP2 | −19.462 | 0.038504 |
| 705 | BYSL | −19.461 | 0.038504 |
| 9716 | AQR | −19.456 | 0.038555 |
| 27335 | EIF3K | −19.452 | 0.038598 |
| 81576 | CCDC130 | −19.451 | 0.038598 |
| 26003 | GORASP2 | −19.444 | 0.038674 |
| 55071 | C9orf40 | −19.443 | 0.038682 |
| 4811 | NID1 | −19.438 | 0.038723 |
| 7832 | BTG2 | −19.433 | 0.038779 |
| 8760 | CDS2 | −19.429 | 0.038804 |
| 50813 | COPS7A | −19.42 | 0.038916 |
| 22839 | DLGAP4 | −19.418 | 0.038932 |
| 54849 | DEF8 | −19.416 | 0.03895 |
| 5694 | PSMB6 | −19.413 | 0.038971 |
| 57496 | MKL2 | −19.405 | 0.039053 |
| 9601 | PDIA4 | −19.395 | 0.039139 |
| 1105 | CHD1 | −19.394 | 0.039139 |
| 26993 | AKAP8L | −19.389 | 0.0392 |
| 56478 | EIF4ENIF1 | −19.382 | 0.039243 |
| 57154 | SMURF1 | −19.382 | 0.039243 |
| 5434 | POLR2E | −19.381 | 0.039243 |
| 6416 | MAP2K4 | −19.377 | 0.039278 |
| 3434 | IFIT1 | −19.377 | 0.039278 |
| 6239 | RREB1 | −19.364 | 0.039441 |
| 25875 | LETMD1 | −19.363 | 0.039443 |
| 7277 | TUBA4A | −19.35 | 0.0396 |
| 10559 | SLC35A1 | −19.345 | 0.039645 |
| 1310 | COL19A1 | −19.344 | 0.039645 |
| 64428 | NARFL | −19.342 | 0.039663 |
| 79954 | NOL10 | −19.331 | 0.039799 |
| 64411 | ARAP3 | −19.327 | 0.039848 |
| 7408 | VASP | −19.326 | 0.039848 |
| 10158 | PDZK1IP1 | −19.32 | 0.039915 |
| 9759 | HDAC4 | −19.318 | 0.039934 |
| 10311 | DSCR3 | −19.314 | 0.03997 |
| 10294 | DNAJA2 | −19.312 | 0.039979 |
| 6709 | SPTAN1 | −19.292 | 0.040193 |
| 57037 | ANKMY2 | −19.287 | 0.040251 |
| 6483 | ST3GAL2 | −19.284 | 0.040268 |
| 30845 | EHD3 | −19.283 | 0.040268 |
| 1669 | DEFA4 | −19.275 | 0.040377 |
| 80306 | MED28 | −19.268 | 0.040446 |
| 8563 | THOC5 | −19.266 | 0.040459 |
| 59341 | TRPV4 | −19.263 | 0.04048 |
| 51561 | IL23A | −19.262 | 0.04048 |
| 1781 | DYNC1I2 | −19.259 | 0.040509 |
| 10300 | KATNB1 | −19.244 | 0.040692 |
| 9559 | VPS26A | −19.242 | 0.040714 |
| 2623 | GATA1 | −19.236 | 0.04077 |
| 29998 | GLTSCR1 | −19.216 | 0.041015 |
| 5860 | QDPR | −19.214 | 0.041023 |
| 23093 | TTLL5 | −19.208 | 0.041077 |
| 29796 | UQCR10 | −19.207 | 0.041082 |
| 9663 | LPIN2 | −19.2 | 0.041149 |
| 4048 | LTA4H | −19.199 | 0.041158 |
| 10129 | FRY | −19.196 | 0.041173 |
| 8813 | DPM1 | −19.194 | 0.041188 |
| 54948 | MRPL16 | −19.185 | 0.041296 |
| 2079 | ERH | −19.182 | 0.041302 |
| 29960 | FTSJ2 | −19.178 | 0.041351 |
| 55139 | ANKZF1 | −19.174 | 0.041361 |
| 2220 | FCN2 | −19.172 | 0.041367 |
| 54934 | KANSL2 | −19.17 | 0.041381 |
| 5875 | RABGGTA | −19.165 | 0.041434 |
| 79877 | DCAKD | −19.161 | 0.041468 |
| 9948 | WDR1 | −19.154 | 0.04154 |
| 55041 | PLEKHB2 | −19.153 | 0.041541 |
| 1820 | ARID3A | −19.15 | 0.041564 |
| 11212 | PROSC | −19.145 | 0.041609 |
| 55739 | CARKD | −19.137 | 0.041709 |
| 26100 | WIPI2 | −19.135 | 0.041726 |
| 1088 | CEACAM8 | −19.121 | 0.041917 |
| 84722 | PSRC1 | −19.119 | 0.041943 |
| 79840 | NHEJ1 | −19.113 | 0.042004 |
| 79647 | AKIRIN1 | −19.112 | 0.042004 |
| 2040 | STOM | −19.109 | 0.04202 |
| 3635 | INPP5D | −19.108 | 0.04202 |
| 10781 | ZNF266 | −19.106 | 0.04202 |
| 5087 | PBX1 | −19.095 | 0.04214 |
| 5817 | PVR | −19.093 | 0.04214 |
| 5412 | UBL3 | −19.093 | 0.04214 |
| 9274 | BCL7C | −19.084 | 0.042247 |
| 2760 | GM2A | −19.071 | 0.042424 |
| 9923 | ZBTB40 | −19.06 | 0.042559 |
| 489 | ATP2A3 | −19.051 | 0.042678 |
| 57128 | LYRM4 | −19.044 | 0.042748 |
| 2932 | GSK3B | −19.037 | 0.042839 |
| 146691 | TOM1L2 | −19.036 | 0.042841 |
| 55016 | MARCH1 | −19.03 | 0.042881 |
| 51099 | ABHD5 | −19.026 | 0.042918 |
| 23133 | PHF8 | −19.024 | 0.042933 |
| 92140 | MTDH | −19.021 | 0.042955 |
| 29888 | STRN4 | −19.021 | 0.042955 |
| 57175 | CORO1B | −19.014 | 0.043029 |
| 8703 | B4GALT3 | −18.993 | 0.043214 |
| 3631 | INPP4A | −18.993 | 0.043214 |
| 7916 | PRRC2A | −18.992 | 0.043214 |
| 2631 | GBAS | −18.989 | 0.04324 |
| 643 | CXCR5 | −18.982 | 0.043314 |
| 3835 | KIF22 | −18.981 | 0.043314 |
| 706 | TSPO | −18.98 | 0.043314 |
| 23390 | ZDHHC17 | −18.98 | 0.043314 |
| 5900 | RALGDS | −18.979 | 0.043314 |
| 25801 | GCA | −18.978 | 0.043314 |
| 7248 | TSC1 | −18.973 | 0.043383 |
| 521 | ATP5I | −18.967 | 0.043436 |
| 55007 | FAM118A | −18.961 | 0.04349 |
| 55968 | NSFL1C | −18.96 | 0.04349 |
| 64131 | XYLT1 | −18.959 | 0.04349 |
| 10130 | PDIA6 | −18.958 | 0.043498 |
| 7334 | UBE2N | −18.957 | 0.043498 |
| 10797 | MTHFD2 | −18.95 | 0.043581 |
| 58517 | RBM25 | −18.945 | 0.043639 |
| 9695 | EDEM1 | −18.932 | 0.043791 |
| 157567 | ANKRD46 | −18.927 | 0.043852 |
| 10484 | SEC23A | −18.92 | 0.043908 |
| 7037 | TFRC | −18.92 | 0.043908 |
| 18 | ABAT | −18.919 | 0.043908 |
| 9885 | OSBPL2 | −18.919 | 0.043908 |
| 3300 | DNAJB2 | −18.916 | 0.043919 |
| 4179 | CD46 | −18.915 | 0.043919 |
| 51301 | GCNT4 | −18.911 | 0.043937 |
| 54555 | DDX49 | −18.911 | 0.043937 |
| 9235 | IL32 | −18.909 | 0.043937 |
| 158 | ADSL | −18.905 | 0.043967 |

TABLE 3-continued

Complete list of differentially expressed genes.

| Entrez ID | Gene symbol (Name) | Combined Tstat | Combined Pval |
|---|---|---|---|
| 9693 | RAPGEF2 | −18.904 | 0.043967 |
| 50485 | SMARCAL1 | −18.895 | 0.044072 |
| 3557 | IL1RN | −18.882 | 0.044211 |
| 4035 | LRP1 | −18.882 | 0.044211 |
| 9820 | CUL7 | −18.881 | 0.044211 |
| 10227 | MFSD10 | −18.88 | 0.044211 |
| 79009 | DDX50 | −18.879 | 0.044212 |
| 6738 | TROVE2 | −18.878 | 0.044212 |
| 7803 | PTP4A1 | −18.877 | 0.044212 |
| 3479 | IGF1 | −18.876 | 0.044212 |
| 58986 | TMEM8A | −18.875 | 0.044212 |
| 29780 | PARVB | −18.873 | 0.04423 |
| 6768 | ST14 | −18.864 | 0.044362 |
| 6241 | RRM2 | −18.86 | 0.044409 |
| 10916 | MAGED2 | −18.858 | 0.044416 |
| 8870 | IER3 | −18.843 | 0.044627 |
| 51512 | GTSE1 | −18.839 | 0.044641 |
| 475 | ATOX1 | −18.839 | 0.044641 |
| 322 | APBB1 | −18.837 | 0.044653 |
| 7099 | TLR4 | −18.834 | 0.044679 |
| 9056 | SLC7A7 | −18.833 | 0.044679 |
| 1029 | CDKN2A | −18.832 | 0.044679 |
| 51092 | SIDT2 | −18.824 | 0.044791 |
| 11325 | DDX42 | −18.822 | 0.044791 |
| 51005 | AMDHD2 | −18.82 | 0.044791 |
| 116496 | FAM129A | −18.82 | 0.044791 |
| 3099 | HK2 | −18.817 | 0.04482 |
| 55638 | SYBU | −18.813 | 0.044863 |
| 57134 | MAN1C1 | −18.812 | 0.044863 |
| 51307 | FAM53C | −18.811 | 0.044863 |
| 7407 | VARS | −18.809 | 0.044863 |
| 10959 | TMED2 | −18.802 | 0.04494 |
| 8539 | API5 | −18.796 | 0.045015 |
| 23016 | EXOSC7 | −18.795 | 0.045015 |
| 3004 | GZMM | −18.794 | 0.045015 |
| 537 | ATP6AP1 | −18.792 | 0.045031 |
| 79754 | ASB13 | −18.787 | 0.045106 |
| 1182 | CLCN3 | −18.784 | 0.045123 |
| 10611 | PDLIM5 | −18.777 | 0.04522 |
| 10866 | HCP5 | −18.774 | 0.045246 |
| 23424 | TDRD7 | −18.764 | 0.045365 |
| 373863 | DND1 | −18.76 | 0.045422 |
| 54332 | GDAP1 | −18.759 | 0.045422 |
| 55748 | CNDP2 | −18.75 | 0.045541 |
| 23590 | PDSS1 | −18.749 | 0.045552 |
| 7424 | VEGFC | −18.743 | 0.045622 |
| 51669 | TMEM66 | −18.74 | 0.045652 |
| 5711 | PSMD5 | −18.723 | 0.045864 |
| 11282 | MGAT4B | −18.722 | 0.045864 |
| 8078 | USP5 | −18.708 | 0.046063 |
| 1025 | CDK9 | −18.705 | 0.046098 |
| 55718 | POLR3E | −18.701 | 0.046126 |
| 951 | CD37 | −18.692 | 0.04623 |
| 9806 | SPOCK2 | −18.692 | 0.04623 |
| 9249 | DHRS3 | −18.688 | 0.046274 |
| 4863 | NPAT | −18.681 | 0.046368 |
| 5166 | PDK4 | −18.68 | 0.046375 |
| 81619 | TSPAN14 | −18.673 | 0.046475 |
| 7798 | LUZP1 | −18.667 | 0.046541 |
| 80344 | DCAF11 | −18.665 | 0.046557 |
| 79078 | C1orf50 | −18.657 | 0.046659 |
| 1486 | CTBS | −18.656 | 0.046659 |
| 7084 | TK2 | −18.655 | 0.046659 |
| 120 | ADD3 | −18.654 | 0.046659 |
| 4668 | NAGA | −18.652 | 0.046687 |
| 23325 | KIAA1033 | −18.649 | 0.046691 |
| 3052 | HCCS | −18.648 | 0.046691 |
| 57212 | TP73-AS1 | −18.639 | 0.046793 |
| 6631 | SNRPC | −18.632 | 0.046893 |
| 54884 | RETSAT | −18.628 | 0.046923 |
| 90634 | N4BP2L1 | −18.616 | 0.047107 |
| 8698 | S1PR4 | −18.609 | 0.047156 |
| 1508 | CTSB | −18.609 | 0.047156 |
| 57826 | RAP2C | −18.608 | 0.047156 |
| 3988 | LIPA | −18.604 | 0.047213 |
| 9013 | TAF1C | −18.596 | 0.047325 |
| 811 | CALR | −18.594 | 0.047338 |
| 6811 | STX5 | −18.59 | 0.047364 |
| 23786 | BCL2L13 | −18.59 | 0.047364 |
| 1119 | CHKA | −18.59 | 0.047364 |
| 10131 | TRAP1 | −18.588 | 0.047364 |
| 3796 | KIF2A | −18.588 | 0.047364 |
| 27436 | EML4 | −18.584 | 0.047402 |
| 26509 | MYOF | −18.58 | 0.047462 |
| 51063 | CALHM2 | −18.568 | 0.047639 |
| 79845 | RNF122 | −18.567 | 0.047639 |
| 6352 | CCL5 | −18.566 | 0.047646 |
| 5424 | POLD1 | −18.558 | 0.04775 |
| 23564 | DDAH2 | −18.552 | 0.047778 |
| 25814 | ATXN10 | −18.552 | 0.047778 |
| 387 | RHOA | −18.552 | 0.047778 |
| 2783 | GNB2 | −18.55 | 0.04778 |
| 81552 | VOPP1 | −18.548 | 0.047796 |
| 23378 | RRP8 | −18.547 | 0.047796 |
| 55012 | PPP2R3C | −18.545 | 0.047809 |
| 10810 | WASF3 | −18.532 | 0.047987 |
| 1615 | DARS | −18.523 | 0.048102 |
| 9946 | CRYZL1 | −18.52 | 0.048132 |
| 1803 | DPP4 | −18.514 | 0.048219 |
| 9645 | MICAL2 | −18.512 | 0.048219 |
| 57146 | TMEM159 | −18.511 | 0.048221 |
| 10474 | TADA3 | −18.507 | 0.048266 |
| 2534 | FYN | −18.502 | 0.048334 |
| 5709 | PSMD3 | −18.498 | 0.048357 |
| 9258 | MFHAS1 | −18.498 | 0.048357 |
| 5705 | PSMC5 | −18.495 | 0.048382 |
| 3779 | KCNMB1 | −18.493 | 0.048402 |
| 80198 | MUS81 | −18.491 | 0.04841 |
| 54809 | SAMD9 | −18.488 | 0.048432 |
| 3140 | MR1 | −18.475 | 0.048622 |
| 5473 | PPBP | −18.473 | 0.04864 |
| 53615 | MBD3 | −18.467 | 0.048686 |
| 5552 | SRGN | −18.464 | 0.048728 |
| 26060 | APPL1 | −18.458 | 0.048761 |
| 686 | BTD | −18.458 | 0.048761 |
| 53346 | TM6SF1 | −18.458 | 0.048761 |
| 57408 | LRTM1 | −18.454 | 0.04882 |
| 3265 | HRAS | −18.451 | 0.04883 |
| 663 | BNIP2 | −18.444 | 0.048925 |
| 9070 | ASH2L | −18.442 | 0.048944 |
| 57634 | EP400 | −18.44 | 0.048973 |
| 50840 | TAS2R14 | −18.407 | 0.049521 |
| 11275 | KLHL2 | −18.404 | 0.049555 |
| 23369 | PUM2 | −18.4 | 0.049564 |
| 1108 | CHD4 | −18.398 | 0.049564 |
| 3437 | IFIT3 | −18.397 | 0.049564 |
| 7533 | YWHAH | −18.385 | 0.049753 |
| 79971 | WLS | −18.383 | 0.049772 |
| 9746 | CLSTN3 | −18.382 | 0.049772 |
| 23313 | KIAA0930 | −18.381 | 0.049776 |
| 55862 | ECHDC1 | −18.376 | 0.049843 |
| 54665 | RSBN1 | −18.373 | 0.049885 |
| 80778 | ZNF34 | −18.369 | 0.049935 |

Biological and Functional Analysis

In order to identify the overrepresented biological processes dysregulated in blood of PD patients, we performed a gene pathway analysis using NetworkAnalyst. Pathway analysis was performed using the set of up and downregulated genes separately. Upregulated genes in blood of PD were associated with the Kyoto Encyclopedia of Genes (KEGG) pathways (p<0.05) including bacterial invasion of epithelial cells, mitogen-activated protein kinase (MAPK) signaling pathway, fructose and mannose metabolism, T-cell receptor signaling pathway, mammalian target of rapamycin (mTOR) signaling pathway, type 2 diabetes mellitus and colorectal cancer. The most important hub gene in terms of network topology measures, betweeness (BC) and degree of centrality (DC), was HNF4A (BC=2213; DC=84) (FIG. 2A).

Figure 2B:
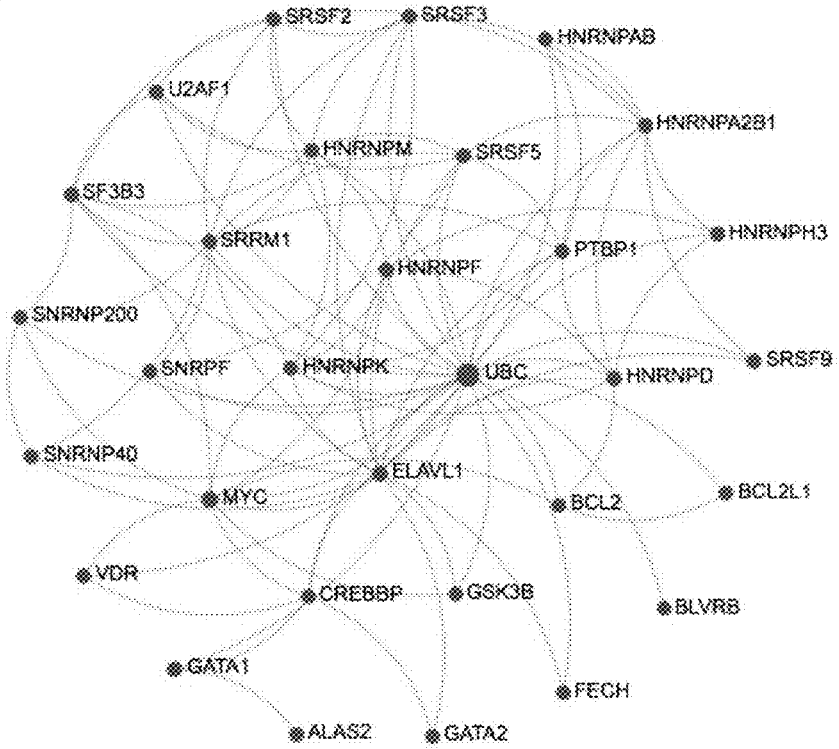

In parallel, downregulated genes in blood of PD patients were associated with the KEGG pathways including protein processing in the endoplasmic reticulum (ER), Epstein-Barr virus infection, and several types of cancer including prostate, endometrial and lung cancer. The most prominent hub gene in terms of network topology measures was ubiquitin C (UBC) (BC=495; DC=1630) and PTBP1 was the most downregulated gene across the four microarray datasets (FIG. 2B, Table 2).

Network-Based Meta-Analysis

Figure 6:
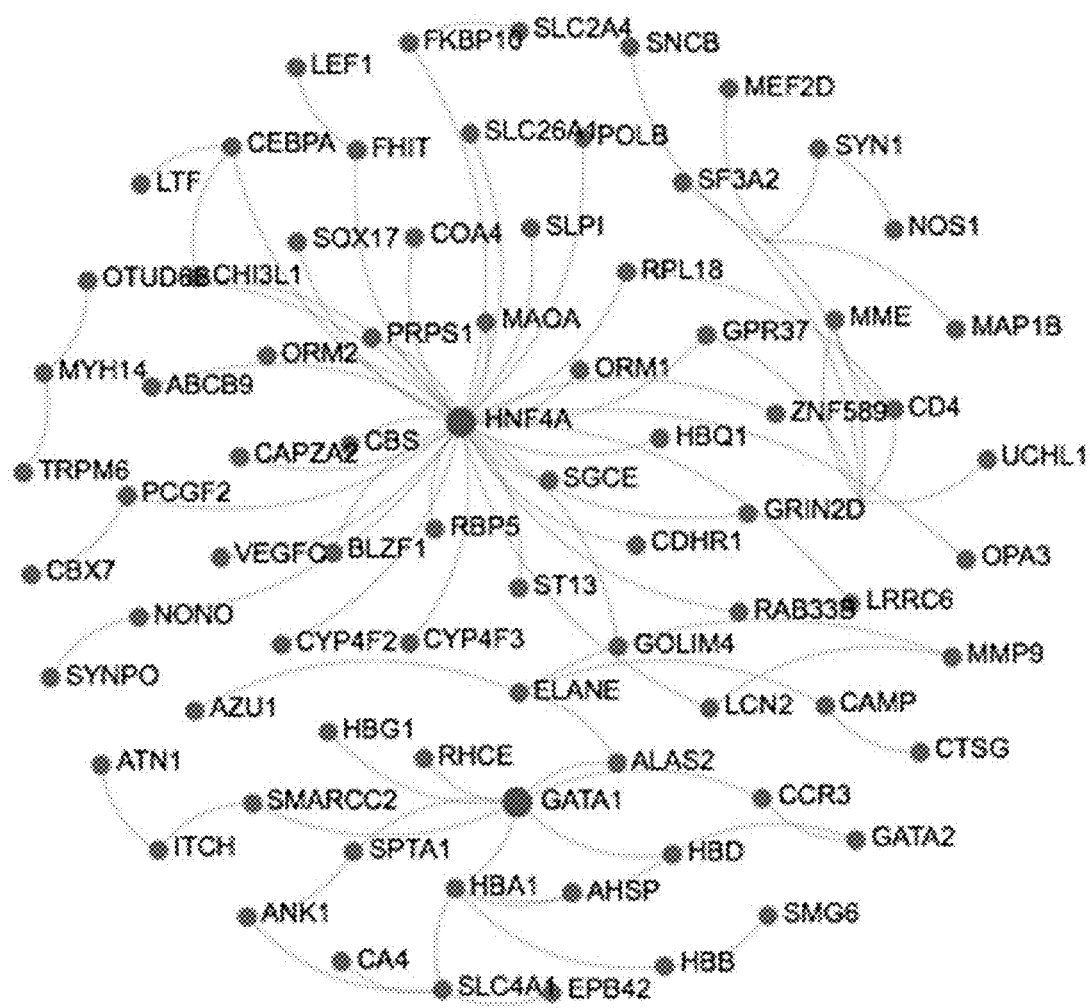
FIG. 6 shows the network-based meta-analysis of microarray studies in blood of PD. Network-based meta-analysis identified HNF4A and GATA1 as the most prominent hub genes across the four microarrays datasets.

HNF4A was confirmed as potential key hub gene in blood of PD by network-based meta-analysis implemented in NetworkAnalyst. The most highly ranked node across the four datasets based on network topology measures was HNF4A (BC=329; DC=35) followed by GATA1 (BC=10.5; DC=8). The resulting zero-order interaction network contained 76 nodes and 81 edges (FIG. 6). In addition, network-based meta-analysis identified the aberrant expression of several splicing factors in PD patients (FIGS. 7A and 7B). Among the splicing factors, PTBP1 was the most significantly downregulated gene in PD patients identified in the meta-analysis (Table 2, FIG. 2B, FIG. 7B).

In order to confirm the dysregulation of HNF4A and PTBP1 at the protein level, a protein microarray study was analyzed in human serum samples of PD (GSE29654) using NetworkAnalyst. PTBP1 was significantly downregulated in PD samples compared to healthy controls (p=0.002). Altered expression of HNF4A was not confirmed in this protein microarray.

Evaluation of HNF4A and PTBP1 mRNAs in Blood of PD

Figure 8A:
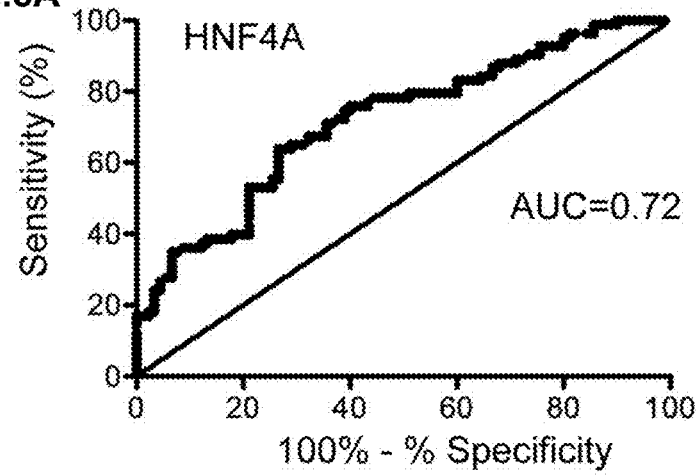
FIGS. 8A, 8B and 8C show the ROC analysis of HNF4A and PTBP1 mRNAs.
Figure 8B:
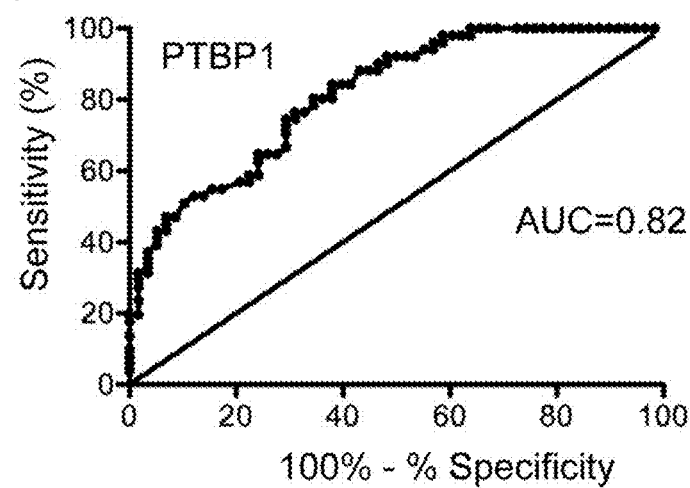
Figure 8C:
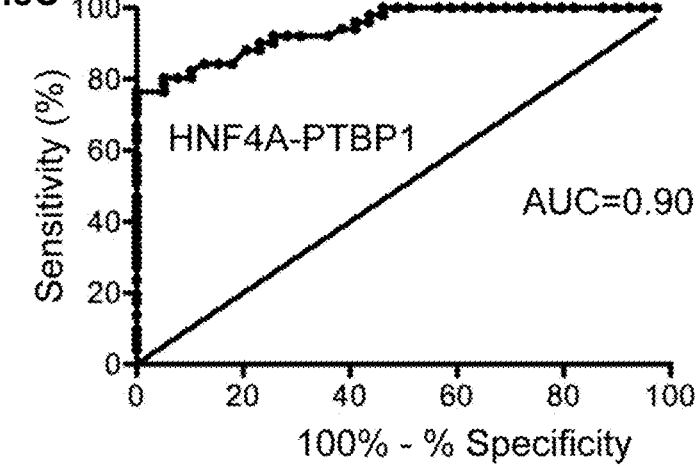

In order to validate the results obtained from the network-based meta-analysis, the most significant hub gene in the upregulated network, HNF4A, and the most downregulated gene, PTBP1, were analyzed as potential biomarkers for PD. Relative abundance of HNF4A and PTBP1 mRNAs was measured in whole blood of PD patients compared to healthy controls (HC) from samples obtained from two independent clinical trials, PROBE and HBS. Quantitative PCR assays revealed that HNF4A and PTBP1 mRNAs were significantly up- and downregulated, respectively, in blood of PD patients compared to HC in both cohorts of study participants at baseline (FIG. 3A-D). Analysis of receiver operating characteristic (ROC) was performed to evaluate the diagnostic accuracy of both biomarkers. ROC analysis for HNF4A and PTBP1 resulted in an area under the curve (AUC) of 0.72 and 0.82, respectively (FIG. 8 A-B). Combination of both biomarkers resulted in an AUC value of 0.90 (FIG. 8C). A step-wise linear discriminant analysis showed that PD patients can be classified with 90% sensitivity and 80% specificity according to the following canonical function: $D_{PD}=0.10+0.56*X_{PTBP1}-0.20X_{HNF4A}$, where $D_{PD}$ is the discriminant score value and X is the mRNA expression level for each biomarker multiplied by its respective canonical coefficient.

Figure 4A:
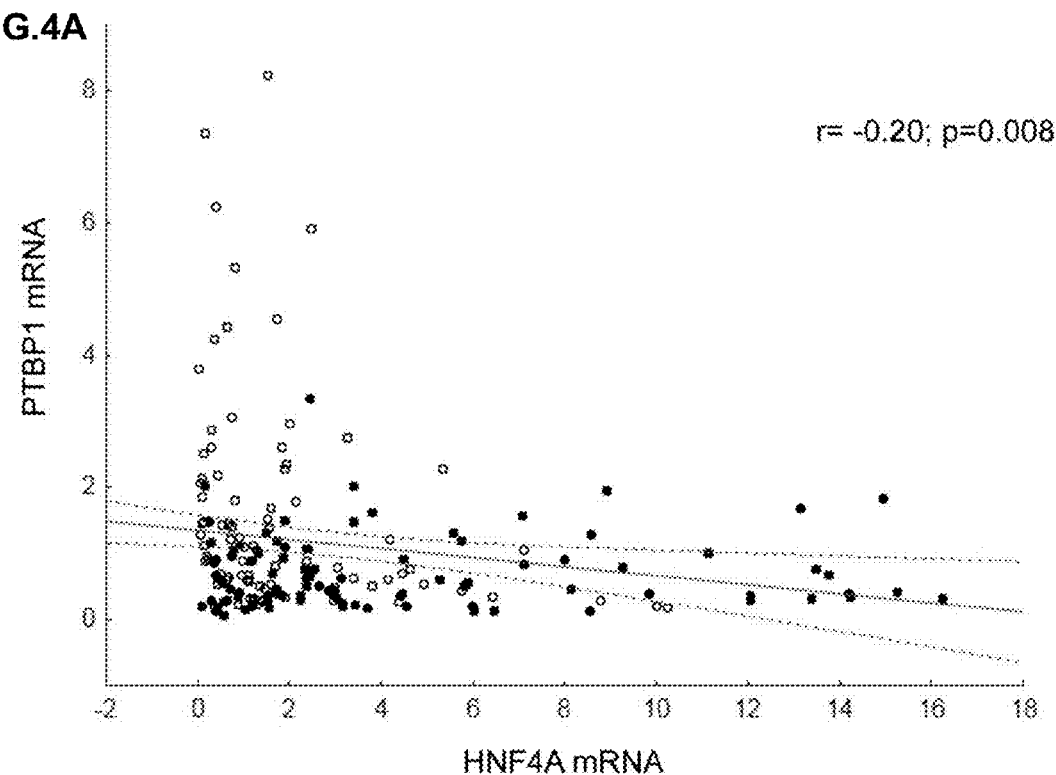
FIGS. 4A and 4B show the biomarker correlation analysis.

Pearson correlation analysis demonstrated that relative abundance of HNF4A and PTBP1 was independent of other covariates including age (HNF4A: r=−0.25, p=0.9; PTBP1: r=0.09, p=0.59) and sex (HNF4A: r=−0.004, p=0.97; PTBP1: r=0.05, p=0.76) in both cohorts of patients and body mass index (BMI) (HNF4A: r=−0.005, p=0.96; PTBP1: r=014, p=0.37) in the HBS cohort. Correlation analysis revealed a significant negative correlation between HNF4A mRNA expression and PTBP1 mRNA (r=−0.20, p=0.008, FIG. 4A) and Hoehn and Yahr stage (HY) at baseline (r=−0.32, p=0.002, FIG. 4B).

Longitudinal Performance of HNF4A and PTBP1

In order to determine the longitudinal performance of HNF4A and PTBP1, the relative abundance of each biomarker in HBS samples collected was measured at two time points. The estimated rate of change for each biomarker was determined via a linear mixed-effects model using the two time points (baseline and 3 years follow-up) collected repeatedly between the same subjects adjusting for age, sex, and BMI. Relative abundance of HNF4A mRNA significantly decreased over time in PD patients compared to HC ($\beta=-0.93$, p=0.002) whereas PTBP1 mRNA increased in PD patients ($\beta=0.33$, p=0.004). Relative abundance of HNF4A and PTBP1 mRNAs was significantly upregulated in PD patients compared to HC in the follow up period (FIGS. 5B and D). Correlation between the relative abundance of each biomarker and HY stage did not reach statistical significance in the longitudinal analysis.

Discussion

Biomarker discovery and validation is a crucial step towards the improvement of clinical management of PD. Specifically, biomarkers that are useful to track the clinical course of PD are essential to the development of effective therapeutics. Network analysis offers an unbiased approach to identify and prioritize biologically meaningful biomarkers for several neurodegenerative diseases. Here, a network-based meta-analysis was performed integrating gene expression profiles of untreated, sporadic and PD patients harboring a LRRK2 (G2019S) mutation in order to identify convergence among the different studies in blood of PD. Transcriptomic meta-analysis identified 2,781 genes consistently differentially expressed in blood of PD across four microarray studies.

Network-based meta-analysis identified HNF4A as the most significant hub gene across the four microarrray datasets, and PTBP1 was identified as the most significant downregulated gene across the four microarrays datasets. HNF4A and PTBP1 mRNAs were further evaluated as blood biomarkers for PD. Relative abundance of HNF4A mRNA was upregulated whereas PTBP1 mRNA was downregulated in blood of PD patients compared to healthy individuals in samples obtained from two independent clinical trials (FIG. 3A-D). Evaluation of biomarker performance showed that HNF4A and PTBP1 can distinguish PD patients from HC with a 90% sensitivity and 80% specificity (FIG. 8C). The diagnostic performance of these two biomarkers is superior than the one afforded by previously identified risk markers in blood of PD and current clinical assessment (Santiago et al., (2013) Specific splice variants are associated with Parkinson's disease. *Mov Disord* 28(12):1724-1727; and Molochnikov et al. (2012) A molecular signature in blood identifies early Parkinson's disease. *Mol Neurodegener* 7:26). The sensitivity of the two markers alone is also greater than the splice variant-specific RNA blood biosignature that included 13 risk markers (Potashkin et al., (2012) Biosignatures for Parkinson's disease and atypical parkinsonian disorders patients. *PLoS One* 7(8):e43595).

Figure 4B:
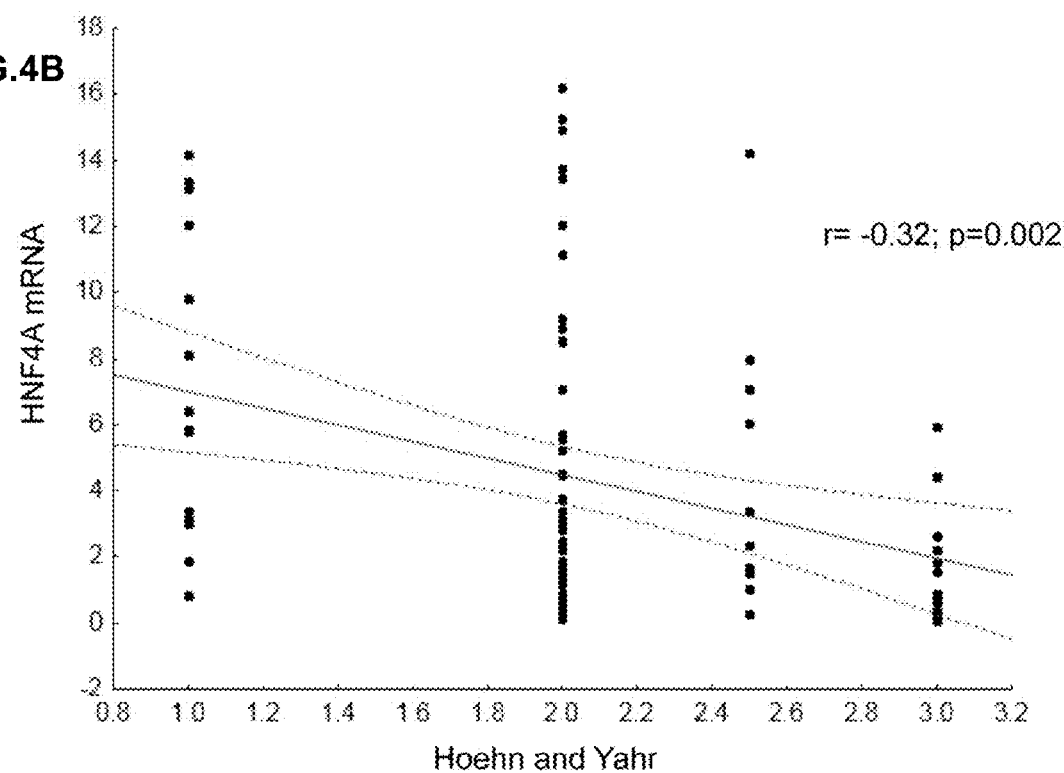

HNF4A mRNA relative abundance significantly correlated with PTBP1 mRNA. A significant negative correlation was found between HNF4A mRNA expression and the HY staging. Early PD patients with a low HY scale rating (HY=1) showed a significantly higher upregulation of HNF4A mRNA compared to patients with a higher HY scale (HY=3) (FIG. 4B). This finding suggests that HNF4A mRNA may be useful to identify patients at very early stages of PD when therapeutic intervention may be most beneficial and to monitor disease severity.

Longitudinal performance analysis showed that relative abundance of each biomarker significantly changed over time in PD patients. For instance, HNF4A mRNA significantly decreased whereas PTBP1 mRNA increased in PD patients during 3 years follow up (FIG. 5). The correlation between the relative abundance of both biomarkers with HY stage did not reach statistical significance in follow-up samples, however. One possible explanation is that the HY stage did not change in most of the PD patients during the 3 years period, whereas the relative abundance of the genes did change during this time period. These results suggest that the abundance of HNF4A and PTBP1 mRNAs in blood may be more sensitive than assessment of motor symptoms for monitoring disease progression. The dynamic change in expression over time of both biomarkers suggests that they may be useful biomarkers to track the clinical course of PD patients.

One potential caveat is that most of the PD patients were medicated in this study, therefore, a potential confounding factor introduced by PD medications cannot be ruled out. Nevertheless, this finding is interesting in light of the evidence that indicates that more than 50% of the PD patients are glucose intolerant and patients with diabetes that develop PD usually have a higher HY staging. Moreover, impaired glucose metabolism is suggested to be an early event in sporadic PD. Given that HNF4A plays a pivotal role in hepatic gluconeogenesis and PTBP1 regulates and stabilize mRNA translation of insulin in the pancreas, the inverse regulation of both genes provide a molecular rationale for the impairment of insulin signaling in PD patients and thus may be potential therapeutic targets.

Analysis of a previous protein microarray study in human serum samples with PD (Han et al., (2012) Diagnosis of Parkinson's disease based on disease-specific autoantibody profiles in human sera. *PLoS One* 7(2):e32383) revealed that PTBP1 was significantly downregulated in PD patients compared to controls (p=0.02), but expression of HNF4A was not identified. Thus, protein levels of PTBP1 may be also a potential diagnostic biomarker for PD.

The network of downregulated genes was centered in the polyubiquitin precursor UBC and associated with protein processing in the ER (FIG. 2B). In this regard, growing evidence indicates that ER dysfunction is an early event in the PD pathogenesis and targeting components of the unfolded protein response may be a potential therapeutic strategy.

The results from this meta-analysis also highlight the dysregulation of several splicing factors in blood of PD patients. As the spliceosome assembles, protein-protein interactions are highly dynamic. One of the essential steps in the assembly of the spliceosome is the formation of new protein interactions that change the inactive B splicing complex to an active complex in which SF3B2, SF3B3 and SF3B5 form new interactions with proteins of the U5 small nuclear ribonucleic particles (snRNP). In this context, several of the core factors of the U2 snRNP were upregulated in PD including SF3A1, SF3A2, SF3B1 and SF3B4, whereas SF3B3 was downregulated (FIG. 2 and FIG. 7). These results suggest that assembly of the U2 snRNP that binds to the 3' splice site may be facilitated in PD, but the efficient formation of an active splicing complex in PD is highly unlikely. The results from the meta-analysis also revealed that many of the regulatory splicing factors, core factors of the U1, U4, U5 and U6 snRNPs, and helicases are downregulated in PD further supporting the idea that splicing may be both inefficient and dysregulated in PD (FIG. 7B). In this regard, aberrant alternative splicing in blood of PD has been highlighted in numerous studies (Potashkin et al., (2012) Biosignatures for Parkinson's disease and atypical parkinsonian disorders patients. *PLoS One* 7(8):e43595; Santiago et al., (2013) Specific splice variants are associated with Parkinson's disease. *Mov Disord* 28(12):1724-1727; Soreq et al., (2012) Exon arrays reveal alternative splicing aberrations in Parkinson's disease leukocytes. *Neurodegener Dis* 10(1-4):203-206; Soreq et al. (2013) Small RNA sequencing-microarray analyses in Parkinson leukocytes reveal deep brain stimulation-induced splicing changes that classify brain region transcriptomes. *Front Mol Neurosci* 6:10; and Soreq et al. (2014) Long non-coding RNA and alternative splicing modulations in Parkinson's leukocytes identified by RNA sequencing. *PLoS Comput Biol* 10(3): e1003517). In addition, heterogeneous nuclear ribonucleoproteins (hnRNPs), cap-binding proteins and proteins of the exon junction complex were downregulated in PD suggesting that other post-transcriptional events such as cap-binding protein complex formation, localization, maturation, nonsense-mediated mRNA decay and translation may be inefficient or dysregulated in PD (FIG. 2 and FIG. 7).

The vitamin D receptor (VDR) was also present in the network of downregulated genes thus confirming previous findings reporting lower levels of VDR in blood and plasma of PD patients. In addition, a subset of highly co-expressed genes associated with heme metabolism previously identified in blood of two independent populations ALAS2, FECH, and BLVRB were also found to be downregulated in the meta-analysis (FIG. 2B). Further, other PD blood biomarkers HSPA8 and SKP1 were identified in the meta-analysis. Collectively, these results confirm the presence of a common molecular signature in human blood of PD patients.

In summary, this study highlights the prominent convergence among blood microarray studies from sporadic, de novo and the most common hereditary cause of PD and confirms the utility of blood as a useful source of biomarkers for PD. In addition, these results strengthen the association between PD and diabetes and provide insights into the molecular mechanisms underlying the impairment of insulin signaling observed in PD patients. Further, this study underscores the potential of network analysis as a powerful framework to gain insight into the mechanisms underlying PD and to identify potential therapeutic targets and biomarkers of disease severity. Evaluation of HNF4A and PTBP1 mRNAs in a larger prospective study including patients at risk will be important to assess its clinical utility as a diagnostic tool for PD.

The invention claimed is:

1. A method for diagnosing, prognosing or monitoring Parkinson's Disease (PD) in a human subject, comprising:
   (a) obtaining a blood sample from a human subject suspected of having PD;
   (b) determining the expression level of HNF4A and PTBP1 in the blood sample from the human subject suspected of having PD; wherein the expression level of HNF4A is determined using a set of primer pairs suitable for the detection and quantification of the nucleic acid expression of HNF4A, and wherein the expression level of PTBP1 is determined using a set of primer pairs suitable for the detection and quantification of the nucleic acid expression of PTBP1; and wherein HNF4A is encoded by SEQ ID NO: 07, and PTBP1 is encoded by SEQ ID NO: 09; wherein the set of primers suitable for the detection and quantification of the nucleic acid expression of HNF4A comprise SEQ ID NO:03 and SEQ ID NO:04, and wherein the set of primers suitable for the detection and quantification of the nucleic acid expression of PTBP1 comprise SEQ ID NO:05 and SEQ ID NO:06; and
   (c) comparing the expression level of HNF4A and PTBP1 in the blood sample to the expression level of HNF4A and PTBP1 in a non-PD, healthy control sample, whereby an increased expression level of HNF4A in the blood sample from the human subject suspected of having PD as compared to the non-PD sample is indicative of PD and a decreased expression level of PTBP1 in the blood sample from the human subject suspected of having PD as compared to the non-PD sample is indicative of PD, thereby diagnosing the human subject as having PD.

2. The method of claim 1, wherein the expression level is determined by detecting messenger RNA.

3. The method of claim 1, further comprising reverse transcription of the messenger RNA prior to detecting.

4. The method of claim 1, wherein determining the expression level of the at least one gene is by measuring a level of fluorescence by a sequence detection system following a quantitative, real-time polymerase chain reaction (PCR) assay.

5. The method of claim 1, further comprising determining a treatment regimen for the human subject.

6. The method of claim 1, wherein:
   (a) a decreased HNF4A expression level of the human subject at a later time point compared to the HNF4A expression level at an initial time point indicates disease progression and no change of HNF4A expression levels of the human subject at a later time point compared to the HNF4A expression level at an initial time point indicates no disease progression of PD in the subject; and
   (b) an increased PTBP1 expression level of the human subject at a later time point compared to the PTBP1 expression level at an initial time point indicates disease progression of PD in the subject and no change of PTBP1 expression levels of the human subject at a later time point compared to the PTBP1 expression level at an initial time point indicates no disease progression.

7. A method of treating a human subject for Parkinson's Disease (PD), the method comprising:
   (a) obtaining a diagnosis identifying a human subject as having PD, wherein the diagnosis was obtained by:
      (i) obtaining a blood sample from a human subject suspected of having PD;
      (ii) determining the expression level of HNF4A and PTBP1; wherein the expression level of HNF4A is determined using a set of primer pairs suitable for the detection and quantification of the nucleic acid expression of HNF4A, and wherein the expression level of PTBP1 is determined using a set of primer pairs suitable for the detection and quantification of the nucleic acid expression of PTBP1; and wherein HNF4A is encoded by SEQ ID NO: 07, and PTBP1 is encoded by SEQ ID NO: 09; wherein the set of primers suitable for the detection and quantification of the nucleic acid expression of HNF4A comprise SEQ ID NO:03 and SEQ ID NO:04, and wherein the set of primers suitable for the detection and quantification of the nucleic acid expression of PTBP1 comprise SEQ ID NO:05 and SEQ ID NO:06, and
      (iii) comparing the expression level of HNF4A and PTBP1 in the blood sample to the expression level of HNF4A and PTBP1 in a non-PD, healthy control sample, whereby the increased expression level of HNF4A in the blood sample from the human subject suspected of having PD as compared to the non-PD sample is indicative of PD, and a decreased expression level of PTBP1 in the blood sample from the human subject suspected of having PD as compared to the non-PD sample is indicative of PD, thereby diagnosing the human subject as having PD; and
   (b) administering to the subject a PD treatment regimen.

8. The method of claim 7, wherein the expression level is determined by detecting messenger RNA of HNFA4A and PTBP1.

9. The method of claim 7, further comprising reverse transcription of the messenger RNA prior to detecting.

10. The method of claim 7, wherein determining the expression level of the at least one gene is by measuring a level of fluorescence by a sequence detection system following a quantitative, real-time polymerase chain reaction (PCR) assay.

11. A Parkinson's Disease (PD) diagnosis, prognosis or monitoring kit, consisting of a set of primer pairs suitable for the detection and quantification of the nucleic acid expression of HNF4A and a set of primer pairs suitable for the detection and quantification of the nucleic acid expression of PTBP1, wherein HNF4A is encoded by SEQ ID NO: 07, and PTBP1 is encoded by SEQ ID NO: 09, and the set of primers suitable for the detection and quantification of the nucleic acid expression of HNF4A comprise SEQ ID NO:03 and SEQ ID NO:04, and wherein the set of primers suitable for the detection and quantification of the nucleic acid expression of PTBP1 comprise SEQ ID NO:05 and SEQ ID NO:06.

12. The kit of claim 11, wherein the kit further comprises one or more of buffers, wash reagents, polymerases, internal controls, or reagents capable of detecting the presence of a bound nucleic acid primer.

* * * * *

SEQUENCE LISTING

<160> NUMBER OF SEQ ID NOS: 10

<210> SEQ ID NO 1
<211> LENGTH: 21
<212> TYPE: DNA

-continued

<213> ORGANISM: Artificial Sequence
<220> FEATURE:
<223> OTHER INFORMATION: Synthetic oligonucleotide

<400> SEQUENCE: 1
caacggattt ggtcgtattg g                                         21

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
tgatggcaac aatatccact ttacc                                     25

<210> SEQ ID NO 3
<211> LENGTH: 21
<212> TYPE: DNA
<213> ORGANISM: Artificial Sequence
<220> FEATURE:
<223> OTHER INFORMATION: Synthetic oliognucleotide

<400> SEQUENCE: 3
cagaatgagc gggaccggat c                                         21

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
cagcagctgc tccttcatgg ac                                        22

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gctcaggatc atcgtggaga a                                         21

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
atcttcaaca ctgtgccgaa ctt                                       23

<210> SEQ ID NO 7
<211> LENGTH: 4737
<212> TYPE: DNA
<213> ORGANISM: Homo sapiens

<400> SEQUENCE: 7
ggtttgaaag gaaggcagag agggcactgg gaggaggcag tgggagggcg gagggcgggg      60
gccttcgggg tgggcgccca ggtagggca ggtggccgcg gcgtggaggc agggagaatg      120

```
cgactctcca aaaccctcgt cgacatggac atggccgact acagtgctgc actggaccca    180
gcctacacca ccctggaatt tgagaatgtg caggtgttga cgatgggcaa tgacacgtcc    240
ccatcagaag gcaccaacct caacgcgccc aacagcctgg gtgtcagcgc cctgtgtgcc    300
atctgcgggg accgggccac gggcaaacac tacggtgcct cgagctgtga cggctgcaag    360
ggcttcttcc ggaggagcgt gcggaagaac cacatgtact cctgcagatt tagccggcag    420
tgcgtggtgg acaaagacaa gaggaaccag tgccgctact gcaggctcaa gaaatgcttc    480
cgggctggca tgaagaagga agccgtccag aatgagcggg accggatcag cactcgaagg    540
tcaagctatg aggacagcag cctgccctcc atcaatgcgc tcctgcaggc ggaggtcctg    600
tcccgacaga tcacctcccc cgtctccggg atcaacggcg acattcgggc gaagaagatt    660
gccagcatcg cagatgtgtg tgagtccatg aaggagcagc tgctggttct cgttgagtgg    720
gccaagtaca tcccagcttt ctgcgagctc cccctggacg accaggtggc cctgctcaga    780
gcccatgctg gcgagcacct gctgctcgga gccaccaaga gatccatggt gttcaaggac    840
gtgctgctcc taggcaatga ctacattgtc cctcggcact gcccggagct ggcggagatg    900
agccgggtgt ccatacgcat cccttgacga gctggtgctgc ccttccagga gctgcagatc    960
gatgacaatg agtatgccta cctcaaagcc atcatcttct ttgacccaga tgccaagggg   1020
ctgagcgatc cagggaagat caagcggctg cgttcccagg tgcaggtgag cttggaggac   1080
tacatcaacg accgccagta tgactcgcgt ggccgctttg agagctgct gctgctgctg    1140
cccaccttgc agagcatcac ctggcagatg atcgagcaga tccagttcat caagctcttc   1200
ggcatggcca agattgacaa cctgttgcag gagatgctgc tgggagggtc ccccagcgat   1260
gcacccatg cccaccaccc cctgcaccct cacctgatgc aggaacatat gggaaccaac    1320
gtcatcgttg ccaacacaat gcccactcac ctcagcaacg gacagatgtg tgagtggccc   1380
cgacccaggg gacaggcagc caccctgag accccacagc cctcaccgcc aggtggctca   1440
gggtctgagc cctataagct cctgccggga gccgtcgcca caatcgtcaa gcccctctct   1500
gccatccccc agccgaccat caccaagcag gaagttatct agcaagccgc tggggcttgg   1560
gggctccact ggctccccc agcccctaa gagagcacct ggtgatcacg tggtcacggc    1620
aaaggaagac gtgatgccag gaccagtccc agagcaggaa tgggaaggat gaagggcccg   1680
agaacatggc ctaagggcca catcccactg ccacccttga cgccctgctc tggataacaa   1740
gactttgact tggggagacc tctactgcct tggacaactt ttctcatgtt gaagccactg   1800
ccttcacctt caccttcatc catgtccaac ccccgacttc atcccaaagg acagccgcct   1860
ggagatgact tgaggcctta cttaaaccca gctcccttct tccctagcct ggtgcttctc   1920
ctctcctagc ccctgtcatg gtgtccgac agagccctgt gaggctgggt ccaattgtgg    1980
cacttgggg accttgctcc tccttctgct gctgcccca cctctgctgc ctccctctgc    2040
tgtcaccttg ctcagccatc ccgtcttctc caacaccacc tctccagagg caaggaggc    2100
cttggaaacg attcccccag tcattctggg aacatgttgt aagcactgac tgggaccagg   2160
caccaggcag gtctagaag gctgtggtga gggaagacgc ctttctcctc caacccaacc    2220
tcatcctcct tcttcaggga cttgggtggg tacttgggtg aggatccctg aaggccttca   2280
acccgagaaa acaaacccag gttggcgact gcaacaggaa cttggagtgg agaggaaaag   2340
catcagaaag aggcagacca tccaccaggc ctttgagaaa gggtagaatt ctggctggta   2400
gagcaggtga gatgggacat tccaaagaac agcctgagcc aaggcctagt ggtagtaaga   2460
```

```
atctagcaag aattgaggaa gaatggtgtg ggagagggat gatgaagaga gagagggcct    2520
gctggagagc atagggtctg gaacaccagg ctgaggtcct gatcagcttc aaggagtatg    2580
cagggagctg ggcttccaga aaatgaacac agcagttctg cagaggacgg gaggctggaa    2640
gctgggaggt caggtggggt ggatgatata atgcgggtga gagtaatgag gcttggggct    2700
ggagaggaca agatgggtaa accctcacat cagagtgaca tccaggagga ataagctccc    2760
agggcctgtc tcaagctctt ccttactccc aggcactgtc ttaaggcatc tgacatgcat    2820
catctcattt aatcctccct tcctccctat taacctagag attgtttttg ttttttattc    2880
tcctcctccc tccccgccct cacccgcccc actccctcct aacctagaga ttgttacaga    2940
agctgaaatt gcgttctaag aggtgaagtg attttttttc tgaaactcac acaactagga    3000
agtggctgag tcaggacttg aacccaggtc tccctggatc agaacaggag ctcttaacta    3060
cagtggctga atagcttctc caaaggctcc ctgtgttctc accgtgatca agttgagggg    3120
cttccggctc ccttctacag cctcagaaac cagactcgtt cttctgggaa ccctgcccac    3180
tcccaggacc aagattggcc tgaggctgca ctaaaattca cttagggtcg agcatcctgt    3240
ttgctgataa atattaagga gaattcatga ctcttgacag cttttctctc ttcactcccc    3300
aagtcaaggg gaggggtggc aggggtctgt ttcctggaag tcaggctcat ctggcctgtt    3360
ggcatggggg tgggacagtg tgcacagtgt gggggcaggg gagggctaag caggcctggg    3420
tttgagggct gctccggaga ccgtcactcc aggtgcattc tggaagcatt agaccccagg    3480
atggagcgac cagcatgtca tccatgtgga atcttggtgg ctttgaggac attctggaaa    3540
atgccactga ccagtgtgaa caaaagggat gtgttatggg gctggaggtg tgattaggta    3600
ggagggaaac tgttggaccg actcctgccc cctgctcaac actgacccct ctgagtggtt    3660
ggaggcagtg ccccagtgcc cagaaatccc accattagtg attgtttttt atgagaaaga    3720
ggcgtggaga agtattgggg caatgtgtca gggaggaatc accacatccc tacggcagtc    3780
ccagccaagc ccccaatccc agcggagact gtgccctgct cagagctccc aagccttccc    3840
ccaccacctc actcaagtgc ccctgaaatc cctgccagac ggctcagcct ggtctgcggt    3900
aaggcaggga ggctggaacc atttctgggc attgtggtca ttcccactgt gttcctccac    3960
ctcctccctc cagcgttgct cagacctctg tcttgggaga aaggttgaga taagaatgtc    4020
ccatggagtg ccgtgggcaa cagtggccct tcatgggaac aatctgttgg agcagggggt    4080
cagttctctg ctgggaatct accccttttct ggaggagaaa cccattccac cttaataact    4140
ttattgtaat gtgagaaaca caaaacaaag tttactttttt tgactctaag ctgacatgat    4200
attagaaaat ctctcgctct cttttttttt tttttttttt ttttggcta cttgagttgt    4260
ggtcctaaaa cataaaatct gatggacaaa cagagggttg ctgggggac aagcgtgggc    4320
acaatttccc caccaagaca ccctgatctt caggcgggtc tcaggagctt ctaaaaatcc    4380
gcatggctct cctgagagtg gacagaggag aggagagggt cagaaatgaa cgctcttcta    4440
tttcttgtca ttaccaagcc aattactttt gccaatttt tctgtgatct gccctgatta    4500
agatgaattg tgaaatttac atcaagcaat tatcaaagcg ggctgggtcc catcagaacg    4560
acccacatct ttctgtgggt gtgaatgtca ttaggtcttg cgctgacccc tgagccccca    4620
tcactgccgc ctgatggggc aaagaaacaa aaacatttc ttactcttct gtgttttaac    4680
aaaagtttat aaaacaaaat aaatggcgca tatgttttct aaaaaaaaaa aaaaaaa      4737
```

<210> SEQ ID NO 8
<211> LENGTH: 474

<212> TYPE: PRT
<213> ORGANISM: Homo sapiens

<400> SEQUENCE: 8

```
Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
                20                  25                  30

Val Leu Thr Met Gly Asn Asp Thr Ser Pro Ser Glu Gly Thr Asn Leu
            35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
                100                 105                 110

Arg Tyr Cys Arg Leu Lys Lys Cys Phe Arg Ala Gly Met Lys Lys Glu
            115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
                180                 185                 190

Glu Gln Leu Leu Val Leu Val Glu Trp Ala Lys Tyr Ile Pro Ala Phe
            195                 200                 205

Cys Glu Leu Pro Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
                260                 265                 270

Val Leu Pro Phe Gln Glu Leu Gln Ile Asp Asp Asn Glu Tyr Ala Tyr
            275                 280                 285

Leu Lys Ala Ile Ile Phe Phe Asp Pro Asp Ala Lys Gly Leu Ser Asp
    290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
    355                 360                 365

Leu Leu Gln Glu Met Leu Leu Gly Gly Ser Pro Ser Asp Ala Pro His
    370                 375                 380

Ala His His Pro Leu His Pro His Leu Met Gln Glu His Met Gly Thr
385                 390                 395                 400
```

```
Asn Val Ile Val Ala Asn Thr Met Pro Thr His Leu Ser Asn Gly Gln
            405                 410                 415

Met Cys Glu Trp Pro Arg Pro Arg Gly Gln Ala Ala Thr Pro Glu Thr
        420                 425                 430

Pro Gln Pro Ser Pro Pro Gly Gly Ser Gly Ser Glu Pro Tyr Lys Leu
            435                 440                 445

Leu Pro Gly Ala Val Ala Thr Ile Val Lys Pro Leu Ser Ala Ile Pro
        450                 455                 460

Gln Pro Thr Ile Thr Lys Gln Glu Val Ile
465                 470

<210> SEQ ID NO 9
<211> LENGTH: 3340
<212> TYPE: DNA
<213> ORGANISM: Homo sapiens

<400> SEQUENCE: 9
```

| | | | | |
|---|---|---|---|---|
| tgcgggcgtc | tccgccattt | tgtgagtcta | taactcggag | ccgttgggtc | ggttcctgct |    60 |
| attccggcgc | ctccactccg | tccccgcgg | gtctgctctg | tgtgccatgg | acggcattgt |   120 |
| cccagatata | gccgttggta | caaagcgggg | atctgacgag | cttttctcta | cttgtgtcac |   180 |
| taacggaccg | tttatcatga | gcagcaactc | ggcttctgca | gcaaacggaa | atgacagcaa |   240 |
| gaagttcaaa | ggtgacagcc | gaagtgcagg | cgtcccctct | agagtgatcc | acatccggaa |   300 |
| gctccccatc | gacgtcacgg | aggggaagt | catctccctg | ggctgccct | ttgggaaggt |   360 |
| caccaacctc | ctgatgctga | gggaaaaaa | ccaggccttc | atcgagatga | acacggagga |   420 |
| ggctgccaac | accatggtga | actactacac | ctcggtgacc | cctgtgctgc | gcggccagcc |   480 |
| catctacatc | cagttctcca | accacaagga | gctgaagacc | gacagctctc | ccaaccaggc |   540 |
| gcgggcccag | gcggccctgc | aggcggtgaa | ctcggtccag | tcggggaacc | tggccttggc |   600 |
| tgcctcggcg | gcggccgtgg | acgcaggat | ggcgatggcc | gggcagagcc | ccgtgctcag |   660 |
| gatcatcgtg | gagaacctct | tctaccctgt | gaccctggat | gtgctgcacc | agattttctc |   720 |
| caagttcggc | acagtgttga | agatcatcac | cttcaccaag | aacaaccagt | tccaggccct |   780 |
| gctgcagtat | gcggaccccg | tgagcgccca | gcacgccaag | ctgtcgctgg | acgggcagaa |   840 |
| catctacaac | gcctgctgca | cgctgcgcat | cgacttttcc | aagctcacca | gcctcaacgt |   900 |
| caagtacaac | aatgacaaga | gccgtgacta | cacacgccca | gacctgcctt | ccggggacag |   960 |
| ccagccctcg | ctggaccaga | ccatggccgc | ggccttcgt | gcacctggta | taatctcagc |  1020 |
| ctctccgtat | gcaggagctg | gtttccctcc | cacctttgcc | attcctcaag | ctgcaggcct |  1080 |
| ttccgttccg | aacgtccacg | gcgccctggc | ccccctggcc | atccctcgg | cggcggcggc |  1140 |
| agctgcggcg | gcaggtcgga | tcgccatccc | gggcctggcg | ggggcaggaa | attctgtatt |  1200 |
| gctggtcagc | aacctcaacc | cagagagagt | cacaccccaa | agcctcttta | ttcttttcgg |  1260 |
| cgtctacggt | gacgtgcagc | gcgtgaagat | cctgttcaat | aagaaggaga | acgccctagt |  1320 |
| gcagatggcg | gacggcaacc | aggcccagct | ggccatgagc | cacctgaacg | gcacaagct |  1380 |
| gcacgggaag | cccatccgca | tcacgctctc | gaagcaccag | aacgtgcagc | tgccccgcga |  1440 |
| gggccaggag | gaccagggcc | tgaccaagga | ctacggcaac | tcacccctgc | accgcttcaa |  1500 |
| gaagccgggc | tccaagaact | tccagaacat | attcccgccc | tcggccacgc | tgcacctctc |  1560 |
| caacatcccg | ccctcagtct | ccgaggagga | tctcaaggtc | ctgttttcca | gcaatggggg |  1620 |
| cgtcgtcaaa | ggattcaagt | tcttccagaa | ggaccgcaag | atggcactga | tccagatggg |  1680 |

-continued

```
ctccgtggag gaggcggtcc aggccctcat tgacctgcac aaccacgacc tcggggagaa    1740
ccaccacctg cgggtctcct tctccaagtc caccatctag gggcacaggc ccccacggcc    1800 gggcccctg gcgacaactt ccatcattcc agagaaaagc cactttaaaa acagctgaag     1860 tgacctagc agaccagaga ttttatttt ttaaagagaa atcagtttac ctgttttaa       1920 aaaaattaaa tctagttcac cttgctcacc ctgcggtgac agggacagct caggctcttg    1980
gtgactgtgg cagcgggagt tcccggcct ccacacccgg ggccagaccc tcggggccat     2040
gccttggtgg ggctgtgtc gggcgtgggg cctgcaggtg ggcgccccga ccacgacttg     2100
gcttccttgt gccttaaaaa acctgccttc ctgcagccac acaccaccc ggggtgtcct     2160 ggggacccaa ggggtggggg ggtcacacca gagagaggca gggggcctgg ccggctcctg    2220
caggatcatg cagctgggc gcggcggccg cggctgcgac accccaaccc cagccctcta    2280
atcaagtcac gtgattctcc cttcaccccg cccccagggc cttcccttct gccccaggc    2340 gggctccccg ctgctccagc tgcggagctg gtcgacataa tctctgtatt atatactttg    2400
cagttgcaga cgtctgtgcc tagcaatatt ccagttgac caaatattct aatcttttt     2460 catttatatg caaagaaat agttttaagt aactttttat agcaagatga tacaatggta    2520
tgagtgtaat ctaaacttcc ttgtggtatt accttgtatg ctgttacttt tattttattc   2580
cttgtaatta agtcacaggc aggacccagt ttccagagag caggcgggc cgcccagtgg    2640 gtcaggcaca gggagccccg gtcctatctt agagcccctg agcttcaggg aagggcggg    2700 cgtgtcgccg cctctggcat cgcctccggt tgccttacac cacgccttca cctgcagtcg   2760
cctagaaaac ttgctctcaa acttcagggt ttttcttcc ttcaaatttt ggaccaaagt    2820
ctcatttctg tgttttgcct gcctctgatg ctgggacccg gaaggcgggc gctcctcctg   2880
tcttctctgt gctctttcta ccgccccgc gtcctgtccc gggggctctc ctaggatccc    2940
ctttccgtaa aagcgtgtaa caagggtgta aatatttata atttttata cctgttgtga    3000 gacccgaggg gcggcggcgc ggttttttat ggtgacacaa atgtatattt tgctaacagc   3060
aattccaggc tcagtattgt gaccgcggag ccacagggga ccccacgcac attccgttgc   3120
cttacccgat ggcttgtgac gcggagagaa ccgattaaaa ccgtttgaga aactcctccc   3180
ttgtctagcc ctgtgttcgc tgtggacgct gtagaggcag gttggccagt ctgtacctgg   3240
acttcgaata aatcttctgt atcctcgctc cgttccgcct taaaaaaaaa aaaaaaaaa   3300 aaaaaaaa aaaaaaaaa aaaaaaaaa aaaaaaaa                                3340
```

<210> SEQ ID NO 10
<211> LENGTH: 557
<212> TYPE: PRT
<213> ORGANISM: Homo sapiens

<400> SEQUENCE: 10

```
Met Asp Gly Ile Val Pro Asp Ile Ala Val Gly Thr Lys Arg Gly Ser
1               5                   10                  15

Asp Glu Leu Phe Ser Thr Cys Val Thr Asn Gly Pro Phe Ile Met Ser
            20                  25                  30

Ser Asn Ser Ala Ser Ala Ala Asn Gly Asn Asp Ser Lys Lys Phe Lys
        35                  40                  45

Gly Asp Ser Arg Ser Ala Gly Val Pro Ser Arg Val Ile His Ile Arg
    50                  55                  60

Lys Leu Pro Ile Asp Val Thr Glu Gly Glu Val Ile Ser Leu Gly Leu
65                  70                  75                  80
```

```
Pro Phe Gly Lys Val Thr Asn Leu Leu Met Leu Lys Gly Lys Asn Gln
                85                  90                  95
Ala Phe Ile Glu Met Asn Thr Glu Glu Ala Ala Asn Thr Met Val Asn
            100                 105                 110
Tyr Tyr Thr Ser Val Thr Pro Val Leu Arg Gly Gln Pro Ile Tyr Ile
        115                 120                 125
Gln Phe Ser Asn His Lys Glu Leu Lys Thr Asp Ser Ser Pro Asn Gln
    130                 135                 140
Ala Arg Ala Gln Ala Ala Leu Gln Ala Val Asn Ser Val Gln Ser Gly
145                 150                 155                 160
Asn Leu Ala Leu Ala Ala Ser Ala Ala Ala Val Asp Ala Gly Met Ala
                165                 170                 175
Met Ala Gly Gln Ser Pro Val Leu Arg Ile Ile Val Glu Asn Leu Phe
            180                 185                 190
Tyr Pro Val Thr Leu Asp Val Leu His Gln Ile Phe Ser Lys Phe Gly
        195                 200                 205
Thr Val Leu Lys Ile Ile Thr Phe Thr Lys Asn Asn Gln Phe Gln Ala
    210                 215                 220
Leu Leu Gln Tyr Ala Asp Pro Val Ser Ala Gln His Ala Lys Leu Ser
225                 230                 235                 240
Leu Asp Gly Gln Asn Ile Tyr Asn Ala Cys Cys Thr Leu Arg Ile Asp
                245                 250                 255
Phe Ser Lys Leu Thr Ser Leu Asn Val Lys Tyr Asn Asn Asp Lys Ser
            260                 265                 270
Arg Asp Tyr Thr Arg Pro Asp Leu Pro Ser Gly Asp Ser Gln Pro Ser
        275                 280                 285
Leu Asp Gln Thr Met Ala Ala Ala Phe Gly Ala Pro Gly Ile Ile Ser
    290                 295                 300
Ala Ser Pro Tyr Ala Gly Ala Gly Phe Pro Pro Thr Phe Ala Ile Pro
305                 310                 315                 320
Gln Ala Ala Gly Leu Ser Val Pro Asn Val His Gly Ala Leu Ala Pro
                325                 330                 335
Leu Ala Ile Pro Ser Ala Ala Ala Ala Ala Ala Ala Ala Gly Arg Ile
            340                 345                 350
Ala Ile Pro Gly Leu Ala Gly Ala Gly Asn Ser Val Leu Leu Val Ser
        355                 360                 365
Asn Leu Asn Pro Glu Arg Val Thr Pro Gln Ser Leu Phe Ile Leu Phe
    370                 375                 380
Gly Val Tyr Gly Asp Val Gln Arg Val Lys Ile Leu Phe Asn Lys Lys
385                 390                 395                 400
Glu Asn Ala Leu Val Gln Met Ala Asp Gly Asn Gln Ala Gln Leu Ala
                405                 410                 415
Met Ser His Leu Asn Gly His Lys Leu His Gly Lys Pro Ile Arg Ile
            420                 425                 430
Thr Leu Ser Lys His Gln Asn Val Gln Leu Pro Arg Glu Gly Gln Glu
        435                 440                 445
Asp Gln Gly Leu Thr Lys Asp Tyr Gly Asn Ser Pro Leu His Arg Phe
    450                 455                 460
Lys Lys Pro Gly Ser Lys Asn Phe Gln Asn Ile Phe Pro Pro Ser Ala
465                 470                 475                 480
Thr Leu His Leu Ser Asn Ile Pro Pro Ser Val Ser Glu Glu Asp Leu
                485                 490                 495
```

```
Lys Val Leu Phe Ser Ser Asn Gly Gly Val Val Lys Gly Phe Lys Phe
            500             505             510

Phe Gln Lys Asp Arg Lys Met Ala Leu Ile Gln Met Gly Ser Val Glu
        515             520             525

Glu Ala Val Gln Ala Leu Ile Asp Leu His Asn His Asp Leu Gly Glu
        530             535             540

Asn His His Leu Arg Val Ser Phe Ser Lys Ser Thr Ile
545             550             555
```